US005811300A

United States Patent [19]
Sullivan et al.

[11] Patent Number: 5,811,300
[45] Date of Patent: *Sep. 22, 1998

[54] TNF-α RIBOZYMES

[75] Inventors: Sean Sullivan, Alameda, Calif.; Kenneth Draper, Boulder, Colo.; Kevin Kisich, Lafayette, Colo.; Dan T. Stinchcomb; James McSwiggen, both of Boulder, Colo.

[73] Assignee: Ribozyme Pharmaceuticals, Inc., Boulder, Colo.

[*] Notice: The portion of the term of this patent subsequent to May 4, 2015, has been disclaimed.

[21] Appl. No.: 311,486

[22] Filed: Sep. 23, 1994

Related U.S. Application Data

[63] Continuation-in-part of Ser. No. 989,849, Dec. 7, 1992, abandoned, and Ser. No. 8,895, Jan. 19, 1993, abandoned.

[51] Int. Cl.$^6$ .............................. C12N 15/85; C12Q 1/68
[52] U.S. Cl. ........................... 435/366; 435/6; 435/91.31; 435/172.3; 435/320.1; 435/325; 536/23.1; 536/23.2; 536/24.5; 514/44
[58] Field of Search ............................. 435/91.31, 172.3, 435/320.1, 6; 514/44; 536/23.1, 24.5, 23.2

[56] References Cited

U.S. PATENT DOCUMENTS

| | | | |
|---|---|---|---|
| 4,987,071 | 1/1991 | Cech | 435/91.31 |
| 5,168,053 | 12/1992 | Altman et al. | 514/44 |
| 5,334,711 | 8/1994 | Sproat et al. | 536/24.5 |

FOREIGN PATENT DOCUMENTS

| | | |
|---|---|---|
| 9115580 | 7/1991 | WIPO . |
| 9118624 | 12/1991 | WIPO . |
| 9118625 | 12/1991 | WIPO . |
| 9118913 | 12/1991 | WIPO . |
| 9207065 | 4/1992 | WIPO . |
| 9200080 | 9/1992 | WIPO . |
| 9103162 | 12/1992 | WIPO . |
| 9315187 | 8/1993 | WIPO . |
| 9323569 | 11/1993 | WIPO . |
| 9402595 | 2/1994 | WIPO . |
| 9410301 | 5/1994 | WIPO . |
| 9413688 | 6/1994 | WIPO . |

OTHER PUBLICATIONS

Stall et al. Pharm Res. 12:465–483 1995.
Baringa, "Ribozymes: Killing the Messenger," *Science* 262:1521–1514 (1993).
Berzal–Herranz et al., "Essential nucleotide sequence and secondary structure elements of the hairpin ribozyme," *EBMO J.* 12:2567–2574 (1993).
Beutler et al., "Identity of tumour necrosis factor and the macrophage–secreted factor cachectin," *Nature* 316:552–554 (1985).
Cech, "Ribozymes and Their Medical Implications," *JAMA* 260:3030–3034 (1988).
Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Chowrira and Burke, "Extensive Phsophorothioate Substitution Yields Highly Active and Nuclease–Resistant Hairpin Ribozymes," *Nucleic Acids Res.* 20:2835–2840 (1992).
Collins et al., "Nucleotide Sequences For the Gene Junctions of Human Respiratory Syncytial Virus Reveal Distinctive Features of Intergenic Structure and Gene Order," *Proc. Natl. Acad. Sci. USA* 83:4594–4598 (1986).
Collins and Olive, "Reaction Conditions and Kinetics of Self–Cleavage of a Ribozyme Derived From Neurospora VS RNA," *Biochemistry* 32:2795–2799 (1993).
Dropulic et al., "Functional Characterization of a U5 Ribozyme: Intracellular Suppression of Human Immunodeficiency Virus Type I Expression," *Journal of Virology* 66:1432–1441 (1992).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Fauci, "Cytokin Regulation of HIV Expression," *Lymphokine Res.* 9:527–531 (1990).
Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).
Guerrier–Takada et al., "The RNA Moiety of Ribonuclease P Is the Catalytic Subunit of the Enzyme," *Cell* 35:849–857 (1983).
Hampel and Tritz, "RNA Catalytic Properties of the Minimum (–)sTRSV Sequence," *Biochemistry* 28:4929–4933 (1989).
Hampel et al., "'Hairpin' Catalytic RNA Model: Evidence for Helices and Sequence Requirement for Substrate RNA", *Nucleic Acids Research* 18:299–304 (1990).
Harris et al., "Rheumatoid Arthritis: Pathophysiology and Implications for Therapy," *N. Engl. J. Med.* 332:1277–1289 (1990).
Haseloff and Gerlach, "Simple RNA Enzymes with New and Highly Specific Endoribonuclease Activities," *Nature* 334:585–591 (1988).
Hertel et al., "Numbering System for the Hammerhead," *Nucleic Acids Res.* 20:3252 (1992).
Hession et al., WO 9013300 (Nov. 15, 1990) provided as CA Abstr. Acc#114(25): 292037g.
Jaeger et al., "Improved Predictions of Secondary Structures for RNA," *Proc. Natl. Acad. Sci. USA* 86:7706–7710 (1989).
Jeffries and Symons, "A Catalytic 13–mer Ribozyme," *Nucleic Acids Research* 17:1371–1377 (1989).
Johnston and Hoth, "Present Status and Future Prospects for HIV Therapies," *Science* 260:1286–1293 (1993).

(List continued on next page.)

*Primary Examiner*—John L. LeGuyader
*Attorney, Agent, or Firm*—Lyon & Lyon LLP

[57] ABSTRACT

Enzymatic RNA molecules which cleave TNF-α mRNA.

13 Claims, 10 Drawing Sheets

OTHER PUBLICATIONS

Descamps–Latscha et al., "Increased Plasma Levels of Soluble CD23 in Patients with End Stage Chronic Renal Failure," *J. Leukocyte Biol.* Sup. 2:70 (1991).

Kashani–Sabet et al., "Reversal of the Malignant Phenotype by an Anti–ras Ribozyme," *Antisense Research & Development* 2:3–15 (1992).

Kim et al., *Proc. Natl. Acad. Sci. USA* 84:788 (1987).

Kisich et al., "Anti–Tumor Necrosis Factor–α Ribozymes Specifically Cleave NBative mRNA AMong TotalCellular RNa in Vitro," *FASEB J* 4:A 1860 at 970 (1990) (abstract).

Kriegler et al., "A Novel Form of TNF/Cachectin is a Cell Surface Cytotoxic Transmembrane Protein: Ramifications for the Complex Physiology of TNF," *Cell* 53:45–53 (1988).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Mamone et al., "Design of Hammerhead Ribozymes Targeted to Sequences in HIV, HSV and the RAT ANF Gene," Abstract of Keystone, CO (May 27, 1992).

Milligan and Uhlenbeck, "Synthesis of Small RNAs Using T7 RNA Polymease," *Methods Enzymol,* 180:51–62 (1989).

Nabel et al., "Site–Specific Gene Expression in Vivo by Direct Gene Transfer Into the Arterial Wall," *Science* 249:1285–1288 (1990).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Old, "Tumor Necrosis Factor (TNF)," *Science* 230:4255–4231 (1985).

Parillo et al., "Pathogenetic Mechanisms of Septic Shock," *N. Eng. J. Med.* 328:1471–1477 (1993).

Pavco et al., "Regulation of Self–Splicing Reactions by Antisense RNA," Abstract of Keystone, CO (May 27, 1992).

Pieken et al., "Kinetic Characterization of Ribonuclease–Resistant 2'–Modified Hammerhead Ribozymes," *Science* 253:314–317 (1991).

Perrotta and Been, "Cleavage of Oligoribonucleotides by a Ribozyme Derived from the Hepatitis ε Virus RNA Sequence," *Biochemistry* 31:16–21 (1992).

Rossi et al, "Ribozymes as Anti–HIV–1 Therapeutic Agents: Principles, Applications, and Problems," *Aids Research and Human Retroviruses* 8:183 (1992).

Rossi et al., "Ribozyme Mediated Intracellular Immunity to HIV–1 in CD4," *J. Cell Biochem.* Suppl 14A:D428 (1990).

Sarver et al., "Ribozymes as Potential Anti–HIV–1 Therapeutic Agents" *Science* 247:1222–1225 (1990).

Sarver et al., "Catalytic RNAs (Ribozymes): A New Frontier in Biomedical Applications," *AIDS Res. Revs.* 2:259 (1992).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Shakhov et al., "$_\kappa$B–Type Enhancers are Involved in Lipopolysaccharide–Mediated Transcriptional Activatio of the Tumor Necrosis Factor α Gene in Primary Macrophages," *J. Exp. Med.* 171:35–47 (1990).

Smith, "A Receptor for Tumor Necrosis Factor Defines an Unusual Family of Cellular and Viral Proteins," *Science* 248:1019–1023 (1990).

Sioud et al., *J. Mol. Biol.* 223:831–835 (1992).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tanabe et al., *J. Biol. Chem.* 262:16580 (1987), provided as BIOSIS Abstr. 85047487.

Tracey and Cerami, "Tumor Necrosis Factor in the Malnutrition (Cachexia) of Infection and Cancer," *Am. J. Trop. Med. Hyg.* 47:2–7 (1992).

Turestskaya et al., "Genomic Structure, Induction, and Production of TNF–β," *Tuumor Necrosis Factor: Structure Function and Mechanism of Action,* BB Aggarwal, J. Vilcek, Eds. Marcel Dekker, Inc. pp. 35–60 (1991).

Uhlenbeck, "A Small Catalytic Oligoribonucleotide," *Nature* 328:596–600 (1987).

Perreault et al., "Mixed Deoxyribo–and Ribo Oligonucleotides with Catalytic Activity," *Nature* 344:565–567 (1990).

Usman and Cedergren, "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Van Deuren et al., "Cytokines and the Response to Infection," *J. Pathol.* 168:349–356 (1992).

Ventura et al., "Activation of HIV–Specific Ribozyme Activity by Self–Cleavage," *Nucleic Acids Research* 21:3249–3255 (1993).

Woolf et al., "Specificity of Antisense Oligonucleotides in vivo," *Proc. Natl. Acad. Sci. USA* 89:7305–7309 (1992).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–4 (1994).

Willard et al., "Recombinant Adenovirus in an Efficient Vector for In Vivo Gene Transfer and can be Preferentially Directed at Vascular Endotheliunaram or Smooth Muscle Cells," *Circulation—Abstracts from the 6th Scientific Sessions,* New Orleans Convention Center, New Orleans, Louisiana, Nov. 16–19, 199286:I–473 at 1880 (Abstract).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zhou et al., "Synthesis of Functional mRNA in Mammalian Cells by Bacteriophage T3 RNA Polymerase," *Mol. Cell. Biol.* 10:4529–4537 (1990).

Ballantyne et al., "Nucleotide sequence of the cDNA for murine intercellular adhesion molecule–1 (JCAM–1)," *Nucleic Acids Research* 17:5853 (1989).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM–1," *Biochem. Biophys. Acta* 1131:108–110 (1992).

Simons et al., "ICAM, an adhesion ligand of LFA–1, is homologous to the neutral cell adhesion molecule NCAM," *Nature* 331:624–627 (1988).

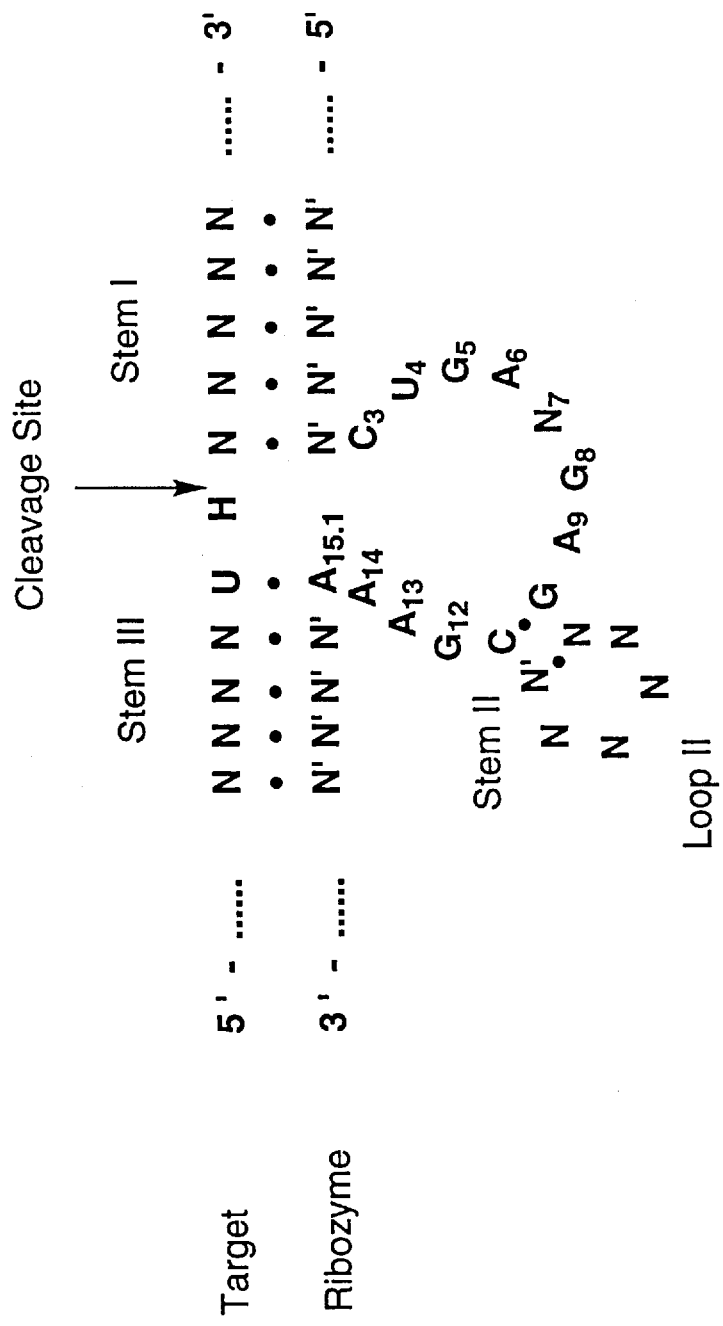
Figure 1. The Hammerhead Ribozyme

Figure 4: Hepatitis Delta Virus Ribozyme

Neurospora VS RNA ENZYME

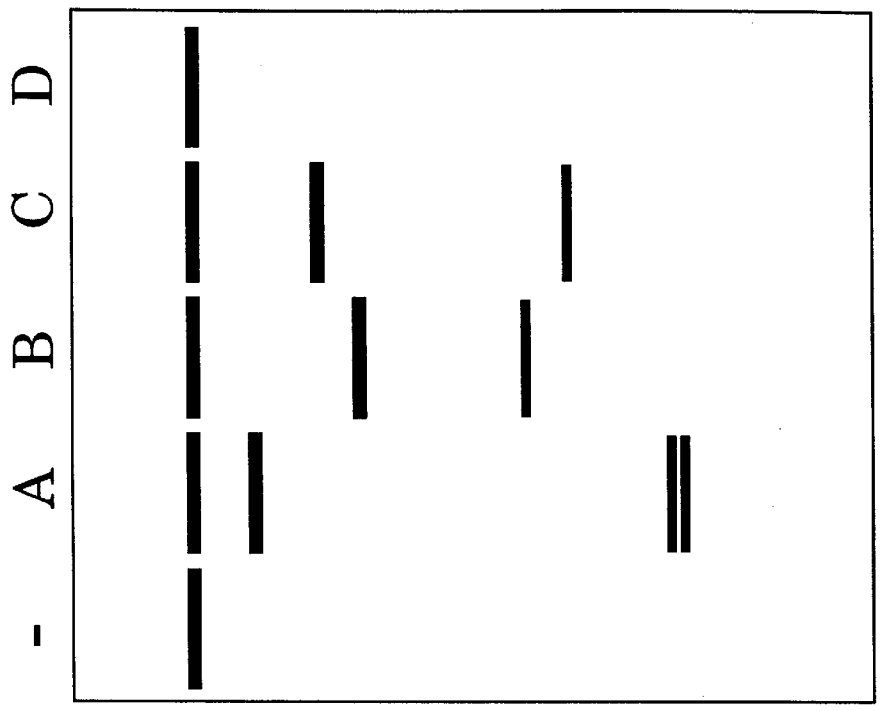
Figure 6: RNase H Assay
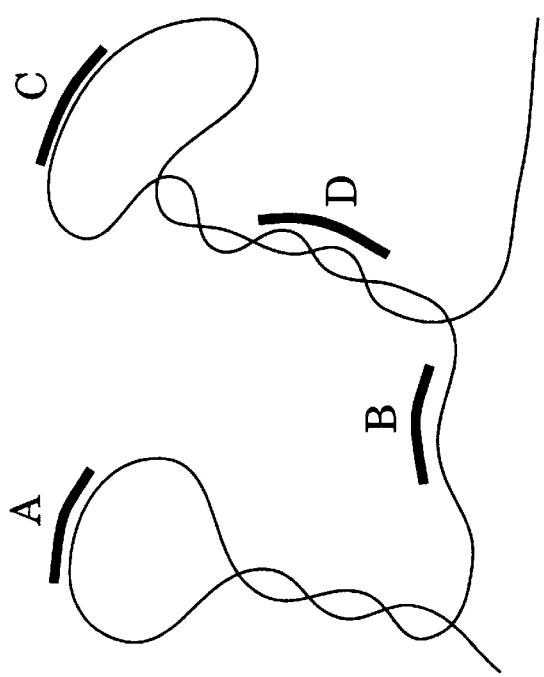
- Body-labeled transcript (not purified)
- DNA oligo (10 nM, 100 nM and 1000 nM)
- RNAse H (0.08 - 1.0 u/μl)
- 37°C, 10 min

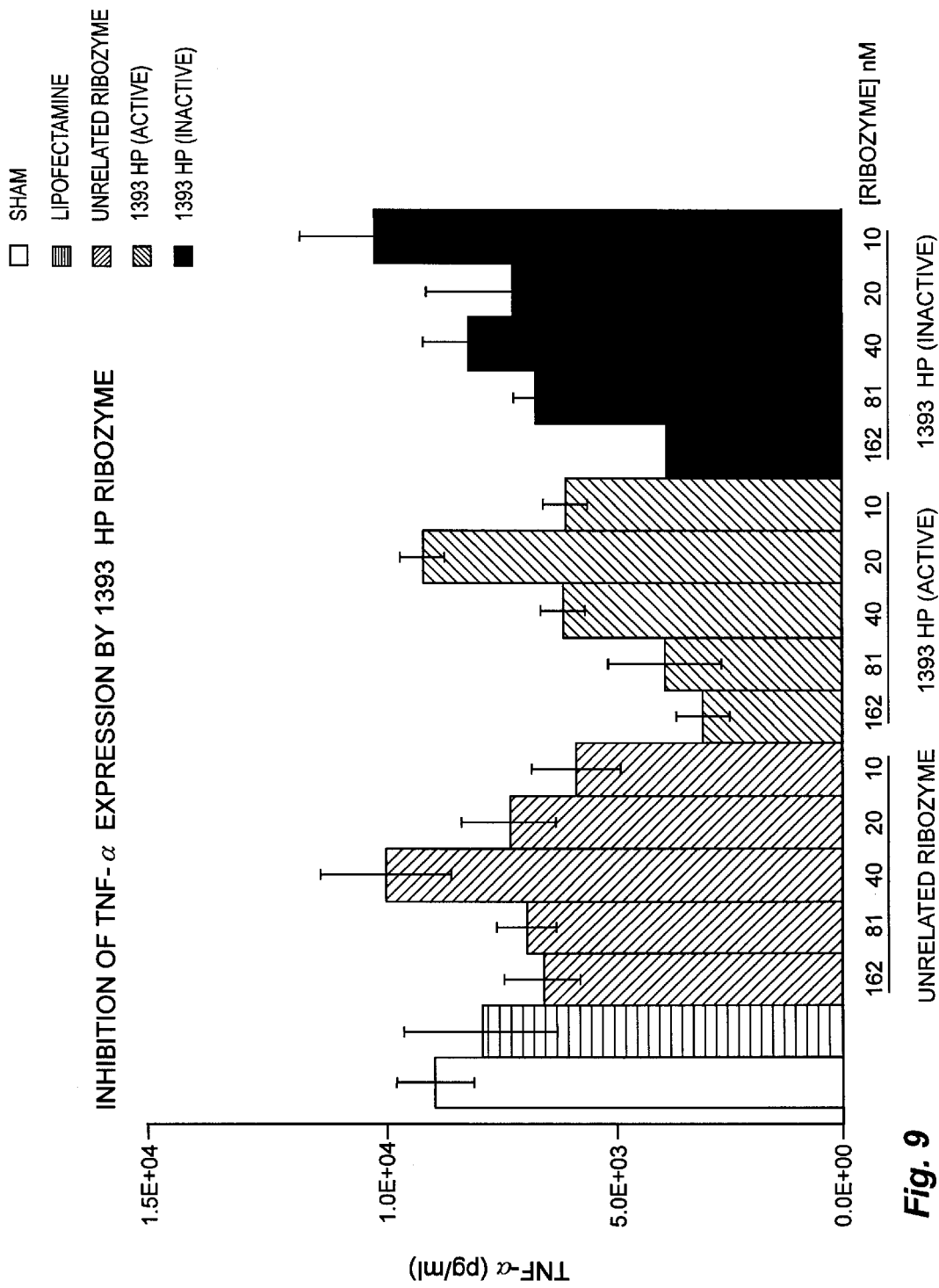

TNF-α RIBOZYMES

RELATED APPLICATIONS

This application is a continuation-in-part of Sullivan and Draper, "Method and Reagent for Treatment of Inflammatory Disease", U.S. Ser. No. 07/989,849 (filed Dec. 7, 1992), now abandoned, and U.S. Ser. No. 08/008,895 (filed Jan. 19, 1993), now abandoned, both hereby incorporated in their totality (in including drawings) by reference herein.

FIELD OF THE INVENTION

The present invention relates to therapeutic compositions and methods for the treatment or diagnosis of diseases or conditions related to TNF-α levels, such as septic shock, rheumatoid arthritis, HIV and AIDS, psoriasis, inflammatory or autoimmune disorders.

BACKGROUND OF THE INVENTION

The following is a brief description of the physiological role of TNF-α. The discussion is not meant to be complete and is provided only for understanding of the invention that follows. This summary is not an admission that any of the work described below is prior art to the claimed invention.

The identification and cloning of the cytokines have provided a wealth of data on endogenous immunological and inflammatory mediators and their role in host defense against infection (van Deuren et al., 1992 *J. Pathol.* 168, 349–356). Cytokines also have been associated with pathology due to over-expression or inappropriate production. Cytokine cascades are implicated in the tissue damage that occurs during gram negative septic shock (Parrillo, 1993 *N. Engl. J. Med.* 328, 1471–1477), in the joint inflammation and tissue destruction that occurs during rheumatoid arthritis (Harris, 1990 *N. Engl. J. Med.* 322, 1277), and in a positive feedback loop between cytokine production and the replication of human immunodeficiency virus (HIV) (Fauci, 1990 *Lymphokine Res.* 9, 527–531). A common thread interweaving these pathological conditions is their association with abnormally high levels of the proinflammatory cytokine tumor necrosis factor-α (TNF-α).

Tumor necrosis factor-α (TNF-α) is a protein, secreted by activated leukocytes, that is a potent mediator of inflammatory reactions. Injection of TNF-α into experimental animals can simulate the symptoms of systemic and local inflammatory diseases such as septic shock or rheumatoid arthritis.

TNF-α was initially described as a factor secreted by activated macrophages which mediates the destruction of solid tumors in mice (Old, 1985 *Science* 230, 4225–4231). TNF-α subsequently was found to be identical to cachectin, an agent responsible for the weight loss and wasting syndrome associated with tumors and chronic infections (Beutler, et al., 1985 *Nature* 316, 552–554). The cDNA and the genomic locus for TNF-α have been cloned and found to be related to TNF-β (Shakhov et al., 1990 *J. Exp. Med.* 171, 35–47). Both TNF-α and TNF-β bind to the same receptors and have nearly identical biological activities. The two TNF receptors have been found on most cell types examined (Smith, et al., 1990 *Science* 248, 1019–1023). TNF-α secretion has been detected from monocytes/macrophages, CD4+ and CD8+ T-cells, B-cells, lymphokine activated killer cells, neutrophils, astrocytes, endothelial cells, smooth muscle cells, as well as various non-hematopoietic tumor cell lines (for a review see Turestskaya et al., 1991 in *Tumor Necrosis Factor: Structure, Function, and Mechanism of Action* B. B. Aggarwal, J. Vilcek, Eds. Marcel Dekker, Inc., pp. 35–60).

TNF-α is regulated transcriptionally and translationally, and requires proteolytic processing at the plasma membrane in order to be secreted (Kriegler et al., 1988 *Cell* 53, 45–53). Once secreted, the serum half life of TNF-α is approximately 30 minutes. The tight regulation of TNF-α is important due to the extreme toxicity of this cytokine. Increasing evidence indicates that overproduction of TNF-α during infections can lead to severe systemic toxicity and death (Tracey & Cerami, 1992 *Am. J. Trop. Med. Hyg.* 47, 2–7).

Antisense RNA and Hammerhead ribozymes have been used in an attempt to lower the expression level of TNF-α by targeting specified cleavage sites [Sioud et al., 1992 *J. Mol. Biol.* 223; 831; Sioud WO 94/10301; Kisich and co-workers, 1990 abstract (*FASEB J.* 4, A1860; 1991 slide presentation (*J. Leukocyte Biol.* sup. 2, 70); December, 1992 poster presentation at Anti-HIV Therapeutics Conference in SanDiego, Calif.; and "Development of anti-TNF-α ribozymes for the control of TNF-α gene expression"— Kisich, Doctoral Dissertation, 1993 University of California, Davis] listing various TNFα targeted ribozymes.

SUMMARY OF THE INVENTION

This invention relates to ribozymes, or enzymatic RNA molecules, directed to cleave mRNA species encoding specific sites in TNF-α. In particular, applicant describes the selection and function of ribozymes capable of cleaving this RNA and their use to reduce activity of TNF-α in various tissues to treat the diseases discussed herein. Such ribozymes are also useful for diagnostic applications.

Ribozymes that cleave the specified cites in TNF-α mRNA represent a novel therapeutic approach to inflammatory or autoimmune disorders. Applicant indicates that ribozymes are able to inhibit the activity of TNF-α and that the catalytic activity of the ribozymes is required for their inhibitory effect. Those of ordinary skill in the art, will find that it is clear from the examples described that other ribozymes that cleave these sites in TNF-α encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA,* 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target TNF-α encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eucaryotic promoters (e.g., Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225). Those skilled in the art realize that any ribozyme can be expressed in eucaryotic cells from the appropriate DNA vector. The activity of such ribozymes can be augmented by their release from the primary transcript by a second ribozyme (Draper et al., PCT WO 93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55).

Inflammatory mediators such as lipopolysaccharide (LPS), interleukin-1 (IL-1) or tumor necrosis factor-a (TNF-α) act on cells by inducing transcription of a number of secondary mediators, including other cytokines and adhesion molecules. Ribozyme therapy, due to its exquisite specificity, is particularly well-suited to target intracellular factors that contribute to disease pathology. Thus, ribozymes that cleave the mRNA sites encoded by TNF-α may represent novel therapeutics for the treatment of inflammatory and autoimmune disorders.

Thus, in a first aspect, the invention features ribozymes that inhibit TNF-α production by cleavage at designated sites in TNF-α encoding mRNA. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target TNF-α encoding mRNAs, preventing translation and TNF-α protein accumulation. In the absence of the expression of the target gene, a therapeutic effect may be observed.

By "inhibit" is meant that the activity or level of TNF-α encoding mRNA is reduced below that observed in the absence of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of TNF-α activity in a cell or tissue. By "related" is meant that the inhibition of TNF-α mRNA and thus reduction in the level of TNF-α activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II, IV, VI–VII. Examples of such ribozymes are shown in Tables III, V–VII. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit TNF-α activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors.

However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.
Drawings:

FIG. 1 is a diagrammatic representation of the hammerhead ribozyme domain known in the art. Stem II can be $\geq 2$ base-pair long, or can even lack base pairs and consist of a loop region.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature,* 334, 585–591) into two portions; and FIG. 2d is a similar diagram showing the hammerhead divided by Jeffries and Symons (1989, *Nucl. Acids. Res.,* 17, 1371–1371) into two portions.

FIG. 3 is a representation of the general structure of the hairpin ribozyme domain known in the art. H, is A, U or C. Y is U or C. N is A, U, G, or C. N' is the complementary sequence of N. Helix 4 can be $\geq 2$ base-pair long.

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figures 1, 2, 7A:
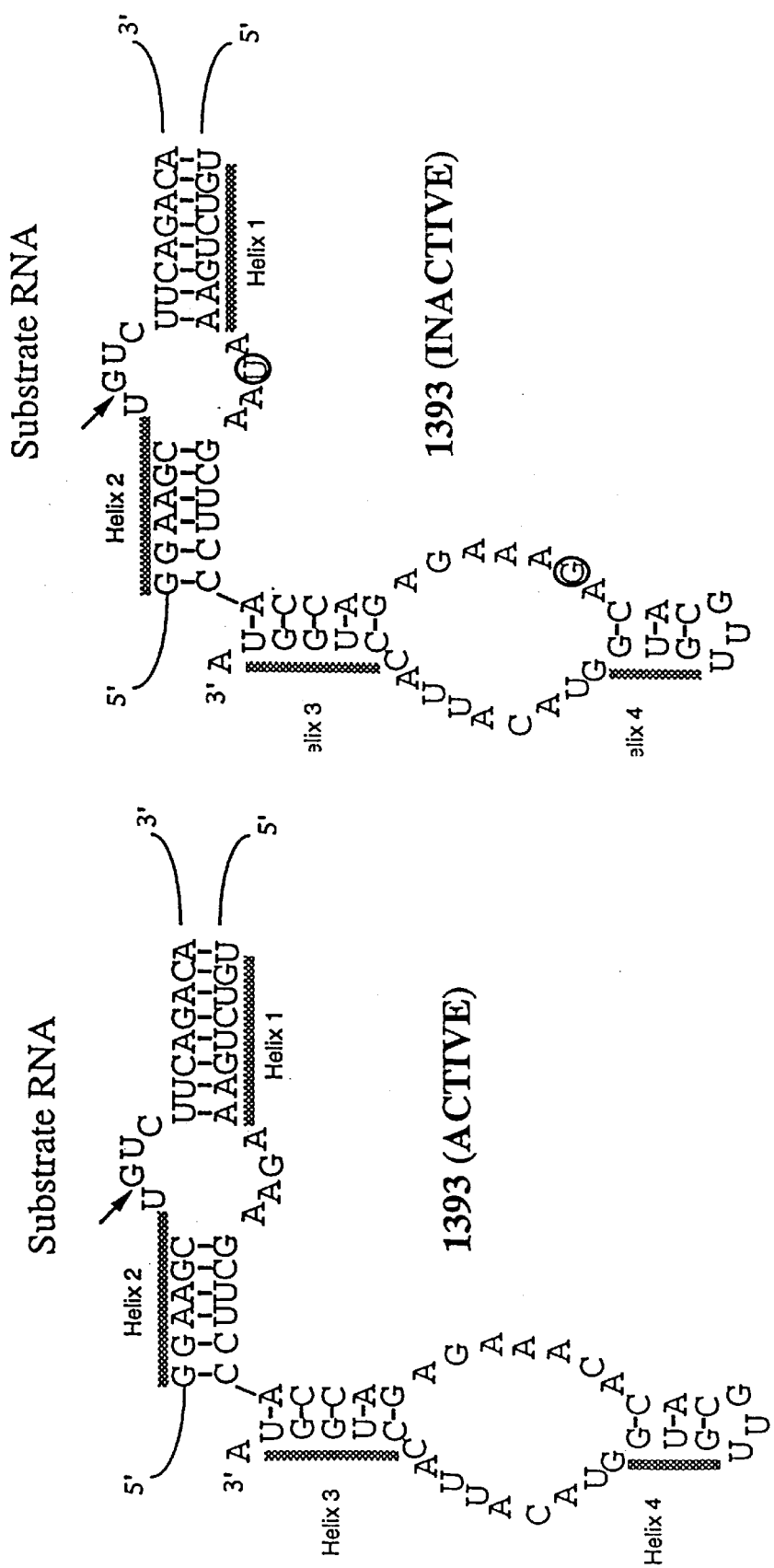
Figures 2, 7B:
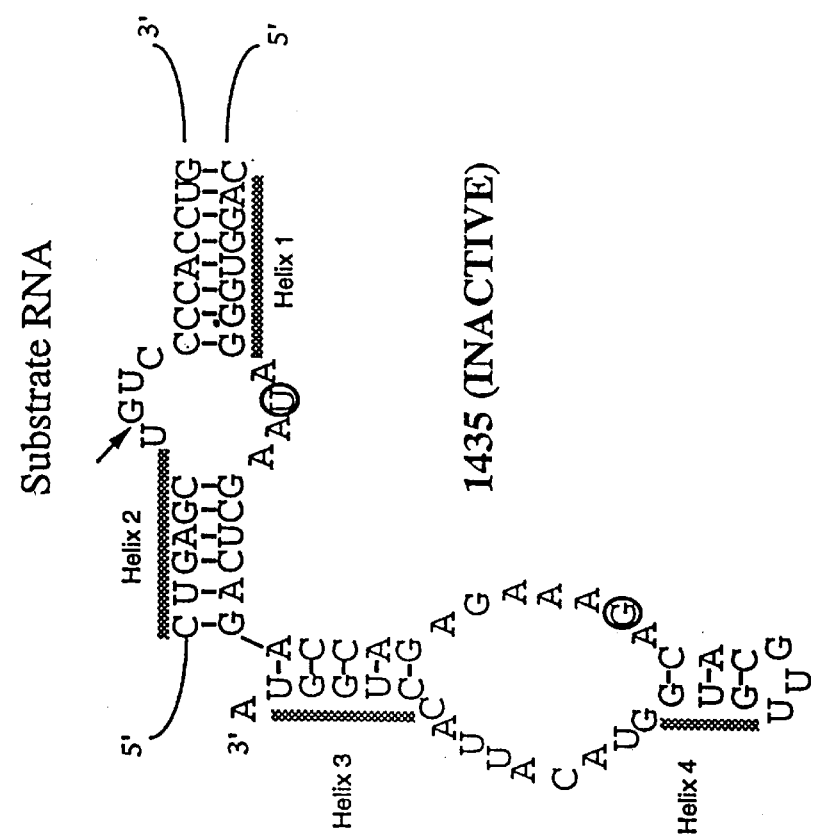
Figures 1, 7B:
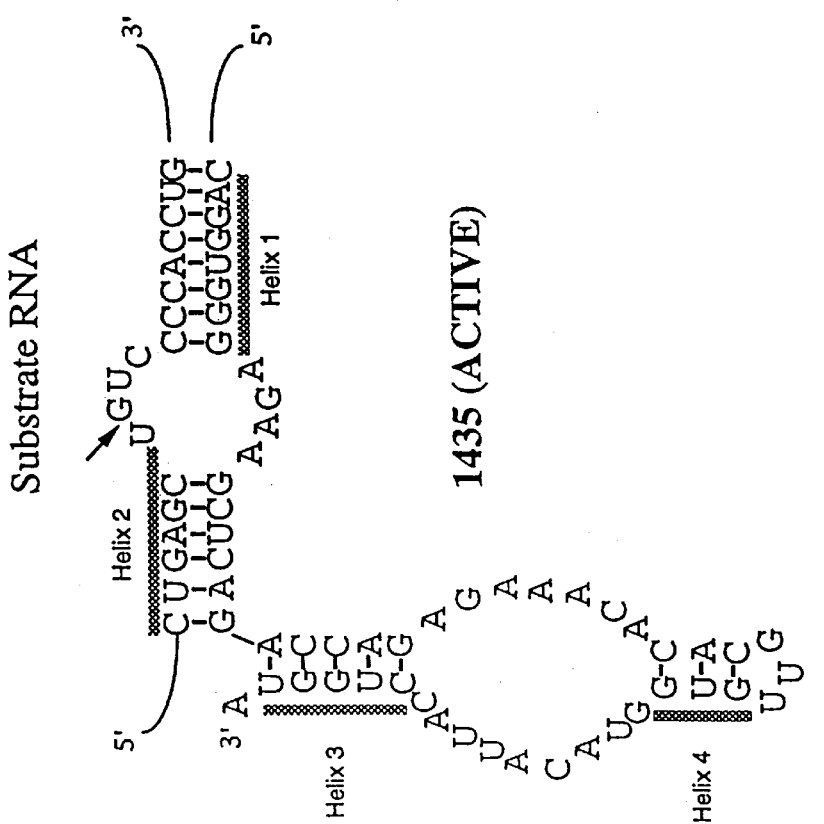

FIG. 7 schematic representation of hairpin ribozymes targeted against sites in TNF-α mRNA. Helix1 and Helix2 represents intermolecular helices formed between ribozyme and the target RNA. Helix3 and Helix4 represents intramolecular helices within the ribozyme. The arrow indicates the site of cleavage. Circled nucleotides are mutations that render the ribozyme catalytically inactive. A) Structure of the hairpin ribozyme.substrate complex for site 1393 in mouse TNF-α mRNA. B) Structure of the hairpin ribozyme·substrate complex for site 1435 in mouse TNF-α mRNA.

Figure 8:
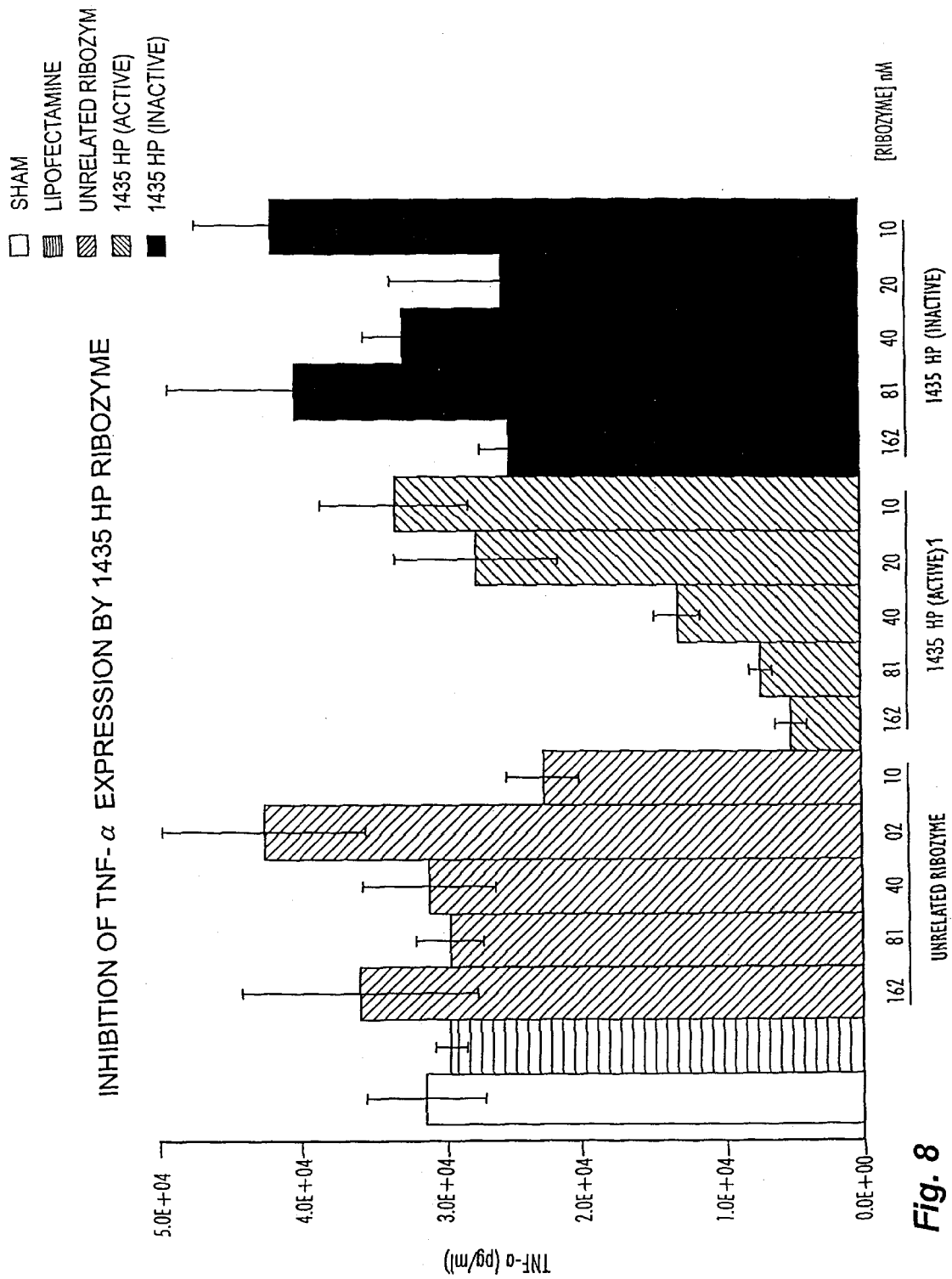

FIG. 8 shows the 1393 hairpin ribozyme-mediated inhibition of TNF-α expression in mouse macrophages.

FIG. 9 shows the 1435 hairpin ribozyme-mediated inhibition of TNF-α expression in mouse macrophages.
Ribozymes Ribozymes of this invention block to some extent TNF-α expression and can be used to treat disease or diagnose such disease. Ribozymes will be delivered to cells in culture and to cells or tissues in animal models of septic shock and rheumatoid arthritis. Ribozyme cleavage of TNF-α mRNA in these systems may prevent inflammatory cell function and alleviate disease symptoms.

Target sites

Targets for useful ribozymes can be determined as disclosed in Draper et al supra. Sullivan et al., supra, as well as by Draper et al., "Method and reagent for treatment of arthritic conditions" U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse and human RNA are provided, those in the art will recognize that the equivalent human RNA targets described can be used as described below. Thus, the same target may be used, but binding arms suitable for targeting human RNA sequences are present in the ribozyme. Such targets may also be selected as described below.

The sequence of human and mouse TNF-α mRNA can be screened for accessible sites using a computer folding algorithm. Hammerhead or hairpin ribozyme cleavage sites were identified. These sites are shown in Tables II, IV, and VI–VII. (All sequences are 5' to 3' in the tables.) While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466,(and hereby incorporated herein by reference), mouse targeted ribozymes are useful to test efficacy of action of the ribozyme prior to testing in humans. The nucleotide base position is noted in the Tables as that site to be cleaved by the designated type of ribozyme. (In Table III, lower case letters indicate positions that are not conserved between the human and the mouse TNF-α sequences.)

Hammerhead ribozymes are designed that could bind and are individually analyzed by computer folding (Jaeger et al., 1989 *Proc. Natl. Acad. Sci. USA,* 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application Ser. No. 07/883,849 filed on May 1, 1992, entitled "Assay for ribozyme target site", hereby incorporated by reference herein. Briefly, DNA oligonucleotides representing potential hammerhead or hairpin ribozyme cleavage sites are synthesized. A polymerase chain reaction is used to generate a substrate for T7 RNA polymerase transcription from human or murine TNF-α cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a Phosphor Imaging system. From these data, hammerhead or hairpin ribozyme sites are chosen as the most accessible.

Ribozymes of the hammerhead or hairpin motif are designed to anneal to various sites in the mRNA message.

The binding arms are complementary to the target site sequences described above. The ribozymes are chemically synthesized. The method of synthesis used follows the procedure for normal RNA synthesis as described in Usman et al., 1987 *J. Am. Chem. Soc..* 109, 7845–7854 and in Scaringe et al., 1990 *Nucleic Acids Res..* 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.,* 20, 3252). Hairpin ribozymes are synthesized in two parts and annealed to reconstruct the active ribozyme (Chowrira and Burke, 1992 *Nucleic Acids Res.,* 20, 2835–2840). Hairpin ribozymes are also synthesized from DNA templates using bacteriophage T7 RNA polymerase (Milligan and Uhlenbeck, 1989, *Methods Enzymol.* 180, 51). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the chemically synthesized ribozymes useful in this study are shown in Tables III, V–VII. Those in the art will recognize that these sequences are representative only of many more such sequences where the enzymatic portion of the ribozyme (all but the binding arms) is altered to affect activity. For example, stem-loop 11 sequence of hammerhead ribozymes listed in Tables III and V (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Tables VI and VII (5'-CACGUUGUG-3') can be altered (substitution, deletion, and/or insertion) to contain any sequence, provided a minimum of two base-paired stem structure can form. The sequences listed in Tables III, V–VII may be formed of ribonucleotides or other nucleotides or non-nucleotides. Such ribozymes are equivalent to the ribozymes described specifically in the Tables.

Optimizing Ribozyme Activity

Figure 2A:
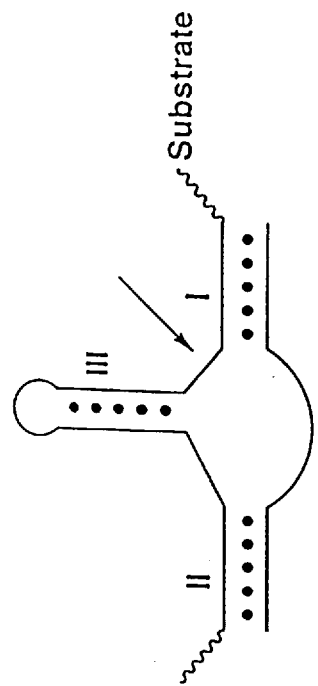
Figure 2B:
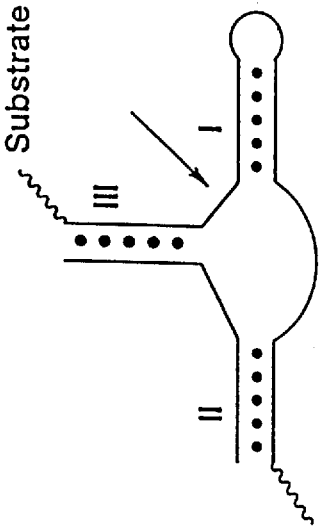
Figure 2C:
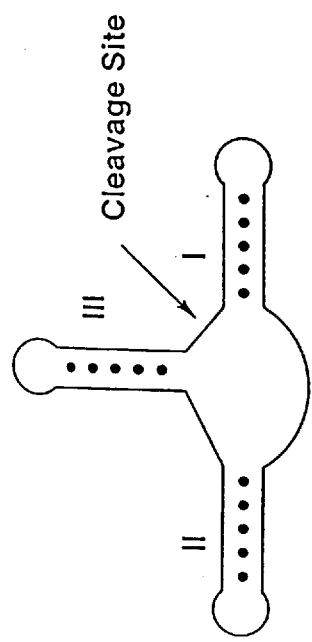
Figure 2D:
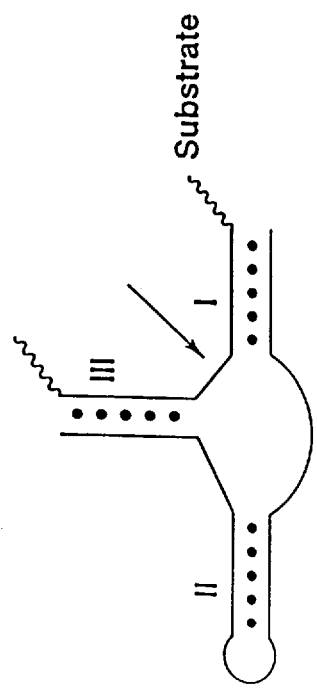

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 and U.S. Pat. No. 5,334,711 and Jennings et al., WO 94/13688 which describe various chemical modifications that can be made to the sugar moieties of enzymatic RNA molecules. Modifications which enhance their efficacy in cells, and removal of stem 11 bases to shorten RNA synthesis times and reduce chemical requirements. (All these publications are hereby incorporated by reference herein.), Sullivan, et al., supra, describes the general methods for delivery of enzymatic RNA molecules . Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eucaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U S A,* 87, 6743–7; Gao and Huang 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. U S A,* 89, 10802–6; Chen et al., 1992 *Nucleic Acids Res.,* 20, 4581–9; Yu et al., 1993 *Proc. Natl. Acad. Sci. U S A,* 90, 6340–4; L'Huillier et al., 1992 *EMBO J.* 11, 4411–8; Lisziewicz et al., 1993 *Proc. Natl. Acad. Sci. U.S.A.,* 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral, sindbis virus, semliki forest virus vectors).

In a preferred embodiment of the invention, a transcription unit expressing a ribozyme that cleaves TNF-α RNA is inserted into a plasmid DNA vector or an adenovirus DNA viral vector. Both vectors have been used to transfer genes to the intact vasculature or to joints of live animals (Willard et al., 1992 *Circulation,* 86,1–473.; Nabel et al., 1990 *Science,* 249, 1285–1288) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of an injection catheter, stent or infusion pump or are directly added to cells or tissues ex vivo.

In another preferred embodiment of the invention, a transcription unit expressing a ribozyme that cleaves TNF-a RNA is inserted into a retrovirus vector for sustained expression of ribozyme(s).

EXAMPLE 1

TNF-α Hammerhead ribozymes

By engineering ribozyme motifs we have designed several ribozymes directed against TNF-α mRNA sequences. These ribozymes are synthesized with modifications that improve their nuclease resistance. The ability of ribozymes to cleave TNF-α target sequences in vitro is evaluated.

The ribozymes will be tested for function in cells by analyzing bacterial lipopolysaccharide (LPS)-induced TNF-α expression levels. Ribozymes will be delivered to cells by incorporation into liposomes, by complexing with cationic lipids, by microinjection, or by expression from DNA vectors. TNF-α expression will be monitored by ELISA, by indirect immunofluoresence, and/or by FACS analysis. TNF-α mRNA levels will be assessed by Northern analysis, RNAse protection, primer extension analysis or quantitative RT-PCR. Ribozymes that block the induction of TNF-α activity and/or TNF-α mRNA by more than 90% will be identified.

RNA ribozymes and/or genes encoding them will be locally delivered to macrophages by intraperitoneal injection. After a period of ribozyme uptake, the peritoneal macrophages are harvested and induced ex vivo with LPS. The ribozymes that significantly reduce TNF-α secretion are selected. The TNF-α can also be induced after ribozyme treatment with fixed Streptococcus in the peritoneal cavity instead of ex vivo. In this fashion the ability of TNF-α ribozymes to block TNF-α secretion in a localized inflammatory response are evaluated. In addition, we will determine if the ribozymes can block an ongoing inflammatory response by delivering the TNF-α ribozymes after induction by the injection of fixed Streptococcus.

To examine the effect of anti-TNF-α ribozymes on systemic inflammation, the ribozymes are delivered by intravenous injection. The ability of the ribozymes to inhibit TNF-α secretion and lethal shock caused by systemic LPS administration are assessed. Similarly, TNF-α ribozymes can be introduced into the joints of mice with collagen-induced arthritis. Either free delivery, liposome delivery, cationic lipid delivery, adeno-associated virus vector delivery, adenovirus vector delivery, retrovirus vector delivery or plasmid vector delivery in these animal model experiments can be used to supply ribozymes. One dose (or a few infrequent doses) of a stable anti-TNF-α ribozyme or a gene construct that constitutively expresses the ribozyme may abrogate tissue damage in these inflammatory diseases.

EXAMPLE 2

Targeting mouse TNF-α mRNA for cleavage by hairpin ribozymes

Design of Hairpin ribozymes:

As shown in FIG. 7, two hairpin ribozymes were designed to cleave two distinct sites (1393 and 1435) within the mouse TNF-α mRNA. Corresponding ribozymes were synthesized containing mutations in the catalytic core of the ribozyme which renders the ribozyme inactive (Berzal-Herranz et al., 1993 *EMBO J.* 12, 2567). To construct these ribozymes, partially overlapping top- and bottom-strand oligonucleotides (~50 nucleotides) were designed to include sequences for the T7 promoter and the hairpin ribozyme. The single-strand portions of annealed oligonucleotides were converted to double-strands using Sequenase (U.S. Biochemicals). Transcription reactions containing linear double-stranded templates were carried out essentially as described (Milligan & Uhlenbeck, 1989 supra) using the T7 mega shortscript kit (Ambion, Austin, Tex.).

Macrophage isolation.

To produce responsive macrophages 1 ml of sterile fluid thioglycollate broth (Difco, Detroit, Mich.) was injected i.p. into 6 week old female C57bl/6NCR mice 3 days before peritoneal lavage. Mice were maintained as specific pathogen free in autoclaved cages in a laminar flow hood and given sterilized water to minimize "spontaneous" activation of macrophages. The resulting peritoneal exudate cells (PEC) were obtained by lavage using Hanks balanced salt solution (HBSS) and were plated at $2.5 \times 10^5$/well in 96 well plates (Costar, Cambridge, Mass.) with Eagles minimal essential medium (EMEM) containing 10% heat inactivated fetal bovine serum. After adhering for 2 hours the wells were washed to remove non-adherent cells. The resulting cultures were 97% macrophages as determined by morphology and staining for non-specific esterase.

Transfection of ribozymes into macrophages:

The ribozymes were diluted to 2×final concentration, mixed with an equal volume of 11 nM lipofectamine (Life Technologies, Gaithersburg, Md.), and vortexed. 100 ml of lipid:ribozyme complex was then added directly to the cells, followed immediately by 10 ml fetal bovine serum. Three hours after ribozyme addition 100 ml of 1 mg/ml bacterial lipopolysaccaride (LPS) was added to each well to stimulate TNF production.

Quantitation of TNF-α in mouse macrophages:

Supernatants were sampled at 0, 2, 4, 8, and 24 hours post LPS stimulation and stored at −70° C. Quantitation of TNF-α was done by a specific ELISA. ELISA plates were coated with rabbit anti-mouse TNF-α serum at 1:1000 dilution (Genzyme) followed by blocking with milk proteins and incubation with TNF-α containing supernatants. TNF-α was then detected using a murine TNF-a specific hamster monoclonal antibody (Genzyme). The ELISA was developed with goat anti-hamster IgG coupled to alkaline phosphatase.

Assessment of reagent toxicity:

Following ribozyme/lipid treatment of macrophages and harvesting of supernatants viability of the cells was assessed by incubation of the cells with 5 mg/ml of 3-(4,5-dimethylthiazol-2-yl)-2,5-diphenyl tetrazolium bromide (MTT). This compound is reduced by the mitochondrial dihydrogenases, the activity of which correlates well with cell viability. After 12 hours the absorbance of reduced MTT is measured at 585 nm.

Inhibition of TNF-α expression by hairpin ribozymes in mouse macrophages:

As shown in FIGS. 8 and 9, expression of TNF-α is significantly inhibited by both hairpin ribozymes 1393 and 1435. The inhibition of TNF-α expression by the ribozyme 1435 (active) appears to be dependent on the catalytic activity of the ribozyme: a catalytically inactive hairpin ribozyme (1435 dead) does not show appreciable inhibition. In contrast, the inactive version of the 1393 ribozyme does show some inhibition of TNF-α expression at 162 nM ribozyme concentration. This inhibition may be attributed to ribozyme binding to the target sequence.

Sequences in FIG. 7 are non-limiting examples. Those in the art will recognize that these are but example, and other embodiments can be readily generated using techniques generally known in the art.

Uses

The association between TNF-α and bacterial sepsis, rheumatoid arthritis, and autoimmune disease make TNF-α an attractive target for therapeutic intervention [Tracy & Cerami 1992 supra; Williams et al., 1992 *Proc. Natl. Acad. Sci. USA* 89, 9784–9788; Jacob, 1992 *J. Autoimmun.* 5 (Supp. A), 133–143].

Septic Shock

Septic shock is a complication of major surgery, bacterial infection, and polytrauma characterized by high fever, increased cardiac output, reduced blood pressure and a neutrophilic infiltrate into the lungs and other major organs (Parrillo, 1993 supra). Current treatment options are limited to antibiotics to reduce the bacterial load and non-steroidal anti-inflammatories to reduce fever. Despite these treatments in the best intensive care settings, mortality from septic shock averages 50%, due primarily to multiple organ failure and disseminated vascular coagulation. Septic shock, with an incidence of 200,000 cases per year in the United States, is the major cause of death in intensive care units. In septic shock syndrome, tissue injury or bacterial products initiate massive immune activation, resulting in the secretion of pro-inflammatory cytokines which are not normally detected in the serum, such as TNF-α, interleukin-1β (IL-1β), γ-interferon (IFN-γ), interleukin-6 (IL-6), and interleukin-8 (IL-8). Other non-cytokine mediators such as leukotriene b4, prostaglandin E2, C3a and C3d also reach high levels (de Boer et al., 1992 *Immunopharmacology* 24, 135–148).

TNF-α is detected early in the course of septic shock in a large fraction of patients (de Boer et al., 1992 supra). In animal models, injection of TNF-α has been shown to induce shock-like symptoms similar to those induced by LPS injection (Beutler et al., 1985 *Science* 229, 869–871); in contrast, injection of IL-1β, IL-6, or IL-8 does not induce shock. Injection of TNF-α also causes an elevation of IL-1β, IL-6, IL-8, PgE$_2$, acute phase proteins, and TxA$_2$ in the serum of experimental animals (de Boer et al., 1992 supra). In animal models the lethal effects of LPS can be blocked by preadministration of anti-TNF-α antibodies. The cumulative evidence indicates that TNF-α is a key player in the pathogenesis of septic shock, and therefore a good candidate for therapeutic intervention.

Rheumatoid Arthritis

Rheumatoid arthritis (RA) is an autoimmune disease characterized by chronic inflammation of the joints leading to bone destruction and loss of joint function (Harris, 1990 supra). At the cellular level, autoreactive T-lymphocytes and monocytes are typically present, and the synoviocytes often have altered morphology and immunostaining patterns. RA joints have been shown to contain elevated levels of TNF-α, IL-1α and IL-1β, IL-6, GM-CSF, and TGF-β (Abney et al., 1991 *Imm. Rev.* 119, 105–123), some or all of which may contribute to the pathological course of the disease.

Cells cultured from RA joints spontaneously secrete all of the pro-inflammatory cytokines detected in vivo. Addition of antisera against TNF-α to these cultures has been shown to reduce IL-1α/β production by these cells to undetectable levels (Abney et al., 1991 Supra). Thus, TNF-α may directly induce the production of other cytokines in the RA joint. Addition of the anti-inflammatory cytokine, TGF-β, has no effect on cytokine secretion by RA cultures. Immunocytochemical studies of human RA surgical specimens clearly demonstrate the production of TNF-α, IL-1α/β, and IL-6 from macrophages near the cartilage/pannus junction when the pannus in invading and overgrowing the cartilage (Chu et al., 1992 *Br. J. Rheumatology* 31, 653–661). GM-CSF was shown to be produced mainly by vascular endothelium in these samples. Both TNF-α and TGF-β have been shown to be fibroblast growth factors, and may contribute to the accumulation of scar tissue in the RA joint. TNF-α has also been shown to increase osteoclast activity and bone resorbtion, and may have a role in the bone erosion commonly found in the RA joint (Cooper et al., 1992 *Clin. Exp. Immunol.* 89, 244–250).

Elimination of TNF-α from the rheumatic joint would be predicted to reduce overall inflammation by reducing induction of MHC class II, IL-1α/β, II-6, and GM-CSF, and reducing T-cell activation. Osteoclast activity might also fall, reducing the rate of bone erosion at the joint. Finally, elimination of TNF-α would be expected to reduce accumulation of scar tissue within the joint by removal of a fibroblast growth factor.

Treatment with an anti-TNF-a antibody reduces joint swelling and the histological severity of collagen-induced arthritis in mice (Williams et al., 1992 *Proc. Natl. Acad. Sci. USA* 89, 9784–9788). In addition, a study of RA patients who have received i.v. infusions of anti-TNF-α monoclonal antibody reports a reduction in the number and severity of inflamed joints after treatment. The benefit of monoclonal antibody treatment in the long term may be limited by the expense and immunogenicity of the antibody.

Psoriasis

Psoriasis is an inflammatory disorder of the skin characterized by keratinocyte hyperproliferation and immune cell infiltrate (Kupper, 1990 *J. Clin. Invest.* 86, 1783–1789). It is a fairly common condition, affecting 1.5–2.0% of the population. The disorder ranges in severity from mild, with small flaky patches of skin, to severe, involving inflammation of the entire epidermis. The cellular infiltrate of psoriasis includes T-lymphocytes, neutrophils, macrophages, and dermal dendrocytes. The majority of T-lymphocytes are activated CD4$^+$ cells of the T$_H$-1 phenotype, although some CD8$^+$ and CD4$^-$/CD8$^-$ are also present. B lymphocytes are typically not found in abundance in psoriatic plaques.

Numerous hypotheses have been offered as to the proximal cause of psoriasis including auto-antibodies and autoreactive T-cells, overproduction of growth factors, and genetic predisposition. Although there is evidence to support the involvement of each of these factors in psoriasis, they are neither mutually exclusive nor are any of them necessary and sufficient for the pathogenesis of psoriasis (Reeves, 1991 *Semin. Dermatol.* 10, 217).

The role of cytokines in the pathogenesis of psoriasis has been investigated. Among those cytokines found to be abnormally expressed were TGF-α, IL-1α, IL-1β, IL-1ra, IL-6, IL-8, IFN-γ, and TNF-α. In addition to abnormal cytokine production, elevated expression of ICAM-1, ELAM-1, and VCAM has been observed (Reeves, 1991 supra). This cytokine profile is similar to that of normal wound healing, with the notable exception that cytokine levels subside upon healing. Keratinocytes themselves have recently been shown to be capable of secreting EGF, TGF-α, IL-6, and TNF-α, which could increase proliferation in an autocrine fashion (Oxholm et al., 1991 *APMIS* 99, 58–64).

Nickoloff et al., 1993 (*J Dermatol Sci.* 6, 127–33) have proposed the following model for the initiation and maintenance of the psoriatic plaque:

Tissue damage induces the wound healing response in the skin. Keratinocytes secrete IL-1α, IL-1β, IL-6, IL-8, TNF-α. These factors activate the endothelium of dermal capillaries, recruiting PMNs, macrophages, and T-cells into the wound site.

Dermal dendrocytes near the dermal/epidermal junction remain activated when they should return to a quiescent state, and subsequently secrete cytokines including TNF-α, IL-6, and IL-8. Cytokine expression, in turn, maintains the activated state of the endothelium, allowing extravasation of additional immunocytes, and the activated state of the keratinocytes which secrete TGF-α and IL-8. Keratinocyte IL-8 recruits immunocytes from the dermis into the epidermis. During passage through the dermis, T-cells encounter the activated dermal dendrocytes which efficiently activate the $T_H$-1 phenotype. The activated T-cells continue to migrate into the epidermis, where they are stimulated by keratinocyte-expressed ICAM-1 and MHC class II. IFN-γ secreted by the T-cells synergizes with the TNF-α from dermal dendrocytes to increase keratinocyte proliferation and the levels of TGF-α, IL-8, and IL-6 production. IFN-γ also feeds back to the dermal dendrocyte, maintaining the activated phenotype and the inflammatory cycle.

Elevated serum titres of IL-6 increases synthesis of acute phase proteins including complement factors by the liver, and antibody production by plasma cells. Increased complement and antibody levels increases the probability of autoimmune reactions.

Maintenance of the psoriatic plaque requires continued expression of all of these processes, but attractive points of therapeutic intervention are TNF-α expression by the dermal dendrocyte to maintain activated endothelium and keratinocytes, and IFN-γ expression by T-cells to maintain activated dermal dendrocytes.

There are 3 million patients in the United States afflicted with psoriasis. The available treatments for psoriasis are corticosteroids. The most widely prescribed are TEMO-VATE (clobetasol propionate), LIDEX (fluocinonide), DIPROLENE (betamethasone propionate), PSORCON (diflorasone diacetate) and TRIAMCINOLONE formulated for topical application. The mechanism of action of corticosteroids is multifactorial. This is a palliative therapy because the underlying cause of the disease remains, and upon discontinuation of the treatment the disease returns. Discontinuation of treatment is often prompted by the appearance of adverse effects such as atrophy, telangiectasias and purpura. Corticosteroids are not recommended for prolonged treatments or when treatment of large and/or inflamed areas is required. Alternative treatments include retinoids, such as etretinate, which has been approved for treatment of severe, refractory psoriasis. Alternative retinoid-based treatments are in advanced clinical trials. Retinoids act by converting keratinocytes to a differentiated state and restoration of normal skin development. Immunosuppressive drugs such as cyclosporine are also in the advanced stages of clinical trials. Due to the nonspecific mechanism of action of corticosteroids, retinoids and immunosuppressives, these treatments exhibit severe side effects and should not be used for extended periods of time unless the condition is life-threatening or disabling. There is a need for a less toxic, effective therapeutic agent in psoriatic patients.

HIV and AIDS

The human immunodeficiency virus (HIV) causes several fundamental changes in the human immune system from the time of infection until the development of full-blown acquired immunodeficiency syndrome (AIDS). These changes include a shift in the ratio of CD4+ to CD8+ T-cells, sustained elevation of IL-4 levels, episodic elevation of TNF-α and TNF-β levels, hypergammaglobulinemia, and lymphoma/leukemia (Rosenberg & Fauci, 1990 *Immun. Today* 11, 176; Weiss 1993 *Science* 260, 1273). Many patients experience a unique tumor, Kaposi's sarcoma and/or unusual opportunistic infections (e.g. *Pneumocystis carinii*, cytomegalovirus, herpesviruses, hepatitis viruses, papilloma viruses, and tuberculosis). The immunological dysfunction of individuals with AIDS suggests that some of the pathology may be due to cytokine dysregulation.

Levels of serum TNF-α and IL-6 are often found to be elevated in AIDS patients (Weiss, 1993 supra). In tissue culture, HIV infection of monocytes isolated from healthy individuals stimulates secretion of both TNF-α and IL-6. This response has been reproduced using purified gp120, the viral coat protein responsible for binding to CD-4 (Buonaguro et al., 1992 *J. Virol.* 66, 7159). It has also been demonstrated that the viral gene regulator, Tat, can directly induce TNF transcription. The ability of HIV to directly stimulate secretion of TNF-α and IL-6 may be an adaptive mechanism of the virus. TNF-α has been shown to upregulate transcription of the LTR of HIV, increasing the number of HIV-specific transcripts in infected cells. IL-6 enhances HIV production, but at a post-transcriptional level, apparently increasing the efficiency with which HIV transcripts are translated into protein. Thus, stimulation of TNF-α secretion by the HIV virus may promote infection of neighboring CD4+ cells both by enhancing virus production from latently infected cells and by driving replication of the virus in newly infected cells.

The role of TNF-α in HIV replication has been well established in tissue culture models of infection (Sher et al., 1992 *Immun. Rev.* 127, 183), suggesting that the mutual induction of HIV replication and TNF-α replication may create positive feedback in vivo. However, evidence for the presence of such positive feedback in infected patients is not abundant. TNF-α levels are found to be elevated in some, but not all patients tested. Children with AIDS who were given zidovudine had reduced levels of TNF-α compared to those not given zidovudine (Cremoni et al., 1993 *AIDS* 7, 128). This correlation lends support to the hypothesis that reduced viral replication is physiologically linked to TNF-α levels. Furthermore, recently it has been shown that the polyclonal B cell activation associated with HIV infection is due to membrane-bound TNF-α. Thus, levels of secreted TNF-α may not accurately reflect the contribution of this cytokine to AIDS pathogenesis.

Chronic elevation of TNF-α has been shown to shown to result in cachexia (Tracey et al., 1992 *Am. J. Trop. Med. Hyg.* 47, 2–7), increased autoimmune disease (Jacob, 1992 supra), lethargy, and immune suppression in animal models (Aderka et al., 1992 *Isr. J. Med. Sci.* 28, 126–130). The cachexia associated with AIDS may be associated with chronically elevated TNF-α frequently observed in AIDS patients. Similarly, TNF-α can stimulate the proliferation of spindle cells isolated from Kaposi's sarcoma lesions of AIDS patients (Barillari et al., 1992 *J Immunol* 149, 3727).

A therapeutic agent that inhibits cytokine gene expression, inhibits adhesion molecule expression, and mimics the anti-inflammatory effects of glucocorticoids (without inducing steroid-responsive genes) is ideal for the treatment of inflammatory and autoimmune disorders. Disease targets for such a drug are numerous. Target indications and the delivery options each entails are summarized below. In all cases, because of the potential immunosuppressive properties of a ribozyme that cleaves the specified sites in TNF-α mRNA, uses are limited to local delivery, acute indications, or ex vivo treatment.

●Septic shock.

Exogenous delivery of ribozymes to macrophages can be achieved by intraperitoneal or intravenous injections. Ribozymes will be delivered by incorporation into liposomes or by complexing with cationic lipids.

●Rheumatoid arthritis (RA).

Due to the chronic nature of RA, a gene therapy approach is logical. Delivery of a ribozyme to inflamed joints is mediated by adenovirus, retrovirus, or adeno-associated virus vectors. For instance, the appropriate adenovirus vector can be administered by direct injection into the synovium: high efficiency of gene transfer and expression for several months would be expected (B. J. Roessler, E. D. Allen, J. M. Wilson, J. W. Hartman, B. L. Davidson, J. Clin. Invest. 92, 1085–1092 (1993)). It is unlikely that the course of the disease could be reversed by the transient, local administration of an anti-inflammatory agent. Multiple administrations may be necessary. Retrovirus and adeno-associated virus vectors would lead to permanent gene transfer and expression in the joint. However, permanent expression of a potent anti-inflammatory agent may lead to local immune deficiency.

●Psoriasis

The psoriatic plaque is a particularly good candidate for ribozyme or vector delivery. The stratum corneum of the plaque is thinned, providing access to the proliferating keratinocytes. T-cells and dermal dendrocytes can be efficiently targeted by trans-epidermal diffusion.

Organ culture systems for biopsy specimens of psoriatic and normal skin are described in current literature (Nickoloff et al., 1993 Supra). Primary human keratinocytes are easily obtained and will be grown into epidermal sheets in tissue culture. In addition to these tissue culture models, the flaky skin mouse develops psoriatic skin in response to UV light. This model would allow demonstration of animal efficacy for ribozyme treatments of psoriasis.

●Gene Therapy.

Immune responses limit the efficacy of many gene transfer techniques. Cells transfected with retrovirus vectors have short lifetimes in immune competent individuals. The length of expression of adenovirus vectors in terminally differentiated cells is longer in neonatal or immune-compromised animals. Insertion of a small ribozyme expression cassette that modulates inflammatory and immune responses into existing adenovirus or retrovirus constructs will greatly enhance their potential.

Thus, ribozymes of the present invention that cleave TNF-α mRNA and thereby TNF-α activity have many potential therapeutic uses, and there are reasonable modes of delivering the ribozymes in a number of the possible indications. Development of an effective ribozyme that inhibits TNF-α function is described above; available cellular and activity assays are number, reproducible, and accurate. Animal models for TNF-α function and for each of the suggested disease targets exist and can be used to optimize activity.

Diagnostic uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with a TNF-α related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., TNF-α) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

A number of other cytokines may also be involved in the activation of inflammation, including platelet activating factor, IL-1, IL-3, IL-4, GM-CSF, gamma interferon, ILAM-1, ELAM-1 and EoCSF. In addition to these cytokines, it is appreciated that any cellular receptors which mediate the activities of the cytokines are also good targets for intervention in inflammatory diseases. These targets include, but are not limited to, the IL-1R and TNF-αR on keratinocytes, epithelial and endothelial cells in airways. Recent data suggest that certain neuropeptides may play a role in asthmatic symptoms. These peptides include substance P, neurokinin A and calcitonin-gene-related peptides. These target genes may have more general roles in inflammatory diseases, but are currently assumed to have a role only in asthma. Other genes which are considered to play a role in asthma are the c-myb and c-myc genes, which may be triggered to induce endothelial cell proliferation and contribute to blockage of the airways. Those skilled in the art will recognize the other potential targets noted above are also suitable for treatment with ribozymes, which will reduce the risk or occurrence of inflammatory disease, such as the interleukins (1, 3, 4, 6, and 8), glycerol transferase, selectins (E-selectin, MEL-14), cell adhesion molecules (ICAM-1, ELAM-1, VCAM-1, GMP-140, MAM), IL-1R, TGFβ R, EoCSF,α-, β- or γ-interferon, EoCSF, GM-CSF and protein kinase C (PKC)

Other embodiments are within the following claims.

TABLE I

Characteristics of Ribozymes

Group I Introns Size: ~200 to >1000 nucleotides. Requires a U in the target sequence immediately 5' of the cleavage site. Binds 4–6 nucleotides at 5' side of cleavage site. Over 75 known members of this class. Found in *Tetrahymena thermophila* rRNA, fungal mitochondria, chloroplasts, phage T4, blue-green algae, and others.

RNAseP RNA (M1 RNA) Size: ~290 to 400 nucleotides. RNA portion of a ribonucleoprotein enzyme. Cleaves tRNA precursors to form mature tRNA. Roughly 10 known members of this group all are bacterial in origin.

Hammerhead Ribozyme Size: ~13 to 40 nucleotides. Requires the target sequence UH immediately 5' of the cleavage site. Binds a variable number nucleotides on both sides of the cleavage site. 14 known members of this class. Found in a number of plant pathogens (virusoids) that use RNA as the infectious agent (FIGS. 1 and 2)

Figure 3:
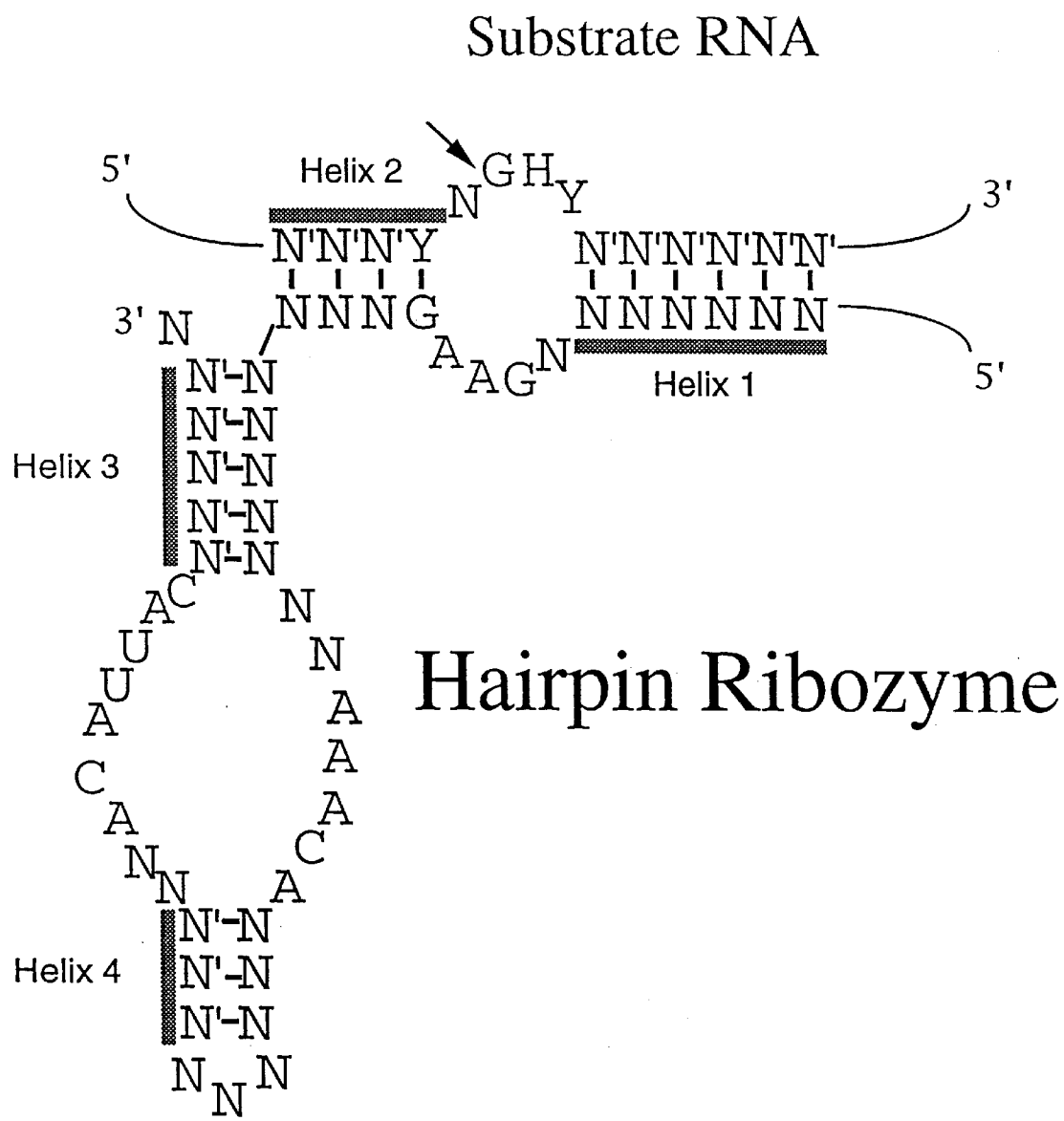

Hairpin Ribozyme Size: ~50 nucleotides. Requires the target sequence GUC immediately 3' of the cleavage site. Binds 4–6 nucleotides at 5' side of the cleavage site and a variable number to the 3' side of the cleavage site. Only 3 known member of this class. Found in three plant pathogen (satellite RNAs of the tobacco ringspot virus, arabis mosaic virus and chicory yellow mottle virus) which uses RNA as the infectious agent (FIG. 3).

Figure 4:
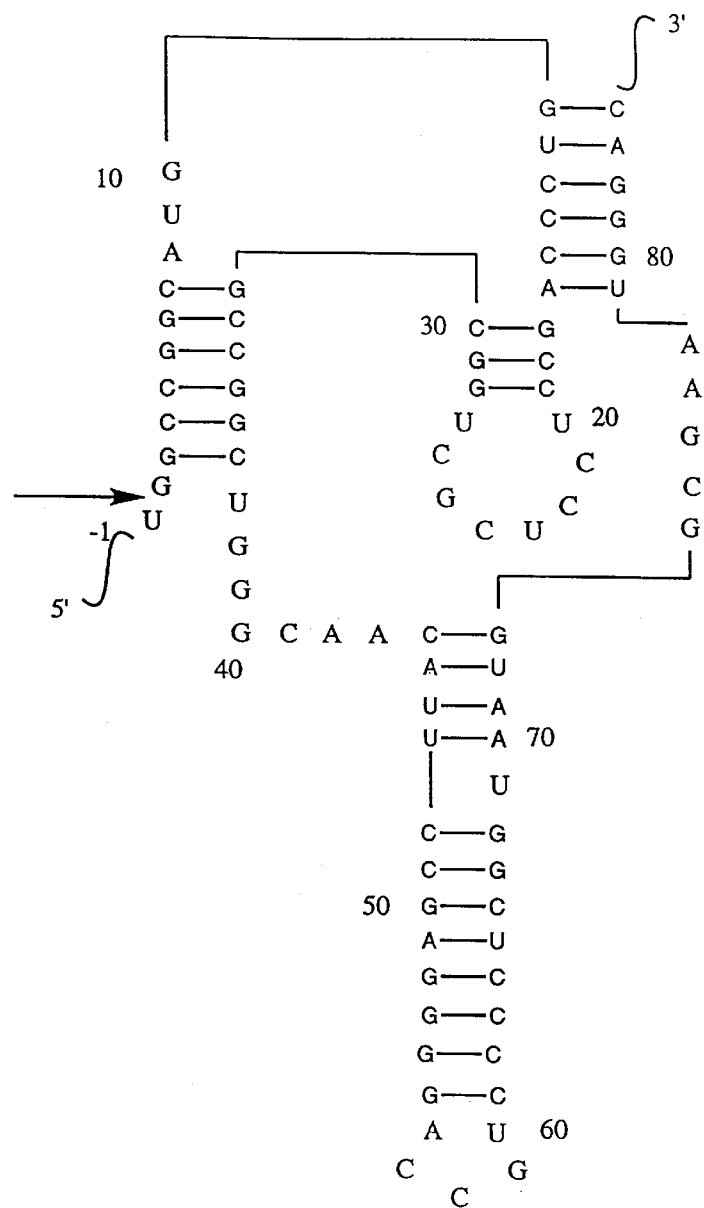
FIG. 4 is a representation of the general structure of the hepatitis delta virus ribozyme domain known in the art.

Hepatitis Delta Virus (HDV) Ribozyme Size: 50–60 nucleotides (at present). Cleavage of target RNAs recently demonstrated. Sequence requirements not fully determined. Binding sites and structural requirements not fully determined, although no sequences 5' of cleavage site are required. Only 1 known member of this class. Found in human HDV (FIG. 4).

Figure 5:
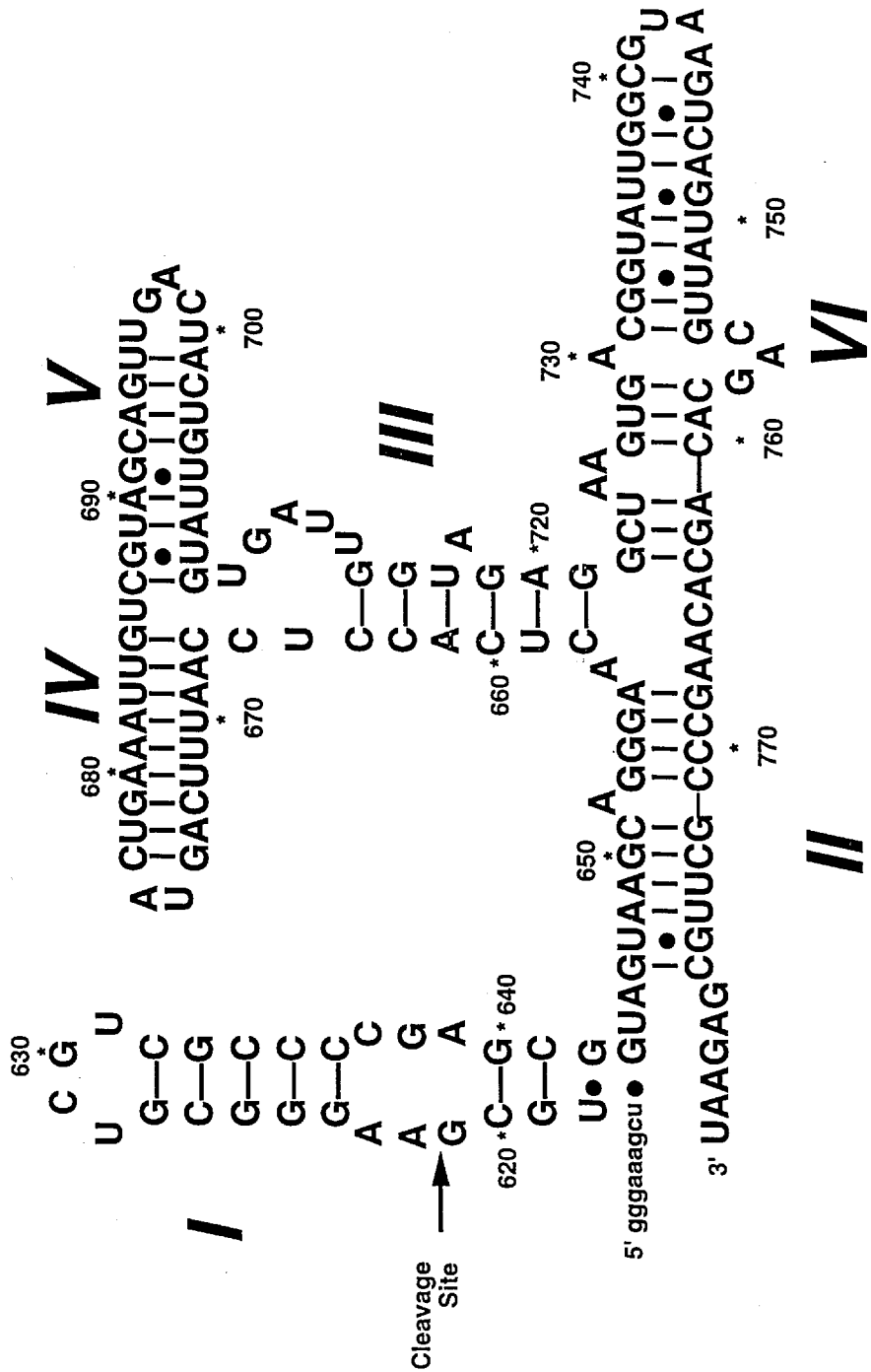
FIG. 5 is a representation of the general structure of the VS RNA ribozyme domain.

Neurospora VS RNA Ribozyme Size: ~144 nucleotides (at present) Cleavage of target RNAs recently demonstrated. Sequence requirements not fully determined. Binding sites and structural requirements not fully determined. Only 1 known member of this class. Found in Neurospora VS RNA (FIG. 5).

TABLE II

Human TNF-a HH Ribozyme Target Sequence

| nt. Position | HH Target Sequence | Sequence ID No. | nt. Position | HH Target Sequence | Sequence ID No. |
|---|---|---|---|---|---|
| 28 | GGCAGGU U CUCUUCC | 15 | | | |
| 29 | GCAGGUU C UCUUCCU | 16 | 321 | GUCAGAU C AUCUUCU | 54 |
| 31 | AGGUUCU C UUCCUCU | 17 | 324 | AGAUCAU C UUCUCGA | 55 |
| 33 | GUUCUCU U CCUCUCA | 18 | 326 | AUCAUCU U CUCGAAC | 56 |
| 34 | UUCUCUU C CUCUCAC | 19 | 327 | UCAUCUU C UCGAACC | 57 |
| 37 | UCUUCCU C UCACAUA | 20 | 329 | AUCUUCU C GAACCCC | 58 |
| 39 | UUCCUCU C ACAUACU | 21 | 352 | AGCCUGU A GCCCAUG | 59 |
| 44 | CUCACAU A CUGACCC | 22 | 361 | CCCAUGU U GUAGCAA | 60 |
| 58 | CACGGCU C CACCCUC | 23 | 364 | AUGUUGU A GCAAACC | 61 |
| 65 | CCACCCU C UCUCCCC | 24 | 374 | AAACCCU C AAGCUGA | 62 |
| 67 | ACCCUCU C UCCCCUG | 25 | 391 | GGCAGCU C CAGUGGC | 63 |
| 69 | CCUCUCU C CCCUGGA | 26 | 421 | AUGCCCU C CUGGCCA | 64 |
| 106 | GCAUGAU C CGGGACG | 27 | 449 | GAGAGAU A ACCAGCU | 65 |
| 136 | AGGCGCU C CCCAAGA | 28 | 468 | GUGCCAU C AGAGGGC | 66 |
| 165 | CAGGGCU C CAGGCGG | 29 | 480 | GGCCUGU A CCUCAUC | 67 |
| 177 | CGGUGCU U GUUCCUC | 30 | 484 | UGUACCU C AUCUACU | 68 |
| 180 | UGCUUGU U CCUCAGC | 31 | 487 | ACCUCAU C UACUCCC | 69 |
| 181 | GCUUGUU C CUCAGCC | 32 | 489 | CUCAUCU A CUCCCAG | 70 |
| 184 | UGUUCCU C AGCCUCU | 33 | 492 | AUCUACU C CCAGGUC | 71 |
| 190 | UCAGCCU C UUCUCCU | 34 | 499 | CCCAGGU C CUCUUCA | 72 |
| 192 | AGCCUCU U CUCCUUC | 35 | 502 | AGGUCCU C UUCAAGG | 73 |
| 193 | GCCUCUU C UCCUUCC | 36 | 504 | GUCCUCU U CAAGGGC | 74 |
| 195 | CUCUUCU C CUUCCUG | 37 | 505 | UCCUCUU C AAGGGCC | 75 |
| 198 | UUCUCCU U CCUGAUC | 38 | 525 | UGCCCCU C CACCCAU | 76 |
| 199 | UCUCCUU C CUGAUCG | 39 | 538 | AUGUGCU C CUCACCC | 77 |
| 205 | UCCGAUC C GUGGCAG | 40 | 541 | UGCUCCU C ACCCACA | 78 |
| 226 | CCACGCU C UUCUGCC | 41 | 553 | ACACCAU C AGCCGCA | 79 |
| 228 | ACGCUCU U CUGCCUG | 42 | 562 | GCCGCAU C GCCGUCU | 80 |
| 229 | CGCUCUU C UGCCUGC | 43 | 568 | UCGCCGU C UCCUACC | 81 |
| 243 | CUGCACU U GGAGUG | 44 | 570 | GCCGUCU C CUACCAG | 82 |
| 244 | UGCACUU U GGAGUGA | 45 | 573 | GUCUCCU A CCAGACC | 83 |
| 253 | GAGUGAU C GGCCCCC | 46 | 586 | CCAAGGU C AACCUCC | 84 |
| 273 | GAAGAGU C CCCCAGG | 47 | 592 | UCAACCU C CUCUCUG | 85 |
| 286 | GGGACCU C UCUCUAA | 48 | 595 | ACCUCCU C UCUGCCA | 86 |
| 288 | GACCUCU C UCUAAUC | 49 | 597 | CUCCUCU C UGCCAUC | 87 |
| 290 | CCUCUCU C UAAUCAG | 50 | 604 | CUGCCAU C AAGAGCC | 88 |
| 292 | UCUCUCU A AUCAGCC | 51 | 657 | CCCUGGU A UGAGCCC | 89 |
| 295 | CUCUAAU C AGCCCUC | 52 | 667 | AGCCCAU C UAUCUGG | 90 |
| 302 | CAGCCCU C UGGCCCA | 53 | 669 | CCCAUCU A UCUGGGA | 91 |
| 671 | CAUCUAU C UGGGAGG | 92 | 960 | UGGGAUU C AGGAAUG | 141 |
| 682 | GAGGGGU C UUCCAGC | 93 | 1001 | AACCACU A AGAAUUC | 142 |
| 684 | GGGGUCU U CCAGCUG | 94 | 1007 | UAAGAAU U CAAACUG | 143 |
| 685 | GGGUCUU C CAGCUGG | 95 | 1008 | AAGAAUU C AAACUGG | 144 |
| 709 | ACCGACU C AGCGCUG | 96 | 1021 | GGGGCCU C CAGAACU | 145 |
| 721 | CUGAGAU C AAUCGGC | 97 | 1029 | CAGAACU C ACUGGGG | 146 |

TABLE II-continued

Human TNF-a HH Ribozyme Target Sequence

| nt.

TABLE II-continued

Human TNF-a HH Ribozyme Target Sequence

| nt. Position | HH Target Sequence | Sequence ID No. | nt. Position | HH Target Sequence | Sequence ID No. |
|---|---|---|---|---|---|
| 1361 | CAUGUUU U CCGUGAA | 221 | | | |
| 1362 | AUGUUUU C CGUGAAA | 222 | | | |
| 1386 | GAACAAU A GGCUGUU | 223 | | | |
| 1393 | AGGCUGU U CCCAUGU | 224 | | | |
| 1394 | GGCUGUU C CCAUGUA | 225 | | | |
| 1401 | CCCAUGU A GCCCCCU | 226 | | | |
| 1414 | CUGGCCU C UGUGCCU | 227 | | | |
| 1422 | UGUGCCU U CUUUUGA | 228 | | | |
| 1423 | GUGCCUU C UUUUGAU | 229 | | | |
| 1425 | GCCUUCU U UUGAUUA | 230 | | | |
| 1426 | CCUUCUU U UGAUUAU | 231 | | | |
| 1427 | CUUCUUU U GAUUAUG | 232 | | | |
| 1431 | UUUUGAU U AUGUUUU | 233 | | | |
| 1432 | UUUGAUU A UGUUUUU | 234 | | | |
| 1436 | AUUAUGU U UUUUAAA | 235 | | | |
| 1437 | UUAUGUU U UUUAAAA | 236 | | | |
| 1438 | UAUGUUU U UUAAAAU | 237 | | | |

TABLE III

Human TNF-a Hammerhead Ribozyme Sequences

| nt. Position | HH Ribozyme Sequence | Sequence ID No. |
|---|---|---|
| 28 | GGAAGAG CUGAUGAGGCCGAAAGGCCGAA ACCUGCC | 268 |
| 29 | AGGAAGA CUGAUGAGGCCGAAAGGCCGAA AACCUGC | 269 |
| 31 | AGAGGAA CUGAUGAGGCCGAAAGGCCGAA AGAACCU | 270 |
| 33 | UGAGAGG CUGAUGAGGCCGAAAGGCCGAA AGAGAAC | 271 |
| 34 | GUGAGAG CUGAUGAGGCCGAAAGGCCGAA AAGAGAA | 271 |
| 37 | UAUGUGA CUGAUGAGGCCGAAAGGCCGAA AGGAAGA | 273 |
| 39 | AGUAUGU CUGAUGAGGCCGAAAGGCCGAA AGAGGAA | 274 |
| 44 | GGGUCAG CUGAUGAGGCCGAAAGGCCGAA AUGUGAG | 275 |
| 58 | GAGGGUG CUGAUGAGGCCGAAAGGCCGAA AGCCGUG | 276 |
| 65 | GGGGAGA CUGAUGAGGCCGAAAGGCCGAA AGGGUGG | 277 |
| 67 | CAGGGGA CUGAUGAGGCCGAAAGGCCGAA AGAGGGU | 278 |
| 69 | UCCAGGG CUGAUGAGGCCGAAAGGCCGAA AGAGAGG | 279 |
| 106 | CGUCCCG CUGAUGAGGCCGAAAGGCCGAA AUCAUGC | 280 |
| 136 | UCUUGGG CUGAUGAGGCCGAAAGGCCGAA AGCGCCU | 281 |
| 165 | CCGCCUG CUGAUGAGGCCGAAAGGCCGAA AGCCCUG | 282 |
| 177 | GAGGAAC CUGAUGAGGCCGAAAGGCCGAA AGCACCG | 283 |
| 180 | GCUGAGG CUGAUGAGGCCGAAAGGCCGAA ACAAGCA | 284 |
| 181 | GGCUGAG CUGAUGAGGCCGAAAGGCCGAA AACAAGC | 285 |
| 184 | AGAGGCU CUGAUGAGGCCGAAAGGCCGAA AGGAACA | 286 |
| 190 | AGGAGAA CUGAUGAGGCCGAAAGGCCGAA AGGCUGA | 287 |
| 192 | GAAGGAG CUGAUGAGGCCGAAAGGCCGAA AGAGGCU | 288 |
| 193 | GGAAGGA CUGAUGAGGCCGAAAGGCCGAA AAGAGGC | 289 |
| 195 | CAGGAAG CUGAUGAGGCCGAAAGGCCGAA AGAAGAG | 290 |
| 198 | GAUCAGG CUGAUGAGGCCGAAAGGCCGAA AGGAGAA | 291 |
| 199 | CGAUCAG CUGAUGAGGCCGAAAGGCCGAA AAGGAGA | 292 |
| 205 | CUGCCAC CUGAUGAGGCCGAAAGGCCGAA AUCAGGA | 293 |
| 226 | GCCAGAA CUGAUGAGGCCGAAAGGCCGAA AGCGUGG | 294 |
| 228 | CAGGCAG CUGAUGAGGCCGAAAGGCCGAA AGAGCGU | 295 |
| 229 | GCAGGCA CUGAUGAGGCCGAAAGGCCGAA AAGAGCG | 296 |
| 243 | CACUCCA CUGAUGAGGCCGAAAGGCCGAA AGUGCAG | 297 |
| 244 | UCACUCC CUGAUGAGGCCGAAAGGCCGAA AAGUGCA | 298 |
| 253 | GGGGGCC CUGAUGAGGCCGAAAGGCCGAA AUCACUC | 299 |
| 273 | CCUGGGG CUGAUGAGGCCGAAAGGCCGAA ACUCUUC | 300 |
| 286 | UUAGAGA CUGAUGAGGCCGAAAGGCCGAA AGGUCCC | 301 |
| 288 | GAUUAGA CUGAUGAGGCCGAAAGGCCGAA AGAGGUC | 302 |
| 290 | CUGAUUA CUGAUGAGGCCGAAAGGCCGAA AGAGAGG | 303 |
| 292 | GGCUGAU CUGAUGAGGCCGAAAGGCCGAA AGAGAGA | 304 |
| 295 | GAGGGCU CUGAUGAGGCCGAAAGGCCGAA AUUAGAG | 305 |
| 302 | UGGGCCA CUGAUGAGGCCGAAAGGCCGAA AGGGCUG | 306 |
| 321 | AGAAGAU CUGAUGAGGCCGAAAGGCCGAA AUCUGAC | 307 |
| 324 | UCGAGAA CUGAUGAGGCCGAAAGGCCGAA AUGAUCU | 308 |
| 326 | GUUCGAG CUGAUGAGGCCGAAAGGCCGAA AGAUGAU | 309 |
| 327 | GGUUCGA CUGAUGAGGCCGAAAGGCCGAA AAGAUGA | 310 |
| 329 | GGGGUUC CUGAUGAGGCCGAAAGGCCGAA AGAAGAU | 311 |
| 352 | CAUGGGC CUGAUGAGGCCGAAAGGCCGAA ACAGGCU | 312 |
| 361 | UUGCUAC CUGAUGAGGCCGAAAGGCCGAA ACAUGGG | 313 |

TABLE III-continued

Human TNF-a Hammerhead Ribozyme Sequences

| nt. Position | HH Ribozyme Sequence | Sequence ID No. |
|---|---|---|
| 364 | GGUUUGC CUGAUGAGGCCGAAAGGCCGAA ACAACAU | 314 |
| 374 | UCAGCUU CUGAUGAGGCCGAAAGGCCGAA AGGGUUU | 315 |
| 391 | GCCACUG CUGAUGAGGCCGAAAGGCCGAA AGCUGCC | 316 |
| 421 | UGGCCAG CUGAUGAGGCCGAAAGGCCGAA AGGGCAU | 317 |
| 449 | AGCUGGU CUGAUGAGGCCGAAAGGCCGAA AUCUCUC | 318 |
| 468 | GCCCUCU CUGAUGAGGCCGAAAGGCCGAA AUGGCAC | 319 |
| 480 | GAUGAGG CUGAUGAGGCCGAAAGGCCGAA ACAGGCC | 320 |
| 484 | AGUAGAU CUGAUGAGGCCGAAAGGCCGAA AGGUACA | 321 |
| 487 | GGGAGUA CUGAUGAGGCCGAAAGGCCGAA AUGAGGU | 322 |
| 489 | CUGGGAG CUGAUGAGGCCGAAAGGCCGAA AGAUGAG | 323 |
| 492 | GACCUGG CUGAUGAGGCCGAAAGGCCGAA AGUAGAU | 324 |
| 499 | UGAAGAG CUGAUGAGGCCGAAAGGCCGAA ACCUGGG | 325 |
| 502 | CCUUGAA CUGAUGAGGCCGAAAGGCCGAA AGGACCU | 326 |
| 504 | GCCCUUG CUGAUGAGGCCGAAAGGCCGAA AGAGGAC | 327 |
| 505 | GGCCCUU CUGAUGAGGCCGAAAGGCCGAA AAGAGGA | 328 |
| 525 | AUGGGUG CUGAUGAGGCCGAAAGGCCGAA AGGGGCA | 329 |
| 538 | GGGUGAG CUGAUGAGGCCGAAAGGCCGAA AGCACAU | 330 |
| 541 | UGUGGGU CUGAUGAGGCCGAAAGGCCGAA AGGAGCA | 331 |
| 553 | UGCCGCU CUGAUGAGGCCGAAAGGCCGAA AUGGUGU | 332 |
| 562 | AGACGGC CUGAUGAGGCCGAAAGGCCGAA AUGCGGC | 333 |
| 568 | GGUAGGA CUGAUGAGGCCGAAAGGCCGAA ACGGCGA | 334 |
| 570 | CUGGUAG CUGAUGAGGCCGAAAGGCCGAA AGACGGC | 335 |
| 573 | GGUCUGG CUGAUGAGGCCGAAAGGCCGAA AGGAGAC | 336 |
| 586 | GGAGGUU CUGAUGAGGCCGAAAGGCCGAA ACCUUGG | 337 |
| 592 | CAGAGAG CUGAUGAGGCCGAAAGGCCGAA AGGUUGA | 338 |
| 595 | UGGCAGA CUGAUGAGGCCGAAAGGCCGAA AGGAGGU | 339 |
| 597 | GAUGGCA CUGAUGAGGCCGAAAGGCCGAA AGAGGAG | 340 |
| 604 | GGCUCUU CUGAUGAGGCCGAAAGGCCGAA AUGGCAG | 341 |
| 657 | GGGCUCA CUGAUGAGGCCGAAAGGCCGAA ACCAGGG | 342 |
| 667 | CCAGAUA CUGAUGAGGCCGAAAGGCCGAA AUGGGCU | 343 |
| 669 | UCCCAGA CUGAUGAGGCCGAAAGGCCGAA AGAUGGG | 344 |
| 671 | CCUCCCA CUGAUGAGGCCGAAAGGCCGAA AUAGAUG | 345 |
| 682 | GCUGGAA CUGAUGAGGCCGAAAGGCCGAA ACCCCUC | 346 |
| 684 | CAGCUGG CUGAUGAGGCCGAAAGGCCGAA AGACCCC | 347 |
| 685 | CCAGCUG CUGAUGAGGCCGAAAGGCCGAA AAGACCC | 348 |
| 709 | CAGCGCU CUGAUGAGGCCGAAAGGCCGAA AGUCGGU | 349 |
| 721 | GCCGAUU CUGAUGAGGCCGAAAGGCCGAA AUCUCAG | 350 |
| 725 | UCGGGCC CUGAUGAGGCCGAAAGGCCGAA AUUGAUC | 351 |
| 735 | GUCGAGA CUGAUGAGGCCGAAAGGCCGAA AGUCGGG | 352 |
| 737 | AAGUCGA CUGAUGAGGCCGAAAGGCCGAA AUAGUCG | 353 |
| 739 | CAAAGUC CUGAUGAGGCCGAAAGGCCGAA AGAUAGU | 354 |
| 744 | CUCGGCA CUGAUGAGGCCGAAAGGCCGAA AGUCGAG | 355 |
| 745 | ACUCGGC CUGAUGAGGCCGAAAGGCCGAA AAGUCGA | 356 |
| 753 | CUGCCCA CUGAUGAGGCCGAAAGGCCGAA ACUCGGC | 357 |
| 763 | CAAAGUA CUGAUGAGGCCGAAAGGCCGAA ACCUGCC | 358 |
| 765 | CCCAAAG CUGAUGAGGCCGAAAGGCCGAA AGACCUG | 359 |
| 768 | GAUCCCA CUGAUGAGGCCGAAAGGCCGAA AGUAGAC | 360 |
| 769 | UGAUCCC CUGAUGAGGCCGAAAGGCCGAA AAGUAGA | 361 |
| 775 | GGGCAAU CUGAUGAGGCCGAAAGGCCGAA AUCCCAA | 362 |
| 778 | ACAGGGC CUGAUGAGGCCGAAAGGCCGAA AUGAUCC | 363 |
| 801 | AAGGUUG CUGAUGAGGCCGAAAGGCCGAA AUGUUCG | 364 |
| 808 | GUUUGGG CUGAUGAGGCCGAAAGGCCGAA AGGUUGG | 365 |
| 809 | CGUUUGG CUGAUGAGGCCGAAAGGCCGAA AAGGUUG | 366 |
| 820 | GGCAGGG CUGAUGAGGCCGAAAGGCCGAA AGGCGUU | 367 |
| 833 | AUAAAGG CUGAUGAGGCCGAAAGGCCGAA AUUGGGG | 368 |
| 837 | GGUAAUA CUGAUGAGGCCGAAAGGCCGAA AGGGAUU | 369 |
| 838 | GGGUAAU CUGAUGAGGCCGAAAGGCCGAA AAGGGAU | 370 |
| 839 | GGGGUAA CUGAUGAGGCCGAAAGGCCGAA AAAGGGA | 371 |
| 841 | AGGGGGU CUGAUGAGGCCGAAAGGCCGAA AUAAAGG | 372 |
| 842 | GAGGGGG CUGAUGAGGCCGAAAGGCCGAA AAUAAAG | 373 |
| 849 | UCUGAAG CUGAUGAGGCCGAAAGGCCGAA AGGGGGU | 374 |
| 852 | GUGUCUG CUGAUGAGGCCGAAAGGCCGAA AGGAGGG | 375 |
| 853 | GGUGUCU CUGAUGAGGCCGAAAGGCCGAA AAGGAGG | 376 |
| 863 | AGAGGUU CUGAUGAGGCCGAAAGGCCGAA AGGGUGU | 377 |
| 869 | GCCAGAA CUGAUGAGGCCGAAAGGCCGAA AGGUUGA | 378 |
| 871 | GAGCCAG CUGAUGAGGCCGAAAGGCCGAA AGAGGUU | 379 |
| 872 | UGAGCCA CUGAUGAGGCCGAAAGGCCGAA AAGAGGU | 380 |
| 878 | UCUUUUU CUGAUGAGGCCGAAAGGCCGAA AGCCAGA | 381 |
| 890 | AGCCCCC CUGAUGAGGCCGAAAGGCCGAA AUUCUCU | 382 |
| 898 | CGACCCU CUGAUGAGGCCGAAAGGCCGAA AGCCCCC | 383 |
| 899 | CCGACCC CUGAUGAGGCCGAAAGGCCGAA AAGCCCC | 384 |
| 904 | GGGUUCC CUGAUGAGGCCGAAAGGCCGAA ACCCUAA | 385 |
| 917 | AAGUUCU CUGAUGAGGCCGAAAGGCCGAA AGCUUGG | 386 |
| 918 | AAAGUUC CUGAUGAGGCCGAAAGGCCGAA AAGCUUG | 387 |

TABLE III-continued

Human TNF-a Hammerhead Ribozyme Sequences

| nt. Position | HH Ribozyme Sequence | Sequence ID No. |
|---|---|---|
| 924 | UUGCUUA CUGAUGAGGCCGAAAGGCCGAA AGUUCUA | 388 |
| 925 | GUUGCUU CUGAUGAGGCCGAAAGGCCGAA AAGUUCU | 389 |
| 926 | UGUUGCU CUGAUGAGGCCGAAAGGCCGAA AAAGUUC | 390 |
| 945 | GGUUUCG CUGAUGAGGCCGAAAGGCCGAA AGUGGUG | 391 |
| 946 | AGGUUUC CUGAUGAGGCCGAAAGGCCGAA AAGUGGU | 392 |
| 959 | AUUCCUG CUGAUGAGGCCGAAAGGCCGAA AUCCCAG | 393 |
| 960 | CAUUCCU CUGAUGAGGCCGAAAGGCCGAA AAUCCCA | 394 |
| 1001 | GAAUUCU CUGAUGAGGCCGAAAGGCCGAA AGUGGUU | 395 |
| 1007 | CAGUUUG CUGAUGAGGCCGAAAGGCCGAA AUUCUUA | 396 |
| 1008 | CCAGUUU CUGAUGAGGCCGAAAGGCCGAA AAUUCUU | 397 |
| 1021 | AGUUCUG CUGAUGAGGCCGAAAGGCCGAA AGGCCCC | 398 |
| 1029 | CCCCAGU CUGAUGAGGCCGAAAGGCCGAA AGUUCUG | 399 |
| 1040 | AAAGCUG CUGAUGAGGCCGAAAGGCCGAA AGGCCCC | 400 |
| 1046 | GGGAUCA CUGAUGAGGCCGAAAGGCCGAA AGCUGUA | 401 |
| 1047 | AGGGAUC CUGAUGAGGCCGAAAGGCCGAA AAGCUGU | 402 |
| 1051 | UGUCAGG CUGAUGAGGCCGAAAGGCCGAA AUCAAAG | 403 |
| 1060 | GAUUCCA CUGAUGAGGCCGAAAGGCCGAA AUGUCAG | 404 |
| 1067 | GUCUCCA CUGAUGAGGCCGAAAGGCCGAA AUUCCAG | 405 |
| 1085 | AGAACCA CUGAUGAGGCCGAAAGGCCGAA AGGCUCC | 406 |
| 1086 | CAGAACC CUGAUGAGGCCGAAAGGCCGAA AAGGCUC | 407 |
| 1090 | UGGCCAG CUGAUGAGGCCGAAAGGCCGAA ACCAAAG | 408 |
| 1091 | CUGGCCA CUGAUGAGGCCGAAAGGCCGAA AACCAAA | 409 |
| 1113 | UCUUCUC CUGAUGAGGCCGAAAGGCCGAA AGUCCUG | 410 |
| 1124 | UCUAGGU CUGAUGAGGCCGAAAGGCCGAA AGGUCUU | 411 |
| 1129 | CAAUUUC CUGAUGAGGCCGAAAGGCCGAA AGGUGAG | 412 |
| 1135 | UUGUGUC CUGAUGAGGCCGAAAGGCCGAA AUUUCUA | 413 |
| 1151 | AAGGCCU CUGAUGAGGCCGAAAGGCCGAA AGGUCCA | 414 |
| 1152 | GAAGGCC CUGAUGAGGCCGAAAGGCCGAA AAGGUCC | 415 |
| 1158 | AGAGAGG CUGAUGAGGCCGAAAGGCCGAA AGGCCUA | 416 |
| 1159 | GAGAGAG CUGAUGAGGCCGAAAGGCCGAA AAGGCCU | 417 |
| 1162 | CUGGAGA CUGAUGAGGCCGAAAGGCCGAA AGGAAGG | 418 |
| 1164 | AUCUGGA CUGAUGAGGCCGAAAGGCCGAA AGAGGAA | 419 |
| 1166 | ACAUCUG CUGAUGAGGCCGAAAGGCCGAA AGAGAGG | 420 |
| 1174 | GUCUGGA CUGAUGAGGCCGAAAGGCCGAA ACAUCUG | 421 |
| 1175 | AGUCUGG CUGAUGAGGCCGAAAGGCCGAA AACAUCU | 422 |
| 1176 | AAGUCUG CUGAUGAGGCCGAAAGGCCGAA AAACAUC | 423 |
| 1183 | CUCAAGG CUGAUGAGGCCGAAAGGCCGAA AGUCUGG | 424 |
| 1184 | UCUCAAG CUGAUGAGGCCGAAAGGCCGAA AAGUCUG | 425 |
| 1187 | GUGUCUC CUGAUGAGGCCGAAAGGCCGAA AGGAAGU | 426 |
| 1208 | CCAUGGG CUGAUGAGGCCGAAAGGCCGAA AGGGCUG | 427 |
| 1224 | AUAGAGG CUGAUGAGGCCGAAAGGCCGAA AGCUGGC | 428 |
| 1228 | AUAAAUA CUGAUGAGGCCGAAAGGCCGAA AGGGAGC | 429 |
| 1230 | ACAUAAA CUGAUGAGGCCGAAAGGCCGAA AGAGGGA | 430 |
| 1232 | AAACAUA CUGAUGAGGCCGAAAGGCCGAA AUAGAGG | 431 |
| 1233 | CAAACAU CUGAUGAGGCCGAAAGGCCGAA AAUAGAG | 432 |
| 1234 | GCAAACA CUGAUGAGGCCGAAAGGCCGAA AAAUAGA | 433 |
| 1238 | AAGUGCA CUGAUGAGGCCGAAAGGCCGAA ACAUAAA | 434 |
| 1239 | CAAGUGC CUGAUGAGGCCGAAAGGCCGAA AACAUAA | 435 |
| 1245 | UAAUCAC CUGAUGAGGCCGAAAGGCCGAA AGUGCAA | 436 |
| 1251 | AAUAAAU CUGAUGAGGCCGAAAGGCCGAA AUCACAA | 437 |
| 1252 | UAAUAAA CUGAUGAGGCCGAAAGGCCGAA AAUCACA | 438 |
| 1254 | AAUAAUA CUGAUGAGGCCGAAAGGCCGAA AUAAUCA | 439 |
| 1255 | AAAUAAU CUGAUGAGGCCGAAAGGCCGAA AAUAAUC | 440 |
| 1256 | UAAAUAA CUGAUGAGGCCGAAAGGCCGAA AAAUAAU | 441 |
| 1258 | AAUAAAU CUGAUGAGGCCGAAAGGCCGAA AUAAAUA | 442 |
| 1259 | AAAUAAA CUGAUGAGGCCGAAAGGCCGAA AAUAAAU | 443 |
| 1261 | AUAAAUA CUGAUGAGGCCGAAAGGCCGAA AUAAUAA | 444 |
| 1262 | AAUAAAU CUGAUGAGGCCGAAAGGCCGAA AAUAAUA | 445 |
| 1263 | UAAUAAA CUGAUGAGGCCGAAAGGCCGAA AAAUAAU | 446 |
| 1265 | AAUAAUA CUGAUGAGGCCGAAAGGCCGAA AUAAAUA | 447 |
| 1266 | AAAUAAU CUGAUGAGGCCGAAAGGCCGAA AAUAAAU | 448 |
| 1267 | UAAAUAA CUGAUGAGGCCGAAAGGCCGAA AAAUAAA | 449 |
| 1269 | AAUAAAU CUGAUGAGGCCGAAAGGCCGAA AUAAAUA | 450 |
| 1270 | AAAUAAA CUGAUGAGGCCGAAAGGCCGAA AAUAAAU | 451 |
| 1272 | AUAAAUA CUGAUGAGGCCGAAAGGCCGAA AUAAUAA | 452 |
| 1273 | AAUAAAU CUGAUGAGGCCGAAAGGCCGAA AAUAAUA | 453 |
| 1274 | AAAUAAA CUGAUGAGGCCGAAAGGCCGAA AAAUAAU | 454 |
| 1276 | GUAAAUA CUGAUGAGGCCGAAAGGCCGAA AUAAAUA | 455 |
| 1277 | UGUAAAU CUGAUGAGGCCGAAAGGCCGAA AAUAAAU | 456 |
| 1278 | CUGUAAA CUGAUGAGGCCGAAAGGCCGAA AAAUAAA | 457 |
| 1280 | AUCUGUA CUGAUGAGGCCGAAAGGCCGAA AUAAAUA | 458 |
| 1281 | CAUCUGU CUGAUGAGGCCGAAAGGCCGAA AAUAAAU | 459 |
| 1282 | UCAUCUG CUGAUGAGGCCGAAAGGCCGAA AAAUAAA | 460 |
| 1294 | AAAUAAA CUGAUGAGGCCGAAAGGCCGAA ACAUUCA | 461 |

TABLE III-continued

Human TNF-a Hammerhead Ribozyme Sequences

| nt. Position | HH Ribozyme Sequence | Sequence ID No. |
|---|---|---|
| 1296 | CCAAAUA CUGAUGAGGCCGAAAGGCCGAA AUACAUU | 462 |
| 1297 | CCCAAAU CUGAUGAGGCCGAAAGGCCGAA AAUACAU | 463 |
| 1298 | UCCCAAA CUGAUGAGGCCGAAAGGCCGAA AAAUACA | 464 |
| 1300 | UCUCCCA CUGAUGAGGCCGAAAGGCCGAA AUAAAUA | 465 |
| 1301 | GUCUCCC CUGAUGAGGCCGAAAGGCCGAA AAUAAAU | 466 |
| 1315 | CCCAGGA CUGAUGAGGCCGAAAGGCCGAA ACCCCGG | 467 |
| 1317 | CCCCCAG CUGAUGAGGCCGAAAGGCCGAA AUACCCC | 468 |
| 1334 | CAGCUCC CUGAUGAGGCCGAAAGGCCGAA ACAUUGG | 469 |
| 1345 | CUGAGCC CUGAUGAGGCCGAAAGGCCGAA AGGCAGC | 470 |
| 1350 | CAUGUCU CUGAUGAGGCCGAAAGGCCGAA AGCCAAG | 471 |
| 1359 | CACGGAA CUGAUGAGGCCGAAAGGCCGAA ACAUGUC | 472 |
| 1360 | UCACGGA CUGAUGAGGCCGAAAGGCCGAA AACAUGU | 473 |
| 1361 | UUCACGG CUGAUGAGGCCGAAAGGCCGAA AAACAUG | 474 |
| 1362 | UUUCACG CUGAUGAGGCCGAAAGGCCGAA AAAACAU | 475 |
| 1386 | AACAGCC CUGAUGAGGCCGAAAGGCCGAA AUUGUUC | 476 |
| 1393 | ACAUGGG CUGAUGAGGCCGAAAGGCCGAA ACAGCCU | 477 |
| 1394 | UACAUGG CUGAUGAGGCCGAAAGGCCGAA AACAGCC | 478 |
| 1401 | AGGGGGC CUGAUGAGGCCGAAAGGCCGAA ACAUGGG | 479 |
| 1414 | AGGCACA CUGAUGAGGCCGAAAGGCCGAA AGGCCAG | 480 |
| 1422 | UCAAAAG CUGAUGAGGCCGAAAGGCCGAA AGGCACA | 481 |
| 1423 | AUCAAAA CUGAUGAGGCCGAAAGGCCGAA AAGGCAC | 482 |
| 1425 | UAAUCAA CUGAUGAGGCCGAAAGGCCGAA AGAAGGC | 483 |
| 1426 | AUAAUCA CUGAUGAGGCCGAAAGGCCGAA AAGAAGG | 484 |
| 1427 | CAUAAUC CUGAUGAGGCCGAAAGGCCGAA AAAGAAG | 485 |
| 1431 | AAAACAU CUGAUGAGGCCGAAAGGCCGAA AUCAAAA | 486 |
| 1432 | AAAAACA CUGAUGAGGCCGAAAGGCCGAA AAUCAAA | 487 |
| 1436 | UUUAAAA CUGAUGAGGCCGAAAGGCCGAA ACAUAAU | 488 |
| 1437 | UUUUAAA CUGAUGAGGCCGAAAGGCCGAA AACAUAA | 489 |
| 1438 | AUUUUAA CUGAUGAGGCCGAAAGGCCGAA AAACAUA | 490 |
| 1439 | UAUUUUA CUGAUGAGGCCGAAAGGCCGAA AAAACAU | 491 |
| 1440 | AUAUUUU CUGAUGAGGCCGAAAGGCCGAA AAAAACA | 492 |
| 1441 | AAUAUUU CUGAUGAGGCCGAAAGGCCGAA AAAAAAC | 493 |
| 1446 | CAGAUAA CUGAUGAGGCCGAAAGGCCGAA AUUUUAA | 494 |
| 1448 | AUCAGAU CUGAUGAGGCCGAAAGGCCGAA AUAUUUU | 495 |
| 1449 | AAUCAGA CUGAUGAGGCCGAAAGGCCGAA AAUAUUU | 496 |
| 1451 | UUAAUCA CUGAUGAGGCCGAAAGGCCGAA AUAAUAU | 497 |
| 1456 | ACAACUU CUGAUGAGGCCGAAAGGCCGAA AUCAGAU | 498 |
| 1457 | GACAACU CUGAUGAGGCCGAAAGGCCGAA AAUCAGA | 499 |
| 1461 | UUUAGAC CUGAUGAGGCCGAAAGGCCGAA ACUUAAU | 500 |
| 1464 | UUGUUUA CUGAUGAGGCCGAAAGGCCGAA ACAACUU | 501 |
| 1466 | CAUUGUU CUGAUGAGGCCGAAAGGCCGAA AGACAAC | 502 |
| 1479 | GUCACCA CUGAUGAGGCCGAAAGGCCGAA AUCAGCA | 503 |
| 1480 | GGUCACC CUGAUGAGGCCGAAAGGCCGAA AAUCAGC | 504 |
| 1494 | AAUGAGU CUGAUGAGGCCGAAAGGCCGAA ACAGUUG | 505 |
| 1498 | CAGCAAU CUGAUGAGGCCGAAAGGCCGAA AGUGACA | 506 |
| 1501 | CCUCAGC CUGAUGAGGCCGAAAGGCCGAA AUGAGUG | 507 |
| 1512 | GGGAGCA CUGAUGAGGCCGAAAGGCCGAA AGGCCUC | 508 |
| 1517 | CCCUGGG CUGAUGAGGCCGAAAGGCCGAA AGCAGAG | 509 |
| 1528 | CAGACAC CUGAUGAGGCCGAAAGGCCGAA ACUCCCU | 510 |
| 1533 | GAUUACA CUGAUGAGGCCGAAAGGCCGAA ACACAAC | 511 |
| 1537 | GGCCGAU CUGAUGAGGCCGAAAGGCCGAA ACAGACA | 512 |
| 1540 | GUAGGCC CUGAUGAGGCCGAAAGGCCGAA AUUACAG | 513 |
| 1546 | UGAAUAG CUGAUGAGGCCGAAAGGCCGAA AGGCCGA | 514 |
| 1549 | CACUGAA CUGAUGAGGCCGAAAGGCCGAA AGUAGGC | 515 |
| 1551 | GCCACUG CUGAUGAGGCCGAAAGGCCGAA AUAGUAG | 516 |
| 1552 | CGCCACU CUGAUGAGGCCGAAAGGCCGAA AAUAGUA | 517 |
| 1566 | CAACCUU CUGAUGAGGCCGAAAGGCCGAA AUUUCUC | 518 |
| 1572 | CCUAAGC CUGAUGAGGCCGAAAGGCCGAA ACCUUUA | 519 |
| 1576 | CUUUCCU CUGAUGAGGCCGAAAGGCCGAA AGCAACC | 520 |
| 1577 | UCUUUCC CUGAUGAGGCCGAAAGGCCGAA AAGCAAC | 521 |

TABLE IV

Mouse TNF-a HH Target Sequences

| nt. Position | HH Target Sequence | Sequence ID No. | nt. Position | HH Target Sequence | Sequence ID No. |
|---|---|---|---|---|---|
| 66 | UgGAAAU a GcucCcA | 522 | 324 | GgGUGAU C GGuCCCC | 562 |
| 101 | GGCAGGU U CUgUcCC | 523 | 347 | GAGAagU u cCCAaaU | 563 |
| 101 | GGCAGgU u CUGUccC | 524 | 364 | CCUCcCU C UcAUCAG | 564 |

TABLE IV-continued

Mouse TNF-a HH Target Sequences

| nt. Position | HH Target Sequence | Sequence ID No. | nt. Position | HH Target Sequence | Sequence ID No. |
|---|---|---|---|---|---|
| 102 | GCAGGUU C UgUcCCU | 525 | 366 | UCcCUCU c AUCAGuu | 565 |
| 102 | gCAGgUU c ugUCCCU | 526 | 366 | UcCCUCU C auCAGuU | 566 |
| 106 | GUUCUgU c CCUuUCA | 527 | 369 | CUCUcAU C AGuuCUa | 567 |
| 110 | UgUcCCU u UCACucA | 528 | 376 | CAGuuCU a UGGCCCA | 568 |
| 111 | gUCcCUU u CaCUCAC | 529 | 390 | AgACCCU C AcaCUcA | 569 |
| 111 | guCCCuU u CACuCAc | 530 | 396 | ucaCAcU C AGAUCAU | 570 |
| 112 | UcCCUuU C ACucACU | 531 | 401 | cUCAGAU C AUCUUCU | 571 |
| 116 | UuUCACU C AcUGgcc | 532 | 404 | AGAUCAU C UUCUCaA | 572 |
| 137 | GCCaCAU C uCCcUCc | 533 | 406 | AUCAUCU U CUCaAAa | 573 |
| 139 | caCAuCU C CCUCcAg | 534 | 406 | AUcAUcU U cUcaAAA | 574 |
| 177 | GCAUGAU C CGcGACG | 535 | 407 | UCAUCUU C UCaAAau | 575 |
| 207 | AGGCaCU C CCCcAaA | 536 | 409 | AUCUUCU C aAAauuC | 576 |
| 228 | GGGGCuU C CAGAACU | 537 | 409 | AuCuuCU c AaAAUUC | 577 |
| 228 | GGGGCuU c CAGaacU | 538 | 409 | aUcUUcU c AAAauUc | 578 |
| 236 | CAGaaCU C CAGGCGG | 539 | 432 | ACCCUGU A GCCCAcG | 579 |
| 236 | CAGaACU c cAGgcGg | 540 | | | |
| 249 | GGugCCU a UgUCUcA | 541 | | | |
| 249 | GGuGCCU a UGucUCa | 542 | 444 | AcGUcGU A GCAAACC | 580 |
| | | | 501 | AcGCCCU C CUGGCCA | 581 |
| 261 | UCAGCCU C UUCUCaU | 543 | 560 | gGgUUGU a CCUuguC | 582 |
| 261 | UCAgCCU C UUCUcau | 544 | 560 | GGguUGU A CCUugUC | 583 |
| 263 | AGCCUCU U CUCaUUC | 545 | 564 | UGUACCU u gUCUACU | 584 |
| 263 | AgCCUCU U CUcauUC | 546 | 567 | ACCUugU C UACUCCC | 585 |
| 264 | GCCUCUU C UCaUUCC | 547 | 569 | CUugUCU A CUCCCAG | 586 |
| 264 | gCCUCUU C UcauUCc | 548 | 572 | gUCUACU C CCAGGUu | 587 |
| 266 | CUCUUCU C aUUCCUG | 549 | 572 | GUCUaCU c CCAGguu | 588 |
| 269 | UUCUCaU U CCUGcUu | 550 | 572 | GuCUacU C CCAgGUu | 589 |
| 270 | UCUCaUU C CUGcUuG | 551 | 579 | CCCAGGU u CUCUUCA | 590 |
| 276 | UCCUGcU u GUGGCAG | 552 | 580 | CCAGguU c uCUUcAa | 591 |
| 297 | CCACGCU C UUCUGuC | 553 | 580 | CCaGGuU c UCuUcaa | 592 |
| 299 | ACGCUCU U CUGuCUa | 554 | 582 | AGGUUCU C UUCaagg | 593 |
| 300 | CGCUCUU C UGuCUaC | 555 | 582 | AGGUuCU C UUCAAGG | 594 |
| 304 | CUuCUgU c uAcUGaa | 556 | 584 | GUuCUCU U CAAGGGa | 595 |
| 306 | UcUGUcU a cUgAAcU | 557 | 585 | UuCUCUU C AAGGGaC | 596 |
| 314 | CUGaACU U cGGgGUG | 558 | 608 | CcCGaCU a CgugCUC | 597 |
| 315 | UGaACUU c GGgGUGA | 559 | 615 | aCgUGcU C CUCAcCC | 598 |
| 315 | uGaaCUU c GGGguGa | 560 | 615 | AcGUGCU C CUCACCC | 599 |
| 324 | gGGUGaU c GgUCCcC | 561 | 618 | UGCUCCU C ACCCACA | 600 |
| 630 | ACACCgU C AGCCGau | 601 | 940 | GuCUACU c cUCAGaG | 650 |
| 630 | ACACCgU C AgCCgaU | 602 | 943 | UACUccU C AGaGcCc | 651 |
| 638 | agcCgAU u uGCUaUc | 603 | 972 | UCUaaCU u AgAAAGg | 652 |
| 643 | aUUUGcU a uCUcAuA | 604 | 972 | ucUaaCU u AGAaAgG | 653 |
| 645 | UuGCuaU C UCaUACC | 605 | 973 | CUaACuU A GAAAggG | 654 |
| 647 | GCuaUCU C aUACCAG | 606 | 984 | AGgGgAU U auGGcuc | 655 |
| 663 | agAAaGU C AACCUCC | 607 | 984 | AGGGgaU U aUGgCUc | 656 |
| 669 | UCAACCU C CUCUCUG | 608 | 985 | GGGGauU a uGGcUCa | 657 |
| 669 | UcAAccU c cUcUCUG | 609 | 997 | UcAGAgU c CAAcucu | 658 |
| 672 | ACCUCCU C UCUGCCg | 610 | 1010 | CuguGCU c AGAgCUU | 659 |
| 674 | CUCCUCU C UGCCgUC | 611 | 1017 | cAGAgCU U UcAaCAA | 660 |
| 681 | cUGCCgU C AagaGcC | 612 | 1018 | AGAgCUU U cAaCAAC | 661 |
| 681 | CUGCCgU C AAGAGCC | 613 | 1019 | GAgCUUU c AaCAACu | 662 |
| 681 | CUGcCgU C aaGAgcC | 614 | 1073 | UgGGCCU c ucAUgCA | 663 |
| 734 | CCCUGGU A UGAGCCC | 615 | 1096 | AAGgAcU C AAAugGG | 664 |
| 734 | CccUGGU a ugaGCCc | 616 | 1106 | aUGGGcU U uccGAAU | 665 |
| 744 | AGCCCAU a UAcCUGG | 617 | 1107 | UGGGcUU u ccGAAUu | 666 |
| 746 | CCCAUaU A cCUGGGA | 618 | 1108 | GGgCuUU c cGaaUUC | 667 |
| 759 | GAgGAGU C uuCCAGc | 619 | 1115 | CcGAAuU C ACUGGaG | 668 |
| 759 | GAGGaGU C UUCCAGC | 620 | 1133 | CGAAugU C AuuCcU | 669 |
| 761 | GGaGUCU U CCAGCUG | 621 | 1164 | gagUGgU c AgGUUGc | 670 |
| 762 | GaGUCUU C CAGCUGG | 622 | 1180 | UcUgUcU c agaAUGA | 671 |
| 786 | ACCaACU C AGCGCUG | 623 | 1203 | aaGAuCU c AGGCCUU | 672 |
| 798 | CUGAGgU C AAUCuGC | 624 | 1210 | cAGGCCU U CCUacCU | 673 |
| 802 | GgUCAAU C uGCCCaA | 625 | 1211 | AGGCCUU C CUacCUu | 674 |
| 812 | CCCaAgU A cuUaGAC | 626 | 1214 | CCUUCCU a cCUuCAG | 675 |
| 816 | AgUAcuU a GACUUUG | 627 | 1218 | CcuACcU u CaGACCu | 676 |
| 821 | uUaGACU U UGCgGAG | 628 | 1218 | CCuaCCU U CAGACcu | 677 |
| 822 | UaGACUU U GCgGAGU | 629 | 1218 | cCuACcU u cAgACCU | 678 |
| 830 | GCgGAGU C cGGGCAG | 630 | 1218 | CCUacCU u CAGAccU | 679 |
| 840 | GGCAGGU C UACUUUG | 631 | 1219 | CuaCCUU C AGACcuu | 680 |
| 842 | CAGGUCU A CUUUGGa | 632 | 1219 | CuAcCUU c agAcCUU | 681 |
| 842 | CAGgucU a CUUugGA | 633 | 1226 | CagACCU U uCCAgAC | 682 |
| 842 | cagGuCU a CUUUgGA | 634 | 1226 | CAGAccU U UCCAGAC | 683 |
| 845 | GUCUACU U UGGagUC | 635 | 1227 | agACCUU u CCAgACu | 684 |
| 846 | UCUACUU U GGagUCA | 636 | 1227 | GAccUUU C CCAGACU | 685 |

TABLE IV-continued

Mouse TNF-a HH Target Sequences

| nt. Position | HH Target Sequence | Sequence ID No. | nt. Position | HH Target Sequence | Sequence ID No. |
|---|---|---|---|---|---|
| 852 | UUGGagU C AUUGCuC | 637 | 1228 | GAccUUU C CAGACUc | 686 |
| 855 | GagUCAU U GCuCUGU | 638 | 1238 | gACUCuU c cCUGAGG | 687 |
| 887 | AUCCaUU c ucUACCC | 639 | 1262 | CAGCCuU C CuCAcaG | 688 |
| 891 | AuucuCU a CCCaGCC | 640 | 1283 | CCCCccU C uaUUUAU | 689 |
| 905 | CCcCaCU C UgaCCCC | 641 | 1283 | cCcCCCU C UAUUUAU | 690 |
| 905 | cCCCacU c UgACCCC | 642 | 1285 | cCCCUCU A UUUAUaU | 691 |
| 905 | CcCCACU c uGAccCC | 643 | 1287 | CcuCUAU u UauAuUU | 692 |
| 914 | GAcCCcU U uacUCUG | 644 | 1287 | CCUCUAU U UAUaUUU | 693 |
| 915 | ACCCCuU u acUCuGA | 645 | 1288 | CUCUAUU U AUaUUUG | 694 |
| 919 | CUUUAcU c ugaCCcC | 646 | 1289 | UCUAUUU A UaUUUGC | 695 |
| 928 | GACCcCU u UaUugUC | 647 | 1293 | UUUAUaU U UGCACUU | 696 |
| 928 | gAcCCCU U UAUUguC | 648 | 1293 | uUUaUaU u UGcAcUu | 697 |
| 932 | CCUUUAU U guCuaCU | 649 | 1294 | UUAUaUU U GCACUUa | 698 |
| 1300 | UUGCACU U aUuAUUu | 699 | 1462 | aCCuUGU u GCCuCCU | 747 |
| 1303 | CAcuUaU u AuUuAUU | 700 | 1470 | GccuCcU C UUUUGcU | 748 |
| 1304 | acUuAUU A UUUAUUA | 701 | 1472 | cuCcUCU U UUGcUUA | 749 |
| 1306 | UuAUUAU U UAUUAUU | 702 | 1473 | uCcUCUU U UGcUUAU | 750 |
| 1307 | uAUUAUU U AUUAUUU | 703 | 1474 | CcUCUUU U GcUUAUG | 751 |
| 1307 | UaUUaUU U AuuAUuU | 704 | 1478 | UUUUGcU U AUGUUUa | 752 |
| 1308 | UUAUUU A UUAUUUA | 705 | 1479 | UUUGcUU a UGuuuAa | 753 |
| 1310 | UauUuAU U AUUUAUU | 706 | 1479 | UUUGcUU A UGUUUaa | 754 |
| 1310 | UAUUUAU U AUUUAUU | 707 | 1484 | UUAUGUU U aaaAcAA | 755 |
| 1310 | UAUUUAU U AUUUAUU | 708 | 1498 | AAAuauU U AUCUaAc | 756 |
| 1311 | AUUUAUU A UUUAUUU | 709 | 1511 | AcccAaU U GUCUuAA | 757 |
| 1311 | AUUUAUU A UUUAUUU | 710 | 1514 | cAaUUGU C UuAAuAA | 758 |
| 1311 | AuuUAUU A UuUauUU | 711 | 1516 | aUUGUCU u AAuAAcG | 759 |
| 1313 | UUAUUAU U UAUUUAU | 712 | 1529 | CgcugAU u UGGuGAC | 760 |
| 1313 | UUAUUAU U UAUUUAU | 713 | 1529 | cGCUGAU U UGGUGAC | 761 |
| 1313 | uUAUUAU u UauUUAu | 714 | 1530 | gCUGAUU u gGUgacC | 762 |
| 1314 | UAUUAUU U AUUUAUU | 715 | 1530 | GCUGAUU U GGUGACC | 763 |
| 1314 | UAUUAUU U AUUAUUU | 716 | 1563 | UgaAcCU c UGcUCCC | 764 |
| 1315 | AUUAUUU A UUUAUUA | 717 | 1563 | ugaaCCU C UGCUCCC | 765 |
| 1317 | UAUUUAU U UAUUAUU | 718 | 1568 | CUCUGCU C CCCAcGG | 766 |
| 1318 | AUUUAUU U AUUAUUU | 719 | 1589 | UGaCUGU A AUuGcCC | 767 |
| 1319 | UUUAUUU A UUAUUUA | 720 | 1592 | CUGUAAU u GcCCUAC | 768 |
| 1326 | AUUAUUU A UUUAUUU | 721 | 1617 | GAGAAAU A AAGaUcG | 769 |
| 1328 | UAUUUAU U UAUUUgC | 722 | 1623 | UAAAGaU c GCUUAaa | 770 |
| 1329 | AUUUAUU U AUUUgCu | 723 | 1633 | UUAaaaU a aaAAaCC | 771 |
| 1330 | UUUAUUU A UUUgCuu | 724 | 25 | AgGgaCU a gCCagGA | 772 |
| 1332 | UAUUUAU U UgCuuAU | 725 | | | |
| 1333 | AUUUAUU U gCuuAUG | 726 | | | |
| 1337 | auUUGCU U AuGAAuG | 727 | | | |
| 1338 | uUUGCUU A uGAAuGu | 728 | | | |
| 1346 | UGAAUGU A UUUAUUU | 729 | | | |
| 1348 | AAUGUAU U UAUUUGG | 730 | | | |
| 1349 | AUGUAUU U AUUUGGa | 731 | | | |
| 1350 | UGUAUUU A UUUGGaA | 732 | | | |
| 1352 | uAUuUAU u UGGaAGG | 733 | | | |
| 1352 | UAUUUAU U UGGaAGg | 734 | | | |
| 1353 | AUUUAUU U GGaAGgC | 735 | | | |
| 1369 | GGGGUgU C CUGGaGG | 736 | | | |
| 1398 | gCUguCU U cAGACAg | 737 | | | |
| 1398 | GCUGuCU U cagaCAG | 738 | | | |
| 1412 | GACAUGU U UUCuGUG | 739 | | | |
| 1413 | ACAUGUU U UCuGUGA | 740 | | | |
| 1414 | CAUGUUU U CuGUGAA | 741 | | | |
| 1415 | AUGUUUU C uGUGAAA | 742 | | | |
| 1415 | AUGUUUU c UgugAaA | 743 | | | |
| 1438 | gaGCUGU c CCCAccU | 744 | | | |
| 1451 | CUGGCCU C UcUaCCU | 745 | | | |
| 1453 | ggCCUCU C UaCCuUG | 746 | | | |

TABLE V

Mouse TNF-a Hammerhead Ribozyme Sequences

| nt. Position | Mouse HH Ribozyme Sequence | Sequence ID No. |
|---|---|---|
| 25 | UCCUGGC CUGAUGAGGCCGAAAGGCCGAA AGUCCCU | 773 |
| 66 | UGGGAGC CUGAUGAGGCCGAAAGGCCGAA AUUUCCA | 774 |

TABLE V-continued

Mouse TNF-a Hammerhead Ribozyme Sequences

| nt. Position | Mouse HH Ribozyme Sequence | Sequence ID No. |
|---|---|---|
| 101 | GGGACAG CUGAUGAGGCCGAAAGGCCGAA ACCUGCC | 775 |
| 101 | GGGACAG CUGAUGAGGCCGAAAGGCCGAA ACCUGCC | 776 |
| 102 | AGGGACA CUGAUGAGGCCGAAAGGCCGAA AACCUGC | 777 |
| 102 | AGGGACA CUGAUGAGGCCGAAAGGCCGAA AACCUGC | 778 |
| 106 | UGAAAGG CUGAUGAGGCCGAAAGGCCGAA ACAGAAC | 779 |
| 110 | UGAGUGA CUGAUGAGGCCGAAAGGCCGAA AGGGACA | 780 |
| 111 | GUGAGUG CUGAUGAGGCCGAAAGGCCGAA AAGGGAC | 781 |
| 111 | GUGAGUG CUGAUGAGGCCGAAAGGCCGAA AAGGGAC | 782 |
| 112 | AGUGAGU CUGAUGAGGCCGAAAGGCCGAA AAAGGGA | 783 |
| 116 | GGCCAGU CUGAUGAGGCCGAAAGGCCGAA AGUGAAA | 784 |
| 137 | GGAGGGA CUGAUGAGGCCGAAAGGCCGAA AUGUGGC | 785 |
| 139 | CUGGAGG CUGAUGAGGCCGAAAGGCCGAA AGAUGUG | 786 |
| 177 | CGUCGCG CUGAUGAGGCCGAAAGGCCGAA AUCAUGC | 787 |
| 207 | UUUGGGG CUGAUGAGGCCGAAAGGCCGAA AGUGCCU | 788 |
| 228 | AGUUCUG CUGAUGAGGCCGAAAGGCCGAA AAGCCCC | 789 |
| 228 | AGUUCUG CUGAUGAGGCCGAAAGGCCGAA AAGCCCC | 790 |
| 236 | CCGCCUG CUGAUGAGGCCGAAAGGCCGAA AGUUCUG | 791 |
| 236 | CCGCCUG CUGAUGAGGCCGAAAGGCCGAA AGUUCUG | 792 |
| 249 | UGAGACA CUGAUGAGGCCGAAAGGCCGAA AGGCACC | 793 |
| 249 | UGAGACA CUGAUGAGGCCGAAAGGCCGAA AGGCACC | 794 |
| 261 | AUGAGAA CUGAUGAGGCCGAAAGGCCGAA AGGCUGA | 795 |
| 261 | AUGAGAA CUGAUGAGGCCGAAAGGCCGAA AGGCUGA | 796 |
| 263 | GAAUGAG CUGAUGAGGCCGAAAGGCCGAA AGAGGCU | 797 |
| 263 | GAAUGAG CUGAUGAGGCCGAAAGGCCGAA AGAGGCU | 798 |
| 264 | GGAAUGA CUGAUGAGGCCGAAAGGCCGAA AAGAGGC | 799 |
| 264 | GGAAUGA CUGAUGAGGCCGAAAGGCCGAA AAGAGGC | 800 |
| 266 | CAGGAAU CUGAUGAGGCCGAAAGGCCGAA AGAAGAG | 801 |
| 269 | AAGCAGG CUGAUGAGGCCGAAAGGCCGAA AUGAGAA | 802 |
| 270 | CAAGCAG CUGAUGAGGCCGAAAGGCCGAA AAUGAGA | 803 |
| 276 | CUGCCAC CUGAUGAGGCCGAAAGGCCGAA AGCAGGA | 804 |
| 297 | GACAGAA CUGAUGAGGCCGAAAGGCCGAA AGCGUGG | 805 |
| 299 | UAGACAG CUGAUGAGGCCGAAAGGCCGAA AGAGCGU | 806 |
| 300 | GUAGACA CUGAUGAGGCCGAAAGGCCGAA AAGAGCG | 807 |
| 304 | UUCAGUA CUGAUGAGGCCGAAAGGCCGAA ACAGAAG | 808 |
| 306 | AGUUCAG CUGAUGAGGCCGAAAGGCCGAA AGACAGA | 809 |
| 314 | CACCCCG CUGAUGAGGCCGAAAGGCCGAA AGUUCAG | 810 |
| 315 | UCACCCC CUGAUGAGGCCGAAAGGCCGAA AAGUUCA | 811 |
| 315 | UCACCCC CUGAUGAGGCCGAAAGGCCGAA AAGUUCA | 812 |
| 324 | GGGGACC CUGAUGAGGCCGAAAGGCCGAA AUCACCC | 813 |
| 324 | GGGGACC CUGAUGAGGCCGAAAGGCCGAA AUCACCC | 814 |
| 347 | AUUUGGG CUGAUGAGGCCGAAAGGCCGAA ACUUCUC | 815 |
| 364 | CUGAUGA CUGAUGAGGCCGAAAGGCCGAA AGGGAGG | 816 |
| 366 | AACUGAU CUGAUGAGGCCGAAAGGCCGAA AGAGGGA | 817 |
| 366 | AACUGAU CUGAUGAGGCCGAAAGGCCGAA AGAGGGA | 818 |
| 369 | UAGAACU CUGAUGAGGCCGAAAGGCCGAA AUGAGAG | 819 |
| 376 | UGGGCCA CUGAUGAGGCCGAAAGGCCGAA AGAACUG | 820 |
| 390 | UGAGUGU CUGAUGAGGCCGAAAGGCCGAA AGGGUCU | 821 |
| 396 | AUGAUCU CUGAUGAGGCCGAAAGGCCGAA AGUGUGA | 822 |
| 401 | AGAAGAU CUGAUGAGGCCGAAAGGCCGAA AUCUGAG | 823 |
| 404 | UUGAGAA CUGAUGAGGCCGAAAGGCCGAA AUGAUCU | 824 |
| 406 | UUUUGAG CUGAUGAGGCCGAAAGGCCGAA AGAUGAU | 825 |
| 406 | UUUUGAG CUGAUGAGGCCGAAAGGCCGAA AGAUGAU | 826 |
| 407 | AUUUUGA CUGAUGAGGCCGAAAGGCCGAA AAGAUGA | 827 |
| 409 | GAAUUUU CUGAUGAGGCCGAAAGGCCGAA AGAAGAU | 828 |
| 409 | GAAUUUU CUGAUGAGGCCGAAAGGCCGAA AGAAGAU | 829 |
| 409 | GAAUUUU CUGAUGAGGCCGAAAGGCCGAA AGAAGAU | 830 |
| 432 | CGUGGGC CUGAUGAGGCCGAAAGGCCGAA ACAGGCU | 831 |
| 444 | GGUUUGC CUGAUGAGGCCGAAAGGCCGAA ACGACGU | 832 |
| 501 | UGGCCAG CUGAUGAGGCCGAAAGGCCGAA AGGGCGU | 833 |
| 560 | GACAAGG CUGAUGAGGCCGAAAGGCCGAA ACAACCC | 834 |
| 560 | GACAAGG CUGAUGAGGCCGAAAGGCCGAA ACAACCC | 835 |
| 564 | AGUAGAC CUGAUGAGGCCGAAAGGCCGAA AGGUACA | 836 |
| 567 | GGGAGUA CUGAUGAGGCCGAAAGGCCGAA ACAAGGU | 837 |
| 569 | CUGGGAG CUGAUGAGGCCGAAAGGCCGAA AGACAAG | 838 |
| 572 | AACCUGG CUGAUGAGGCCGAAAGGCCGAA AGUAGAC | 839 |
| 572 | AACCUGG CUGAUGAGGCCGAAAGGCCGAA AGUAGAC | 840 |
| 572 | AACCUGG CUGAUGAGGCCGAAAGGCCGAA AGUAGAC | 841 |
| 579 | UGAAGAG CUGAUGAGGCCGAAAGGCCGAA ACCUGGG | 842 |
| 580 | UUGAAGA CUGAUGAGGCCGAAAGGCCGAA AACCUGG | 843 |
| 580 | UUGAAGA CUGAUGAGGCCGAAAGGCCGAA AACCUGG | 844 |
| 582 | CCUUGAA CUGAUGAGGCCGAAAGGCCGAA AGAACCU | 845 |
| 582 | CCUUGAA CUGAUGAGGCCGAAAGGCCGAA AGAACCU | 846 |
| 584 | UCCCUUG CUGAUGAGGCCGAAAGGCCGAA AGAGAAC | 847 |
| 585 | GUCCCUU CUGAUGAGGCCGAAAGGCCGAA AAGAGAA | 848 |

TABLE V-continued

Mouse TNF-a Hammerhead Ribozyme Sequences

| nt. Position | Mouse HH Ribozyme Sequence | Sequence ID No. |
|---|---|---|
| 608 | GAGCACG CUGAUGAGGCCGAAAGGCCGAA AGUCGGG | 849 |
| 615 | GGGUGAG CUGAUGAGGCCGAAAGGCCGAA AGCACGU | 850 |
| 615 | GGGUGAG CUGAUGAGGCCGAAAGGCCGAA AGCACGU | 851 |
| 618 | UGUGGGU CUGAUGAGGCCGAAAGGCCGAA AGGAGCA | 852 |
| 630 | AUCGGCU CUGAUGAGGCCGAAAGGCCGAA ACGGUGU | 853 |
| 630 | AUCGGCU CUGAUGAGGCCGAAAGGCCGAA ACGGUGU | 854 |
| 638 | GAUAGCA CUGAUGAGGCCGAAAGGCCGAA AUCGGCU | 855 |
| 643 | UAUGAGA CUGAUGAGGCCGAAAGGCCGAA AGCAAAU | 856 |
| 645 | GGUAUGA CUGAUGAGGCCGAAAGGCCGAA AUAGCAA | 857 |
| 647 | CUGGUAU CUGAUGAGGCCGAAAGGCCGAA AGAUAGC | 858 |
| 663 | GGAGGUU CUGAUGAGGCCGAAAGGCCGAA ACUUUCU | 859 |
| 669 | CAGAGAG CUGAUGAGGCCGAAAGGCCGAA AGGUUGA | 860 |
| 669 | CAGAGAG CUGAUGAGGCCGAAAGGCCGAA AGGUUGA | 861 |
| 672 | CGGCAGA CUGAUGAGGCCGAAAGGCCGAA AGGAGGU | 862 |
| 674 | GACGGCA CUGAUGAGGCCGAAAGGCCGAA AGAGGAG | 863 |
| 681 | GGCUCUU CUGAUGAGGCCGAAAGGCCGAA ACGGCAG | 864 |
| 681 | GGCUCUU CUGAUGAGGCCGAAAGGCCGAA ACGGCAG | 865 |
| 681 | GGCUCUU CUGAUGAGGCCGAAAGGCCGAA ACGGCAG | 866 |
| 734 | GGGCUCA CUGAUGAGGCCGAAAGGCCGAA ACCAGGG | 867 |
| 734 | GGGCUCA CUGAUGAGGCCGAAAGGCCGAA ACCAGGG | 868 |
| 744 | CCAGGUA CUGAUGAGGCCGAAAGGCCGAA AUGGGCU | 869 |
| 746 | UCCCAGG CUGAUGAGGCCGAAAGGCCGAA AUAUGGG | 870 |
| 759 | GCUGGAA CUGAUGAGGCCGAAAGGCCGAA ACUCCUC | 871 |
| 759 | GCUGGAA CUGAUGAGGCCGAAAGGCCGAA ACUCCUC | 872 |
| 761 | CAGCUGG CUGAUGAGGCCGAAAGGCCGAA AGACUCC | 873 |
| 762 | CCAGCUG CUGAUGAGGCCGAAAGGCCGAA AAGACUC | 874 |
| 786 | CAGCGCU CUGAUGAGGCCGAAAGGCCGAA AGUUGGU | 875 |
| 798 | GCAGAUU CUGAUGAGGCCGAAAGGCCGAA ACCUCAG | 876 |
| 802 | UUGGGCA CUGAUGAGGCCGAAAGGCCGAA AUUGACC | 877 |
| 812 | GUCUAAG CUGAUGAGGCCGAAAGGCCGAA ACUUGGG | 878 |
| 816 | CAAAGUC CUGAUGAGGCCGAAAGGCCGAA AAGUACU | 879 |
| 821 | CUCCGCA CUGAUGAGGCCGAAAGGCCGAA AGUCUAA | 880 |
| 822 | ACUCCGC CUGAUGAGGCCGAAAGGCCGAA AAGUCUA | 881 |
| 830 | CUGCCCG CUGAUGAGGCCGAAAGGCCGAA ACUCCGC | 882 |
| 840 | CAAAGUA CUGAUGAGGCCGAAAGGCCGAA ACCUGCC | 883 |
| 842 | UCCAAAG CUGAUGAGGCCGAAAGGCCGAA AGACCUG | 884 |
| 842 | UCCAAAG CUGAUGAGGCCGAAAGGCCGAA AGACCUG | 885 |
| 842 | UCCAAAG CUGAUGAGGCCGAAAGGCCGAA AGACCUG | 886 |
| 845 | GACUCCA CUGAUGAGGCCGAAAGGCCGAA AGUAGAC | 887 |
| 846 | UGACUCC CUGAUGAGGCCGAAAGGCCGAA AAGUAGA | 888 |
| 852 | GAGCAAU CUGAUGAGGCCGAAAGGCCGAA ACUCCAA | 889 |
| 855 | ACAGAGC CUGAUGAGGCCGAAAGGCCGAA AUGACUC | 890 |
| 887 | GGGUAGA CUGAUGAGGCCGAAAGGCCGAA AAUGGAU | 891 |
| 891 | GGCUGGG CUGAUGAGGCCGAAAGGCCGAA AGAGAAU | 892 |
| 905 | GGGGUCA CUGAUGAGGCCGAAAGGCCGAA AGUGGGG | 893 |
| 905 | GGGGUCA CUGAUGAGGCCGAAAGGCCGAA AGUGGGG | 894 |
| 905 | GGGGUCA CUGAUGAGGCCGAAAGGCCGAA AGUGGGG | 895 |
| 914 | CAGAGUA CUGAUGAGGCCGAAAGGCCGAA AGGGGUC | 896 |
| 915 | UCAGAGU CUGAUGAGGCCGAAAGGCCGAA AAGGGGU | 897 |
| 919 | GGGGUCA CUGAUGAGGCCGAAAGGCCGAA AGUAAAG | 898 |
| 928 | GACAAUA CUGAUGAGGCCGAAAGGCCGAA AGGGGUC | 899 |
| 928 | GACAAUA CUGAUGAGGCCGAAAGGCCGAA AGGGGUC | 900 |
| 932 | AGUAGAC CUGAUGAGGCCGAAAGGCCGAA AUAAAGG | 901 |
| 940 | CUCUGAG CUGAUGAGGCCGAAAGGCCGAA AGUAGAC | 902 |
| 943 | GGGCUCU CUGAUGAGGCCGAAAGGCCGAA AGGAGUA | 903 |
| 972 | CCUUUCU CUGAUGAGGCCGAAAGGCCGAA AGUUAGA | 904 |
| 972 | CCUUUCU CUGAUGAGGCCGAAAGGCCGAA AGUUAGA | 905 |
| 973 | CCCUUUC CUGAUGAGGCCGAAAGGCCGAA AAGUUAG | 906 |
| 984 | GAGCCAU CUGAUGAGGCCGAAAGGCCGAA AUCCCCU | 907 |
| 984 | GAGCCAU CUGAUGAGGCCGAAAGGCCGAA AUCCCCU | 908 |
| 985 | UGAGCCA CUGAUGAGGCCGAAAGGCCGAA AAUCCCC | 909 |
| 997 | AGAGUUG CUGAUGAGGCCGAAAGGCCGAA ACUCUGA | 910 |
| 1010 | AAGCUCU CUGAUGAGGCCGAAAGGCCGAA AGCACAG | 911 |
| 1017 | UUUUUGA CUGAUGAGGCCGAAAGGCCGAA AGCUCUG | 912 |
| 1018 | GUUGUUG CUGAUGAGGCCGAAAGGCCGAA AAGCUCU | 913 |
| 1019 | AGUUGUU CUGAUGAGGCCGAAAGGCCGAA AAAGCUC | 914 |
| 1073 | UGCAUGA CUGAUGAGGCCGAAAGGCCGAA AGGCCCA | 915 |
| 1096 | CCCAUUU CUGAUGAGGCCGAAAGGCCGAA AGUCCUU | 916 |
| 1106 | AUUCGGA CUGAUGAGGCCGAAAGGCCGAA AGCCCAU | 917 |
| 1107 | AAUUCGG CUGAUGAGGCCGAAAGGCCGAA AAGCCCA | 918 |
| 1108 | GAAUUCG CUGAUGAGGCCGAAAGGCCGAA AAAGCCC | 919 |
| 1115 | CUCCAGU CUGAUGAGGCCGAAAGGCCGAA AAUUCGG | 920 |
| 1133 | AGGAAUG CUGAUGAGGCCGAAAGGCCGAA ACAUUCG | 921 |
| 1164 | GCAACCU CUGAUGAGGCCGAAAGGCCGAA ACCACUC | 922 |

TABLE V-continued

Mouse TNF-a Hammerhead Ribozyme Sequences

| nt. Position | Mouse HH Ribozyme Sequence | Sequence ID No. |
|---|---|---|
| 1180 | UCAUUCU CUGAUGAGGCCGAAAGGCCGAA AGACAGA | 923 |
| 1203 | AAGGCCU CUGAUGAGGCCGAAAGGCCGAA AGAUCUU | 924 |
| 1210 | AGGUAGG CUGAUGAGGCCGAAAGGCCGAA AGGCCUG | 925 |
| 1211 | AAGGUAG CUGAUGAGGCCGAAAGGCCGAA AAGGCCU | 926 |
| 1214 | CUGAAGG CUGAUGAGGCCGAAAGGCCGAA AGGAAGG | 927 |
| 1218 | AGGUCUG CUGAUGAGGCCGAAAGGCCGAA AGGUAGG | 928 |
| 1218 | AGGUCUG CUGAUGAGGCCGAAAGGCCGAA AGGUAGG | 929 |
| 1218 | AGGUCUG CUGAUGAGGCCGAAAGGCCGAA AGGUAGG | 930 |
| 1218 | AGGUCUG CUGAUGAGGCCGAAAGGCCGAA AGGUAGG | 931 |
| 1219 | AAGGUCU CUGAUGAGGCCGAAAGGCCGAA AAGGUAG | 932 |
| 1219 | AAGGUCU CUGAUGAGGCCGAAAGGCCGAA AAGGUAG | 933 |
| 1226 | GUCUGGA CUGAUGAGGCCGAAAGGCCGAA AGGUCUG | 934 |
| 1226 | GUCUGGA CUGAUGAGGCCGAAAGGCCGAA AGGUCUG | 935 |
| 1227 | AGUCUGG CUGAUGAGGCCGAAAGGCCGAA AAGGUCU | 936 |
| 1227 | AGUCUGG CUGAUGAGGCCGAAAGGCCGAA AAGGUCU | 937 |
| 1228 | GAGUCUG CUGAUGAGGCCGAAAGGCCGAA AAAGGUC | 938 |
| 1238 | CCUCAGG CUGAUGAGGCCGAAAGGCCGAA AAGAGUC | 939 |
| 1262 | CUGUGAG CUGAUGAGGCCGAAAGGCCGAA AAGGCUG | 940 |
| 1283 | AUAAAUA CUGAUGAGGCCGAAAGGCCGAA AGGGGGG | 941 |
| 1283 | AUAAAUA CUGAUGAGGCCGAAAGGCCGAA AGGGGGG | 942 |
| 1285 | AUAUAAA CUGAUGAGGCCGAAAGGCCGAA AGAGGGG | 943 |
| 1287 | AAAUAUA CUGAUGAGGCCGAAAGGCCGAA AUAGAGG | 944 |
| 1287 | AAAUAUA CUGAUGAGGCCGAAAGGCCGAA AUAGAGG | 945 |
| 1288 | CAAAUAU CUGAUGAGGCCGAAAGGCCGAA AAUAGAG | 946 |
| 1289 | GCAAAUA CUGAUGAGGCCGAAAGGCCGAA AAAUAGA | 947 |
| 1293 | AAGUGCA CUGAUGAGGCCGAAAGGCCGAA AUAUAAA | 948 |
| 1293 | AAGUGCA CUGAUGAGGCCGAAAGGCCGAA AUAUAAA | 949 |
| 1294 | UAAGUGC CUGAUGAGGCCGAAAGGCCGAA AAUAUAA | 950 |
| 1300 | AAAUAAU CUGAUGAGGCCGAAAGGCCGAA AGUGCAA | 951 |
| 1303 | AAUAAAU CUGAUGAGGCCGAAAGGCCGAA AUAAGUG | 952 |
| 1304 | UAAUAAA CUGAUGAGGCCGAAAGGCCGAA AAUAAGU | 953 |
| 1306 | AAUAAUA CUGAUGAGGCCGAAAGGCCGAA AUAAUAA | 954 |
| 1307 | AAAUAAU CUGAUGAGGCCGAAAGGCCGAA AAUAAUA | 955 |
| 1307 | AAAUAAU CUGAUGAGGCCGAAAGGCCGAA AAUAAUA | 956 |
| 1308 | UAAAUAA CUGAUGAGGCCGAAAGGCCGAA AAAUAAU | 957 |
| 1310 | AAUAAAU CUGAUGAGGCCGAAAGGCCGAA AUAAAUA | 958 |
| 1310 | AAUAAAU CUGAUGAGGCCGAAAGGCCGAA AUAAAUA | 959 |
| 1310 | AAUAAAU CUGAUGAGGCCGAAAGGCCGAA AUAAAUA | 960 |
| 1311 | AAAUAAA CUGAUGAGGCCGAAAGGCCGAA AAUAAAU | 961 |
| 1311 | AAAUAAA CUGAUGAGGCCGAAAGGCCGAA AAUAAAU | 962 |
| 1311 | AAAUAAA CUGAUGAGGCCGAAAGGCCGAA AAUAAAU | 963 |
| 1313 | AUAAAUA CUGAUGAGGCCGAAAGGCCGAA AUAAUAA | 964 |
| 1313 | AUAAAUA CUGAUGAGGCCGAAAGGCCGAA AUAAUAA | 965 |
| 1313 | AUAAAUA CUGAUGAGGCCGAAAGGCCGAA AUAAUAA | 966 |
| 1314 | AAUAAAU CUGAUGAGGCCGAAAGGCCGAA AAUAAUA | 967 |
| 1314 | AAUAAAU CUGAUGAGGCCGAAAGGCCGAA AAUAAUA | 968 |
| 1315 | UAAUAAA CUGAUGAGGCCGAAAGGCCGAA AAAUAAU | 969 |
| 1317 | AAUAAUA CUGAUGAGGCCGAAAGGCCGAA AUAAAUA | 970 |
| 1318 | AAAUAAU CUGAUGAGGCCGAAAGGCCGAA AAUAAAU | 971 |
| 1319 | UAAUAA CUGAUGAGGCCGAAAGGCCGAA AAAUAAA | 972 |
| 1326 | AAAUAAA CUGAUGAGGCCGAAAGGCCGAA AAAUAAU | 973 |
| 1328 | GCAAAUA CUGAUGAGGCCGAAAGGCCGAA AUAAAUA | 974 |
| 1329 | AGCAAAU CUGAUGAGGCCGAAAGGCCGAA AAUAAAU | 975 |
| 1330 | AAGCAAA CUGAUGAGGCCGAAAGGCCGAA AAAUAAA | 976 |
| 1332 | AUAAGCA CUGAUGAGGCCGAAAGGCCGAA AUAAAUA | 977 |
| 1333 | CAUAAGC CUGAUGAGGCCGAAAGGCCGAA AAUAAAU | 978 |
| 1337 | CAUUCAU CUGAUGAGGCCGAAAGGCCGAA AGCAAAU | 979 |
| 1338 | ACAUUCA CUGAUGAGGCCGAAAGGCCGAA AAGCAAA | 980 |
| 1346 | AAAUAAA CUGAUGAGGCCGAAAGGCCGAA ACAUUCA | 981 |
| 1348 | CCAAAUA CUGAUGAGGCCGAAAGGCCGAA AUACAUU | 982 |
| 1349 | UCCAAAU CUGAUGAGGCCGAAAGGCCGAA AAUACAU | 983 |
| 1350 | UUCCAAA CUGAUGAGGCCGAAAGGCCGAA AAAUACA | 984 |
| 1352 | CCUUCCA CUGAUGAGGCCGAAAGGCCGAA AUAAAUA | 985 |
| 1352 | CCUUCCA CUGAUGAGGCCGAAAGGCCGAA AUAAAUA | 986 |
| 1353 | GCCUUCC CUGAUGAGGCCGAAAGGCCGAA AAUAAAU | 987 |
| 1369 | CCUCCAG CUGAUGAGGCCGAAAGGCCGAA ACACCCC | 988 |
| 1398 | CUGUCUG CUGAUGAGGCCGAAAGGCCGAA AGACAGC | 989 |
| 1398 | CUGUCUG CUGAUGAGGCCGAAAGGCCGAA AGACAGC | 990 |
| 1412 | CACAGAA CUGAUGAGGCCGAAAGGCCGAA ACAUGUC | 991 |
| 1413 | UCACAGA CUGAUGAGGCCGAAAGGCCGAA AACAUGU | 992 |
| 1414 | UUCACAG CUGAUGAGGCCGAAAGGCCGAA AAACAUG | 993 |
| 1415 | UUUCACA CUGAUGAGGCCGAAAGGCCGAA AAAACAU | 994 |
| 1415 | UUUCACA CUGAUGAGGCCGAAAGGCCGAA AAAACAU | 995 |
| 1438 | AGGUGGG CUGAUGAGGCCGAAAGGCCGAA ACAGCUC | 996 |

TABLE V-continued

Mouse TNF-a Hammerhead Ribozyme Sequences

| nt. Position | Mouse HH Ribozyme Sequence | Sequence ID No. |
|---|---|---|
| 1451 | AGGUAGA CUGAUGAGGCCGAAAGGCCGAA AGGCCAG | 997 |
| 1453 | CAAGGUA CUGAUGAGGCCGAAAGGCCGAA AGAGGCC | 998 |
| 1455 | AACAAGG CUGAUGAGGCCGAAAGGCCGAA AGAGAGG | 999 |
| 1462 | AGGAGGC CUGAUGAGGCCGAAAGGCCGAA ACAAGGU | 1000 |
| 1470 | AGCAAAA CUGAUGAGGCCGAAAGGCCGAA AGGAGGC | 1001 |
| 1472 | UAAGCAA CUGAUGAGGCCGAAAGGCCGAA AGAGGAG | 1002 |
| 1473 | AUAAGCA CUGAUGAGGCCGAAAGGCCGAA AAGAGGA | 1003 |
| 1474 | CAUAAGC CUGAUGAGGCCGAAAGGCCGAA AAAGAGG | 1004 |
| 1478 | UAAACAU CUGAUGAGGCCGAAAGGCCGAA AGCAAAA | 1005 |
| 1479 | UUAAACA CUGAUGAGGCCGAAAGGCCGAA AAGCAAA | 1006 |
| 1479 | UUAAACA CUGAUGAGGCCGAAAGGCCGAA AAGCAAA | 1007 |
| 1484 | UUGUUUU CUGAUGAGGCCGAAAGGCCGAA AACAUAA | 1008 |
| 1498 | GUUAGAU CUGAUGAGGCCGAAAGGCCGAA AAUAUUU | 1009 |
| 1511 | UUAAGAC CUGAUGAGGCCGAAAGGCCGAA AUUGGGU | 1010 |
| 1514 | UUAUUAA CUGAUGAGGCCGAAAGGCCGAA ACAAUUG | 1011 |
| 1516 | CGUUAUU CUGAUGAGGCCGAAAGGCCGAA AGACAAU | 1012 |
| 1529 | GUCACCA CUGAUGAGGCCGAAAGGCCGAA AUCAGCG | 1013 |
| 1529 | GUCACCA CUGAUGAGGCCGAAAGGCCGAA AUCAGCG | 1014 |
| 1530 | GGUCACC CUGAUGAGGCCGAAAGGCCGAA AAUCAGC | 1015 |
| 1530 | GGUCACC CUGAUGAGGCCGAAAGGCCGAA AAUCAGC | 1016 |
| 1563 | GGGAGCA CUGAUGAGGCCGAAAGGCCGAA AGGUUCA | 1017 |
| 1563 | GGGAGCA CUGAUGAGGCCGAAAGGCCGAA AGGUUCA | 1018 |
| 1568 | CCGUGGG CUGAUGAGGCCGAAAGGCCGAA AGCAGAG | 1019 |
| 1589 | GGGCAAU CUGAUGAGGCCGAAAGGCCGAA ACAGUCA | 1020 |
| 1592 | GUAGGGC CUGAUGAGGCCGAAAGGCCGAA AUUACAG | 1021 |
| 1617 | CGAUCUU CUGAUGAGGCCGAAAGGCCGAA AUUUCUC | 1022 |
| 1623 | UUUAAGC CUGAUGAGGCCGAAAGGCCGAA AUCUUUA | 1023 |
| 1633 | GGUUUUU CUGAUGAGGCCGAAAGGCCGAA AUUUUAA | 1024 |

TABLE VI

Human TNF-a Hairpin Ribozyme Sequences

| nt. Position | Hairpin Ribozyme Sequence | Sequence ID No. | Substrate | Sequence ID No. |
|---|---|---|---|---|
| 46 | AGCCGUGG AGAA GUAUGU ACCAGAGAAACACACGUUGUGGUACAUUACCUGGUA | 1025 | ACAUACU GAC CCACGGCU | 1058 |
| 54 | GAGGGUGG AGAA GUGGGU ACCAGAGAAACACACGUUGUGGUACAUUACCUGGUA | 1026 | ACCCACG GCU CCACCCUC | 1059 |
| 185 | GGAGAAGA AGAA GAGGAA ACCAGAGAAACACACGUUGUGGUACAUUACCUGGUA | 1027 | UUCCUCA GCC UCUUCUCC | 1060 |
| 201 | CUGCCACG AGAA GGAAGG ACCAGAGAAACACACGUUGUGGUACAUUACCUGGUA | 1028 | CCUUCCU GAU CGUGGCAG | 1061 |
| 230 | GUGCAGCA AGAA GAAGAG ACCAGAGAAACACACGUUGUGGUACAUUACCUGGUA | 1029 | CUCUUCU GCC UGCUGCAC | 1062 |
| 234 | CAAAGUGC AGAA GGCAGA ACCAGAGAAACACACGUUGUGGUACAUUACCUGGUA | 1030 | UCUGCCU GCU GCACUUUG | 1063 |
| 254 | CCUCUGGG AGAA GAUCAC ACCAGAGAAACACACGUUGUGGUACAUUACCUGGUA | 1031 | GUGAUCG GCC CCCAGAGG | 1064 |
| 296 | GGCCAGAG AGAA GAUUAG ACCAGAGAAACACACGUUGUGGUACAUUACCUGGUA | 1032 | CUAAUCA GCC CUCUGGCC | 1065 |
| 317 | AGAAGAUG AGAA GACUGC ACCAGAGAAACACACGUUGUGGUACAUUACCUGGUA | 1033 | GCAGUCA GAU CAUCUUCU | 1066 |
| 387 | GCCACUGG AGAA GCCCCU ACCAGAGAAACACACGUUGUGGUACAUUACCUGGUA | 1034 | AGGGGCA GCU CCAGUGGC | 1067 |
| 404 | AUUGGCCC AGAA GUUCAG ACCAGAGAAACACACGUUGUGGUACAUUACCUGGUA | 1035 | CUGAACC GCC GGGCCAAU | 1068 |
| 453 | GCACCACC AGAA GGUUAU ACCAGAGAAACACACGUUGUGGUACAUUACCUGGUA | 1036 | AUAACCA GCU GGUGGUGC | 1069 |
| 518 | GGUGGAGG AGAA GCCUUG ACCAGAGAAACACACGUUGUGGUACAUUACCUGGUA | 1037 | CAAGGCU GCC CCUCCACC | 1070 |
| 554 | GGCGAUGC AGAA GAUGGU ACCAGAGAAACACACGUUGUGGUACAUUACCUGGUA | 1038 | ACCAUCA GCC GCAUCGCC | 1071 |
| 565 | UGGUAGGA AGAA GCGAUG ACCAGAGAAACACACGUUGUGGUACAUUACCUGGUA | 1039 | CAUCGCC GUC UCCUACCA | 1072 |
| 576 | UGACCUUG AGAA GGUAGG ACCAGAGAAACACACGUUGUGGUACAUUACCUGGUA | 1040 | CCUACCA GAC CAAGGUCA | 1073 |
| 687 | CCUUCUCC AGAA GGAAGA ACCAGAGAAACACACGUUGUGGUACAUUACCUGGUA | 1041 | UCUUCCA GCU GGAGAAGG | 1074 |
| 704 | AGCGCUGA AGAA GUCACC ACCAGAGAAACACACGUUGUGGUACAUUACCUGGUA | 1042 | GGUGACC GAC | 1075 |

TABLE VI-continued

Human TNF-a Hairpin Ribozyme Sequences

| nt. Position | Hairpin Ribozyme Sequence | Sequence ID No. | Substrate | Sequence ID No. |
|---|---|---|---|---|
| 726 | GAUAGUCG AGAA GAUUGA ACCAGAGAAACACACGUUGUGGUACAUUACCUGGUA | 1043 | UCAGCGCU UCAAUCG GCC CGACUAUC | 1076 |
| 730 | UCGAGAUA AGAA GGCCGA ACCAGAGAAACACACGUUGUGGUACAUUACCUGGUA | 1044 | UCGGCCC GAC UAUCUCGA | 1077 |
| 824 | GGGAUUGG AGAA GGGGAG ACCAGAGAAACACACGUUGUGGUACAUUACCUGGUA | 1045 | CUCCCCU GCC CCAAUCCC | 1078 |
| 1042 | GGGAUCAA AGAA GUAGGC ACCAGAGAAACACACGUUGUGGUACAUUACCUGGUA | 1046 | GCCUACA GCU UUGAUCCC | 1079 |
| 1168 | CUGGAAAC AGAA GGAGAG ACCAGAGAAACACACGUUGUGGUACAUUACCUGGUA | 1047 | CUCUCCA GAU GUUUCCAG | 1080 |
| 1178 | UCAAGGAA AGGA GGAAAC ACCAGAGAAACACACGUUGUGGUACAUUACCUGGUA | 1048 | GUUUCCA GAC UUCCUUGA | 1081 |
| 1202 | AUGGGGAG AGAA GGGCUC ACCAGAGAAACACACGUUGUGGUACAUUACCUGGUA | 1049 | GAGCCCA GCC CUCCCCAU | 1082 |
| 1220 | AUAGAGGG AGAA GGCUCC ACCAGAGAAACACACGUUGUGGUACAUUACCUGGUA | 1050 | GGAGCCA GCU CCCUCUAU | 1083 |
| 1284 | AUACAUUC AGAA GUAAAU ACCAGAGAAACACACGUUGUGGUACAUUACCUGGUA | 1051 | AUUUACA GAU GAAUGUAU | 1084 |
| 1340 | UGAGCCAA AGAA GCUCCU ACCAGAGAAACACACGUUGUGGUACAUUACCUGGUA | 1052 | AGGAGCU GCC UUGGCUCA | 1085 |
| 1390 | UACAUGGG AGAA GCCUAU ACCAGAGAAACACACGUUGUGGUACAUUACCUGGUA | 1053 | AUAGGCU GUU CCCAUGUA | 1086 |
| 1452 | ACAACUUA AGAA GAUAAU ACCAGAGAAACACACGUUGUGGUACAUUACCUGGUA | 1054 | AUUAUCU GAU UAAGUUGU | 1087 |
| 1475 | GUCACCAA AGAA GCAUUG ACCAGAGAAACACACGUUGUGGUACAUUACCUGGUA | 1055 | CAAUGCU GAU UUGGUGAC | 1088 |
| 1513 | CCCUGGGG AGAA GAGGCC ACCAGAGAAACACACGUUGUGGUACAUUACCUGGUA | 1056 | GGCCUCU GCU CCCCAGGG | 1089 |
| 1541 | GAAUAGUA AGAA GAUUAC ACCAGAGAAACACACGUUGUGGUACAUUACCUGGUA | 1057 | GUAAUCG GCC UACUAUUC | 1090 |

TABLE VII

Mouse TNF-a Hairpin Ribozyme Sequences

| nt. | Hairpin Ribozyme Sequence | Sequence ID No. | Substrate | Sequence ID No. |
|---|---|---|---|---|
| 103 | GUGAAAGG AGAA GAACCU ACCAGAGAAACACACGUUGUGGUACAUUACCUGGUA | 1091 | AGGUUCU GUC CCUUUCAC | 1124 |
| 256 | UGAGAAGA AGAA GAGACA ACCAGAGAAACACACGUUGUGGUACAUUACCUGGUA | 1092 | UGUCUCA GCC UCUUCUCA | 1125 |
| 272 | CUGCCACA AGAA GGAAUG ACCAGAGAAACACACGUUGUGGUACAUUACCUGGUA | 1093 | CAUUCCU GCU UGUGGCAG | 1126 |
| 301 | GUUCAGUA AGAA GAAGAG ACCAGAGAAACACACGUUGUGGUACAUUACCUGGUA | 1094 | CUCUUCU GUC UACUGAAC | 1127 |
| 325 | CCUUUGGG AGAA GAUCAC ACCAGAGAAACACACGUUGUGGUACAUUACCUGGUA | 1095 | GUGAUCG GUC CCCAAAGG | 1128 |
| 370 | GGCCAUAG AGAA GAUGAG ACCAGAGAAACACACGUUGUGGUACAUUACCUGGUA | 1096 | CUCAUCA GUU CUAUGGCC | 1129 |
| 383 | GUGUGAGG AGAA GGGCCA ACCAGAGAAACACACGUUGUGGUACAUUACCUGGUA | 1097 | UGGCCCA GAC CCUCACAC | 1130 |
| 397 | AGAAGAUG AGAA GAGUGU ACCAGAGAAACACACGUUGUGGUACAUUACCUGGUA | 1098 | ACACUCA GAU CAUCUUCU | 1131 |
| 467 | GCCACUCC AGAA GCUCCU ACCAGAGAAACACACGUUGUGGUACAUUACCUGGUA | 1099 | AGGAGCA GCU GGAGUGGC | 1132 |
| 546 | AACCCAUC AGAA GGCACC ACCAGAGAAACACACGUUGUGGUACAUUACCUGGUA | 1100 | GGUGCCA GCC GAUGGGUU | 1133 |
| 549 | UACAACCC AGAA GCUGGC ACCAGAGAAACACACGUUGUGGUACAUUACCUGGUA | 1101 | GCCAGCC GAU GGGUUGUA | 1134 |
| 598 | GUAGUCGG AGAA GCCUUG ACCAGAGAAACACACGUUGUGGUACAUUACCUGGUA | 1102 | CAAGGCU GCC CCGACUAC | 1135 |
| 603 | AGCACGUA AGAA GGGCAG ACCAGAGAAACACACGUUGUGGUACAUUACCUGGUA | 1103 | CUGCCCC GAC UACGUGCU | 1136 |
| 631 | AGCAAAUC AGAA GACGGU ACCAGAGAAACACACGUUGUGGUACAUUACCUGGUA | 1104 | ACCGUCA GCC GAUUUGCU | 1137 |
| 634 | GAUAGCAA AGAA GCUGAC ACCAGAGAAACACACGUUGUGGUACAUUACCUGGUA | 1105 | GUCAGCC GAU UUGCUAUC | 1138 |
| 675 | CUCUUGAC AGAA GAGAGG ACCAGAGAAACACACGUUGUGGUACAUUACCUGGUA | 1106 | CCUCUCU GCC GUCAAGAG | 1139 |

TABLE VII-continued

Mouse TNF-a Hairpin Ribozyme Sequences

| nt. | Hairpin Ribozyme Sequence | Sequence ID No. | Substrate | Sequence ID No. |
|-----|---------------------------|-----------------|-----------|-----------------|
| 691 | GUCCUUGG AGAA GGGGCU ACCAGAGAAACACACGUUGUGGUACAUUACCUGGUA | 1107 | AGCCCCU GCC CCAAGGAC | 1140 |
| 764 | CCUUCUCC AGAA GGAAGA ACCAGAGAAACACACGUUGUGGUACAUUACCUGGUA | 1108 | UCUUCCA GCU GGAGAAGG | 1141 |
| 803 | AGUACUUG AGAA GAUUGA ACCAGAGAAACACACGUUGUGGUACAUUACCUGGUA | 1109 | UCAAUCU GCC CAAGUACU | 1142 |
| 895 | AGAGUGGG AGAA GGGUAG ACCAGAGAAACACACGUUGUGGUACAUUACCUGGUA | 1110 | CUACCCA GCC CCCACUCU | 1143 |
| 906 | GUAAAGGG AGAA GAGUGG ACCAGAGAAACACACGUUGUGGUACAUUACCUGGUA | 1111 | CCACUCU GAC CCCUUUAC | 1144 |
| 920 | AUAAAGGG AGAA GAGUAA ACCAGAGAAACACACGUUGUGGUACAUUACCUGGUA | 1112 | UUACUCU GAC CCCUUUAU | 1145 |
| 953 | AGGACACA AGAA GGGGGC ACCAGAGAAACACACGUUGUGGUACAUUACCUGGUA | 1113 | GCCCCCA GUC UGUGUCCU | 1146 |
| 1175 | CAUUCUGA AGAA GAGGCA ACCAGAGAAACACACGUUGUGGUACAUUACCUGGUA | 1114 | UGCCUCU GUC UCAGAAUG | 1147 |
| 1220 | CUGGAAAG AGAA GAAGGU ACCAGAGAAACACACGUUGUGGUACAUUACCUGGUA | 1115 | ACCUUCA GAC CUUUCCAG | 1148 |
| 1230 | AGGGAAGA AGAA GGAAAG ACCAGAGAAACACACGUUGUGGUACAUUACCUGGUA | 1116 | CUUUCCA GAC UCUUCCCU | 1149 |
| 1256 | GUGAGGAA AGAA GUGCAU ACCAGAGAAACACACGUUGUGGUACAUUACCUGGUA | 1117 | AUGCACA GCC UUCCUCAC | 1150 |
| 1274 | UAGAGGGG AGAA GGCUCU ACCAGAGAAACACACGUUGUGGUACAUUACCUGGUA | 1118 | AGAGCCA GCC CCCCUCUA | 1151 |
| 1393 | UGUCUGAA AGAA GCUUCC ACCAGAGAAACACACGUUGUGGUACAUUACCUGGUA | 1119 | GGAAGCU GUC UUCAGACA | 1152 |
| 1435 | CAGGUGGG AGAA GCUCAG ACCAGAGAAACACACGUUGUGGUACAUUACCUGGUA | 1120 | CUGAGCU GUC CCCACCUG | 1153 |
| 1525 | GUCACCAA AGAA GCGUUA ACCAGAGAAACACACGUUGUGGUACAUUACCUGGUA | 1121 | UAACGCU GAU UUGGUGAC | 1154 |
| 1542 | GAUGUAGC AGAA GCCUGG ACCAGAGAAACACACGUUGUGGUACAUUACCUGGUA | 1122 | CCAGGCU GUC GCUACAUC | 1155 |
| 1564 | CCGUGGGG AGAA GAGGUU ACCAGAGAAACACACGUUGUGGUACAUUACCUGGUA | 1123 | AACCUCU GCU CCCCACGG | 1156 |

SEQUENCE LISTING ( 1 ) GENERAL INFORMATION:

( i i i ) NUMBER OF SEQUENCES: 1157

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for
        any base. "H"represents
        nucleotide C, A, or U.

( x i ) SEQUENCE DESCRIPTION: SEQ ID NO: 1:

NNNNUHNNNN N        1 1

( 2 ) INFORMATION FOR SEQ ID NO: 2:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i x ) FEATURE:

( D ) OTHER INFORMATION: The letter "N"stands for
any base.

( x i ) SEQUENCE DESCRIPTION: SEQ ID NO: 2:

NNNNNCUGAN GAGNNNNNNC GAAANNNN 28

( 2 ) INFORMATION FOR SEQ ID NO: 3:

( i ) SEQUENCE CHARACTERISTICS:
( A ) LENGTH: 14
( B ) TYPE: nucleic acid
( C ) STRANDEDNESS: single
( D ) TOPOLOGY: linear ( i x ) FEATURE:
( D ) OTHER INFORMATION: The letter "N"stands for
any base. The leter "Y"is
U or C. The letter "H"is
A, U, or C.

( x i ) SEQUENCE DESCRIPTION: SEQ ID NO: 3:

NNNYNGHYNN NNNN 14

( 2 ) INFORMATION FOR SEQ ID NO: 4:

( i ) SEQUENCE CHARACTERISTICS:
( A ) LENGTH: 50
( B ) TYPE: nucleic acid
( C ) STRANDEDNESS: single
( D ) TOPOLOGY: linear ( i x ) FEATURE:
( D ) OTHER INFORMATION: The letter "N"stands for
any base.

( x i ) SEQUENCE DESCRIPTION: SEQ ID NO: 4:

NNNNNNGAA GNNNNNNNN NAAACANNNN NNNNNNNACA UUACNNNNNN 50

( 2 ) INFORMATION FOR SEQ ID NO: 5:

( i ) SEQUENCE CHARACTERISTICS:
( A ) LENGTH: 85
( B ) TYPE: nucleic acid
( C ) STRANDEDNESS: single
( D ) TOPOLOGY: linear ( x i ) SEQUENCE DESCRIPTION: SEQ ID NO: 5:

UGGCCGGCAU GGUCCCAGCC UCCUCGCUGG CGCCGGCUGG GCAACAUUCC GAGGGGACCG 60

UCCCCUCGGU AAUGGCGAAU GGGAC 85

( 2 ) INFORMATION FOR SEQ ID NO: 6:

( i ) SEQUENCE CHARACTERISTICS:
( A ) LENGTH: 176
( B ) TYPE: nucleic acid
( C ) STRANDEDNESS: single
( D ) TOPOLOGY: linear ( x i ) SEQUENCE DESCRIPTION: SEQ ID NO: 6:

GGGAAAGCUU GCGAAGGGCG UCGUCGCCCC GAGCGGUAGU AAGCAGGGAA CUCACCUCCA 60

AUUUCAGUAC UGAAAUUGUC GUAGCAGUUG ACUACUGUUA UGUGAUUGGU AGAGGCUAAG 120

UGACGGUAUU GGCGUAAGUC AGUAUUGCAG CACAGCACAA GCCCGCUUGC GAGAAU 176

( 2 ) INFORMATION FOR SEQ ID NO: 7:

( i ) SEQUENCE CHARACTERISTICS:
( A ) LENGTH: 18

( B ) TYPE: nucleic acid
( C ) STRANDEDNESS: single
( D ) TOPOLOGY: linear ( x i ) SEQUENCE DESCRIPTION: SEQ ID NO: 7:

GGAAGCUGUC UUCAGACA                                                                    18

( 2 ) INFORMATION FOR SEQ ID NO: 8:

( i ) SEQUENCE CHARACTERISTICS:
( A ) LENGTH: 54
( B ) TYPE: nucleic acid
( C ) STRANDEDNESS: single
( D ) TOPOLOGY: linear ( x i ) SEQUENCE DESCRIPTION: SEQ ID NO: 8:

UGUCUGAAAG AAGCUUCCAC CAGAGAAACA CACGUUGUGG UACAUUACCU GGUA                            54

( 2 ) INFORMATION FOR SEQ ID NO: 9:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 9:

GGAAGCUGUC UUCAGACA                                                                    18

( 2 ) INFORMATION FOR SEQ ID NO: 10:

( i ) SEQUENCE CHARACTERISTICS:
( A ) LENGTH: 54
( B ) TYPE: nucleic acid
( C ) STRANDEDNESS: single
( D ) TOPOLOGY: linear ( x i ) SEQUENCE DESCRIPTION: SEQ ID NO: 10:

UGUCUGAAAU AAGCUUCCAC CAGAGAAAGA CACGUUGUGG UACAUUACCU GGUA                            54

( 2 ) INFORMATION FOR SEQ ID NO: 11:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 11:

CUGAGCUGUC CCCACCUG                                                                    18

( 2 ) INFORMATION FOR SEQ ID NO: 12:

( i ) SEQUENCE CHARACTERISTICS:
( A ) LENGTH: 54
( B ) TYPE: nucleic acid
( C ) STRANDEDNESS: single
( D ) TOPOLOGY: linear ( x i ) SEQUENCE DESCRIPTION: SEQ ID NO: 12:

CAGGUGGGAG AAGCUCAGAC CAGAGAAACA CACGUUGUGG UACAUUACCU GGUA                            54

( 2 ) INFORMATION FOR SEQ ID NO: 13:

( i ) SEQUENCE CHARACTERISTICS:
( A ) LENGTH: 18
( B ) TYPE: nucleic acid
( C ) STRANDEDNESS: single (D) TOPOLOGY: linear (xi) SEQUENCE DESCRIPTION: SEQ ID NO: 13:

CUGAGCUGUC CCCACCUG 18

(2) INFORMATION FOR SEQ ID NO: 14:

(i) SEQUENCE CHARACTERISTICS:
        (A) LENGTH: 54
        (B) TYPE: nucleic acid
        (C) STRANDEDNESS: single
        (D) TOPOLOGY: linear (xi) SEQUENCE DESCRIPTION: SEQ ID NO: 14:

CAGGUGGGAU AAGCUCAGAC CAGAGAAAGA CACGUUGUGG UACAUUACCU GGUA 54

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:15:

GGCAGGUUCU CUUCC 15

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:16:

GCAGGUUCUC UUCCU 15

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:17:

AGGUUCUCUU CCUCU 15

(2) INFORMATION FOR SEQ ID NO:18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:18:

GUUCUCUUCC UCUCA 15

(2) INFORMATION FOR SEQ ID NO:19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:19:

UUCUCUUCCU CUCAC                                                                15

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

UCUUCCUCUC ACAUA                                                                15

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

UUCCUCUCAC AUACU                                                                15

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CUCACAUACU GACCC                                                                15

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

CACGGCUCCA CCCUC                                                                15

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CCACCCUCUC UCCCC                                                                15

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
ACCCUCUCUC CCCUG                                                        15
```

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:26:

```
CCUCUCUCCC CUGGA                                                        15
```

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:27:

```
GCAUGAUCCG GGACG                                                        15
```

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:28:

```
AGGCGCUCCC CAAGA                                                        15
```

(2) INFORMATION FOR SEQ ID NO:29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:29:

```
CAGGGCUCCA GGCGG                                                        15
```

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:30:

```
CGGUGCUUGU UCCUC                                                        15
```

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:31:

```
UGCUUGUUCC UCAGC                                                        15
```

( 2 ) INFORMATION FOR SEQ ID NO:32:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

GCUUGUUCCU CAGCC 15

( 2 ) INFORMATION FOR SEQ ID NO:33:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

UGUUCCUCAG CCUCU 15

( 2 ) INFORMATION FOR SEQ ID NO:34:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:34:

UCAGCCUCUU CUCCU 15

( 2 ) INFORMATION FOR SEQ ID NO:35:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:35:

AGCCUCUUCU CCUUC 15

( 2 ) INFORMATION FOR SEQ ID NO:36:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:36:

GCCUCUUCUC CUUCC 15

( 2 ) INFORMATION FOR SEQ ID NO:37:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:37:

CUCUUCUCCU UCCUG 15

( 2 ) INFORMATION FOR SEQ ID NO:38:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:38:

UUCUCCUUCC UGAUC                         15

( 2 ) INFORMATION FOR SEQ ID NO:39:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

UCUCCUUCCU GAUCG                         15

( 2 ) INFORMATION FOR SEQ ID NO:40:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

UCCUGAUCGU GGCAG                         15

( 2 ) INFORMATION FOR SEQ ID NO:41:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

CCACGCUCUU CUGCC                         15

( 2 ) INFORMATION FOR SEQ ID NO:42:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

ACGCUCUUCU GCCUG                         15

( 2 ) INFORMATION FOR SEQ ID NO:43:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CGCUCUUCUG CCUGC                         15

( 2 ) INFORMATION FOR SEQ ID NO:44:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:44:

CUGCACUUUG GAGUG 15

( 2 ) INFORMATION FOR SEQ ID NO:45:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:45:

UGCACUUUGG AGUGA 15

( 2 ) INFORMATION FOR SEQ ID NO:46:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:46:

GAGUGAUCGG CCCCC 15

( 2 ) INFORMATION FOR SEQ ID NO:47:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:47:

GAAGAGUCCC CCAGG 15

( 2 ) INFORMATION FOR SEQ ID NO:48:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:48:

GGGACCUCUC UCUAA 15

( 2 ) INFORMATION FOR SEQ ID NO:49:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:49:

GACCUCUCUC UAAUC 15

( 2 ) INFORMATION FOR SEQ ID NO:50:

( i ) SEQUENCE CHARACTERISTICS:
( A ) LENGTH: 15 base pairs
( B ) TYPE: nucleic acid ( C ) STRANDEDNESS: single
( D ) TOPOLOGY: linear ( x i ) SEQUENCE DESCRIPTION: SEQ ID NO:50:

CCUCUCUCUA AUCAG 15

( 2 ) INFORMATION FOR SEQ ID NO:51:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:51:

UCUCUCUAAU CAGCC 15

( 2 ) INFORMATION FOR SEQ ID NO:52:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:52:

CUCUAAUCAG CCCUC 15

( 2 ) INFORMATION FOR SEQ ID NO:53:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:53:

CAGCCCUCUG GCCCA 15

( 2 ) INFORMATION FOR SEQ ID NO:54:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:54:

GUCAGAUCAU CUUCU 15

( 2 ) INFORMATION FOR SEQ ID NO:55:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:55:

AGAUCAUCUU CUCGA 15

( 2 ) INFORMATION FOR SEQ ID NO:56:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:56:

AUCAUCUUCU CGAAC   15

( 2 ) INFORMATION FOR SEQ ID NO:57:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

UCAUCUUCUC GAACC   15

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

AUCUUCUCGA ACCCC   15

( 2 ) INFORMATION FOR SEQ ID NO:59:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

AGCCUGUAGC CCAUG   15

( 2 ) INFORMATION FOR SEQ ID NO:60:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

CCCAUGUUGU AGCAA   15

( 2 ) INFORMATION FOR SEQ ID NO:61:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AUGUUGUAGC AAACC   15

( 2 ) INFORMATION FOR SEQ ID NO:62:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

AAACCCUCAA GCUGA 15

(2) INFORMATION FOR SEQ ID NO:63:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:63:

GGCAGCUCCA GUGGC 15

(2) INFORMATION FOR SEQ ID NO:64:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:64:

AUGCCCUCCU GGCCA 15

(2) INFORMATION FOR SEQ ID NO:65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:65:

GAGAGAUAAC CAGCU 15

(2) INFORMATION FOR SEQ ID NO:66:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:66:

GUGCCAUCAG AGGGC 15

(2) INFORMATION FOR SEQ ID NO:67:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:67:

GGCCUGUACC UCAUC 15

(2) INFORMATION FOR SEQ ID NO:68:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:68:

UGUACCUCAU CUACU 15

( 2 ) INFORMATION FOR SEQ ID NO:69:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

ACCUCAUCUA CUCCC 15

( 2 ) INFORMATION FOR SEQ ID NO:70:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

CUCAUCUACU CCCAG 15

( 2 ) INFORMATION FOR SEQ ID NO:71:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AUCUACUCCC AGGUC 15

( 2 ) INFORMATION FOR SEQ ID NO:72:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

CCCAGGUCCU CUUCA 15

( 2 ) INFORMATION FOR SEQ ID NO:73:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

AGGUCCUCUU CAAGG 15

( 2 ) INFORMATION FOR SEQ ID NO:74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

GUCCUCUUCA AGGGC 15

( 2 ) INFORMATION FOR SEQ ID NO:75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

UCCUCUUCAA GGGCC         15

( 2 ) INFORMATION FOR SEQ ID NO:76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

UGCCCCUCCA CCCAU         15

( 2 ) INFORMATION FOR SEQ ID NO:77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

AUGUGCUCCU CACCC         15

( 2 ) INFORMATION FOR SEQ ID NO:78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

UGCUCCUCAC CCACA         15

( 2 ) INFORMATION FOR SEQ ID NO:79:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

ACACCAUCAG CCGCA         15

( 2 ) INFORMATION FOR SEQ ID NO:80:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

GCCGCAUCGC CGUCU         15

( 2 ) INFORMATION FOR SEQ ID NO:81:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:81:

UCGCCGUCUC CUACC 15

( 2 ) INFORMATION FOR SEQ ID NO:82:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:82:

GCCGUCUCCU ACCAG 15

( 2 ) INFORMATION FOR SEQ ID NO:83:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:83:

GUCUCCUACC AGACC 15

( 2 ) INFORMATION FOR SEQ ID NO:84:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:84:

CCAAGGUCAA CCUCC 15

( 2 ) INFORMATION FOR SEQ ID NO:85:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:85:

UCAACCUCCU CUCUG 15

( 2 ) INFORMATION FOR SEQ ID NO:86:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:86:

ACCUCCUCUC UGCCA 15

( 2 ) INFORMATION FOR SEQ ID NO:87:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:87:

CUCCUCUCUG CCAUC                                                                  15

(2) INFORMATION FOR SEQ ID NO:88:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:88:

CUGCCAUCAA GAGCC                                                                  15

(2) INFORMATION FOR SEQ ID NO:89:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:89:

CCCUGGUAUG AGCCC                                                                  15

(2) INFORMATION FOR SEQ ID NO:90:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:90:

AGCCCAUCUA UCUGG                                                                  15

(2) INFORMATION FOR SEQ ID NO:91:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:91:

CCCAUCUAUC UGGGA                                                                  15

(2) INFORMATION FOR SEQ ID NO:92:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:92:

CAUCUAUCUG GGAGG                                                                  15

(2) INFORMATION FOR SEQ ID NO:93:

(i) SEQUENCE CHARACTERISTICS:
      (A) LENGTH: 15 base pairs
      (B) TYPE: nucleic acid
      (C) STRANDEDNESS: single ( D ) TOPOLOGY: linear ( x i ) SEQUENCE DESCRIPTION: SEQ ID NO:93:

GAGGGGUCUU CCAGC 15

( 2 ) INFORMATION FOR SEQ ID NO:94:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

GGGGUCUUCC AGCUG 15

( 2 ) INFORMATION FOR SEQ ID NO:95:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

GGGUCUUCCA GCUGG 15

( 2 ) INFORMATION FOR SEQ ID NO:96:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

ACCGACUCAG CGCUG 15

( 2 ) INFORMATION FOR SEQ ID NO:97:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

CUGAGAUCAA UCGGC 15

( 2 ) INFORMATION FOR SEQ ID NO:98:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

GAUCAAUCGG CCCGA 15

( 2 ) INFORMATION FOR SEQ ID NO:99:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

CCCGACUAUC UCGAC                                                                                   15

( 2 ) INFORMATION FOR SEQ ID NO:100:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

CGACUAUCUC GACUU                                                                                   15

( 2 ) INFORMATION FOR SEQ ID NO:101:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

ACUAUCUCGA CUUUG                                                                                   15

( 2 ) INFORMATION FOR SEQ ID NO:102:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

CUCGACUUUG CCGAG                                                                                   15

( 2 ) INFORMATION FOR SEQ ID NO:103:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

UCGACUUUGC CGAGU                                                                                   15

( 2 ) INFORMATION FOR SEQ ID NO:104:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

GCCGAGUCUG GGCAG                                                                                   15

( 2 ) INFORMATION FOR SEQ ID NO:105:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

```
GGCAGGUCUA CUUUG                                                                     15
```

(2) INFORMATION FOR SEQ ID NO:106:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:106:

```
CAGGUCUACU UUGGG                                                                     15
```

(2) INFORMATION FOR SEQ ID NO:107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:107:

```
GUCUACUUUG GGAUC                                                                     15
```

(2) INFORMATION FOR SEQ ID NO:108:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:108:

```
UCUACUUUGG GAUCA                                                                     15
```

(2) INFORMATION FOR SEQ ID NO:109:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:109:

```
UUGGGAUCAU UGCCC                                                                     15
```

(2) INFORMATION FOR SEQ ID NO:110:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:110:

```
GGAUCAUUGC CCUGU                                                                     15
```

(2) INFORMATION FOR SEQ ID NO:111:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:111:

```
CGAACAUCCA ACCUU                                                                     15
```

( 2 ) INFORMATION FOR SEQ ID NO:112:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

CCAACCUUCC CAAAC     15

( 2 ) INFORMATION FOR SEQ ID NO:113:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

CAACCUUCCC AAACG     15

( 2 ) INFORMATION FOR SEQ ID NO:114:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

AACGCCUCCC CUGCC     15

( 2 ) INFORMATION FOR SEQ ID NO:115:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

CCCCAAUCCC UUUAU     15

( 2 ) INFORMATION FOR SEQ ID NO:116:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

AAUCCCUUUA UUACC     15

( 2 ) INFORMATION FOR SEQ ID NO:117:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

AUCCCUUUAU UACCC     15

( 2 ) INFORMATION FOR SEQ ID NO:118:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:118:

UCCCUUUAUU ACCCC 15

( 2 ) INFORMATION FOR SEQ ID NO:119:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:119:

CCUUUAUUAC CCCCU 15

( 2 ) INFORMATION FOR SEQ ID NO:120:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:120:

CUUUAUUACC CCCUC 15

( 2 ) INFORMATION FOR SEQ ID NO:121:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:121:

ACCCCUCCU UCAGA 15

( 2 ) INFORMATION FOR SEQ ID NO:122:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:122:

CCCUCCUUCA GACAC 15

( 2 ) INFORMATION FOR SEQ ID NO:123:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:123:

CCUCCUUCAG ACACC 15

( 2 ) INFORMATION FOR SEQ ID NO:124:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:124:

ACACCCUCAA CCUCU 15

(2) INFORMATION FOR SEQ ID NO:125:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:125:

UCAACCUCUU CUGGC 15

(2) INFORMATION FOR SEQ ID NO:126:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:126:

AACCUCUUCU GGCUC 15

(2) INFORMATION FOR SEQ ID NO:127:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:127:

ACCUCUUCUG GCUCA 15

(2) INFORMATION FOR SEQ ID NO:128:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:128:

UCUGGCUCAA AAAGA 15

(2) INFORMATION FOR SEQ ID NO:129:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:129:

AGAGAAUUGG GGGCU 15

(2) INFORMATION FOR SEQ ID NO:130:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:130:

GGGGGCUUAG GGUCG 15

( 2 ) INFORMATION FOR SEQ ID NO:131:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:131:

GGGGCUUAGG GUCGG 15

( 2 ) INFORMATION FOR SEQ ID NO:132:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:132:

UUAGGGUCGG AACCC 15

( 2 ) INFORMATION FOR SEQ ID NO:133:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:133:

CCAAGCUUAG AACUU 15

( 2 ) INFORMATION FOR SEQ ID NO:134:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:134:

CAAGCUUAGA ACUUU 15

( 2 ) INFORMATION FOR SEQ ID NO:135:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:135:

UAGAACUUUA AGCAA 15

( 2 ) INFORMATION FOR SEQ ID NO:136:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:136:

AGAACUUUAA GCAAC 15

( 2 ) INFORMATION FOR SEQ ID NO:137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

GAACUUUAAG CAACA 15

( 2 ) INFORMATION FOR SEQ ID NO:138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

CACCACUUCG AAACC 15

( 2 ) INFORMATION FOR SEQ ID NO:139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

ACCACUUCGA AACCU 15

( 2 ) INFORMATION FOR SEQ ID NO:140:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

CUGGGAUUCA GGAAU 15

( 2 ) INFORMATION FOR SEQ ID NO:141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

UGGGAUUCAG GAAUG 15

( 2 ) INFORMATION FOR SEQ ID NO:142:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

AACCACUAAG AAUUC         15

( 2 ) INFORMATION FOR SEQ ID NO:143:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

UAAGAAUUCA AACUG         15

( 2 ) INFORMATION FOR SEQ ID NO:144:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:144:

AAGAAUUCAA ACUGG         15

( 2 ) INFORMATION FOR SEQ ID NO:145:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:145:

GGGGCCUCCA GAACU         15

( 2 ) INFORMATION FOR SEQ ID NO:146:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:146:

CAGAACUCAC UGGGG         15

( 2 ) INFORMATION FOR SEQ ID NO:147:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:147:

GGGGCCUACA GCUUU         15

( 2 ) INFORMATION FOR SEQ ID NO:148:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:148:

UACAGCUUUG AUCCC         15

( 2 ) INFORMATION FOR SEQ ID NO:149:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:149:

ACAGCUUUGA UCCCU                                                                                                    15

( 2 ) INFORMATION FOR SEQ ID NO:150:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:150:

CUUUGAUCCC UGACA                                                                                                    15

( 2 ) INFORMATION FOR SEQ ID NO:151:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:151:

CUGACAUCUG GAAUC                                                                                                    15

( 2 ) INFORMATION FOR SEQ ID NO:152:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:152:

CUGGAAUCUG GAGAC                                                                                                    15

( 2 ) INFORMATION FOR SEQ ID NO:153:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:153:

GGAGCCUUUG GUUCU                                                                                                    15

( 2 ) INFORMATION FOR SEQ ID NO:154:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:154:

GAGCCUUUGG UUCUG                                                                                                    15

( 2 ) INFORMATION FOR SEQ ID NO:155:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:155:

CUUUGGUUCU GGCCA    15

( 2 ) INFORMATION FOR SEQ ID NO:156:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:156:

UUUGGUUCUG GCCAG    15

( 2 ) INFORMATION FOR SEQ ID NO:157:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

CAGGACUUGA GAAGA    15

( 2 ) INFORMATION FOR SEQ ID NO:158:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

AAGACCUCAC CUAGA    15

( 2 ) INFORMATION FOR SEQ ID NO:159:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

CUCACCUAGA AAUUG    15

( 2 ) INFORMATION FOR SEQ ID NO:160:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

UAGAAAUUGA CACAA    15

( 2 ) INFORMATION FOR SEQ ID NO:161:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:161:

UGGACCUUAG GCCUU 15

( 2 ) INFORMATION FOR SEQ ID NO:162:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:162:

GGACCUUAGG CCUUC 15

( 2 ) INFORMATION FOR SEQ ID NO:163:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:163:

UAGGCCUUCC UCUCU 15

( 2 ) INFORMATION FOR SEQ ID NO:164:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:164:

AGGCCUUCCU CUCUC 15

( 2 ) INFORMATION FOR SEQ ID NO:165:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:165:

CCUUCCUCUC UCCAG 15

( 2 ) INFORMATION FOR SEQ ID NO:166:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:166:

UUCCUCUCUC CAGAU 15

( 2 ) INFORMATION FOR SEQ ID NO:167:

( i ) SEQUENCE CHARACTERISTICS:
    ( A ) LENGTH: 15 base pairs (B) TYPE: nucleic acid
          (C) STRANDEDNESS: single
          (D) TOPOLOGY: linear (xi) SEQUENCE DESCRIPTION: SEQ ID NO:167:

CCUCUCUCCA GAUGU                                                                                        15

(2) INFORMATION FOR SEQ ID NO:168:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:168:

CAGAUGUUUC CAGAC                                                                                        15

(2) INFORMATION FOR SEQ ID NO:169:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:169:

AGAUGUUUCC AGACU                                                                                        15

(2) INFORMATION FOR SEQ ID NO:170:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:170:

GAUGUUUCCA GACUU                                                                                        15

(2) INFORMATION FOR SEQ ID NO:171:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:171:

CCAGACUUCC UUGAG                                                                                        15

(2) INFORMATION FOR SEQ ID NO:172:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO:172:

CAGACUUCCU UGAGA                                                                                        15

(2) INFORMATION FOR SEQ ID NO:173:

(i) SEQUENCE CHARACTERISTICS:
          (A) LENGTH: 15 base pairs
          (B) TYPE: nucleic acid
          (C) STRANDEDNESS: single ( D ) TOPOLOGY: linear ( x i ) SEQUENCE DESCRIPTION: SEQ ID NO:173:

ACUUCCUUGA GACAC  15

( 2 ) INFORMATION FOR SEQ ID NO:174:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

CAGCCCUCCC CAUGG  15

( 2 ) INFORMATION FOR SEQ ID NO:175:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

GCCAGCUCCC UCUAU  15

( 2 ) INFORMATION FOR SEQ ID NO:176:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

GCUCCCUCUA UUUAU  15

( 2 ) INFORMATION FOR SEQ ID NO:177:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

UCCCUCUAUU UAUGU  15

( 2 ) INFORMATION FOR SEQ ID NO:178:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

CCUCUAUUUA UGUUU  15

( 2 ) INFORMATION FOR SEQ ID NO:179:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

CUCUAUUUAU GUUUG						15

( 2 ) INFORMATION FOR SEQ ID NO:180:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

UCUAUUUAUG UUUGC						15

( 2 ) INFORMATION FOR SEQ ID NO:181:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:181:

UUUAUGUUUG CACUU						15

( 2 ) INFORMATION FOR SEQ ID NO:182:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

UUAUGUUUGC ACUUG						15

( 2 ) INFORMATION FOR SEQ ID NO:183:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:183:

UUGCACUUGU GAUUA						15

( 2 ) INFORMATION FOR SEQ ID NO:184:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:184:

UUGUGAUUAU UUAUU						15

( 2 ) INFORMATION FOR SEQ ID NO:185:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:185:

UGUGAUUAUU UAUUA                                                                  15

( 2 ) INFORMATION FOR SEQ ID NO:186:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:186:

UGAUUAUUUA UUAUU                                                                  15

( 2 ) INFORMATION FOR SEQ ID NO:187:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:187:

GAUUAUUUAU UAUUU                                                                  15

( 2 ) INFORMATION FOR SEQ ID NO:188:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:188:

AUUAUUUAUU AUUUA                                                                  15

( 2 ) INFORMATION FOR SEQ ID NO:189:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:189:

UAUUUAUUAU UUAUU                                                                  15

( 2 ) INFORMATION FOR SEQ ID NO:190:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:190:

AUUUAUUAUU UAUUU                                                                  15

( 2 ) INFORMATION FOR SEQ ID NO:191:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:191:

UUAUUAUUUA UUUAU                                                                  15

( 2 ) INFORMATION FOR SEQ ID NO:192:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:192:

U A U U A U U U A U  U U A U U           1 5

( 2 ) INFORMATION FOR SEQ ID NO:193:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:193:

A U U A U U U A U U  U A U U A           1 5

( 2 ) INFORMATION FOR SEQ ID NO:194:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

U A U U U A U U U A  U U A U U           1 5

( 2 ) INFORMATION FOR SEQ ID NO:195:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

A U U U A U U U A U  U A U U U           1 5

( 2 ) INFORMATION FOR SEQ ID NO:196:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

U U U A U U U A U U  A U U U A           1 5

( 2 ) INFORMATION FOR SEQ ID NO:197:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

U A U U U A U U A U  U U A U U           1 5

( 2 ) INFORMATION FOR SEQ ID NO:198:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:198:

AUUUAUUAUU UAUUU 15

( 2 ) INFORMATION FOR SEQ ID NO:199:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:199:

UUAUUAUUUA UUUAU 15

( 2 ) INFORMATION FOR SEQ ID NO:200:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:200:

UAUUAUUUAU UUAUU 15

( 2 ) INFORMATION FOR SEQ ID NO:201:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:201:

AUUAUUUAUU UAUUU 15

( 2 ) INFORMATION FOR SEQ ID NO:202:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:202:

UAUUUAUUUA UUUAC 15

( 2 ) INFORMATION FOR SEQ ID NO:203:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:203:

AUUUAUUUAU UUACA 15

( 2 ) INFORMATION FOR SEQ ID NO:204:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

UUUAUUUAUU UACAG 15

( 2 ) INFORMATION FOR SEQ ID NO:205:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

UAUUUAUUUA CAGAU 15

( 2 ) INFORMATION FOR SEQ ID NO:206:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

AUUUAUUUAC AGAUG 15

( 2 ) INFORMATION FOR SEQ ID NO:207:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

UUUAUUUACA GAUGA 15

( 2 ) INFORMATION FOR SEQ ID NO:208:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

UGAAUGUAUU UAUUU 15

( 2 ) INFORMATION FOR SEQ ID NO:209:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:209:

AAUGUAUUUA UUUGG 15

( 2 ) INFORMATION FOR SEQ ID NO:210:

( i ) SEQUENCE CHARACTERISTICS:
        ( A ) LENGTH: 15 base pairs
        ( B ) TYPE: nucleic acid ( C ) STRANDEDNESS: single
        ( D ) TOPOLOGY: linear ( x i ) SEQUENCE DESCRIPTION: SEQ ID NO:210:

AUGUAUUUAU UUGGG　　　　　　　　　　　　　　　　　　　　　　　　　　　　15

( 2 ) INFORMATION FOR SEQ ID NO:211:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:211:

UGUAUUUAUU UGGGA　　　　　　　　　　　　　　　　　　　　　　　　　　　　15

( 2 ) INFORMATION FOR SEQ ID NO:212:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:212:

UAUUUAUUUG GGAGA　　　　　　　　　　　　　　　　　　　　　　　　　　　　15

( 2 ) INFORMATION FOR SEQ ID NO:213:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

AUUUAUUUGG GAGAC　　　　　　　　　　　　　　　　　　　　　　　　　　　　15

( 2 ) INFORMATION FOR SEQ ID NO:214:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:214:

CCGGGGUAUC CUGGG　　　　　　　　　　　　　　　　　　　　　　　　　　　　15

( 2 ) INFORMATION FOR SEQ ID NO:215:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:215:

GGGGUAUCCU GGGGG　　　　　　　　　　　　　　　　　　　　　　　　　　　　15

( 2 ) INFORMATION FOR SEQ ID NO:216:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

CCAAUGUAGG AGCUG                              15

( 2 ) INFORMATION FOR SEQ ID NO:217:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

GCUGCCUUGG CUCAG                              15

( 2 ) INFORMATION FOR SEQ ID NO:218:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

CUUGGCUCAG ACAUG                              15

( 2 ) INFORMATION FOR SEQ ID NO:219:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

GACAUGUUUU CCGUG                              15

( 2 ) INFORMATION FOR SEQ ID NO:220:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

ACAUGUUUUC CGUGA                              15

( 2 ) INFORMATION FOR SEQ ID NO:221:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

CAUGUUUUCC GUGAA                              15

( 2 ) INFORMATION FOR SEQ ID NO:222:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

AUGUUUUCCG UGAAA                              15

( 2 ) INFORMATION FOR SEQ ID NO:223:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

GAACAAUAGG CUGUU                              15

( 2 ) INFORMATION FOR SEQ ID NO:224:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:224:

AGGCUGUUCC CAUGU                              15

( 2 ) INFORMATION FOR SEQ ID NO:225:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:225:

GGCUGUUCCC AUGUA                              15

( 2 ) INFORMATION FOR SEQ ID NO:226:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:226:

CCCAUGUAGC CCCCU                              15

( 2 ) INFORMATION FOR SEQ ID NO:227:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:227:

CUGGCCUCUG UGCCU                              15

( 2 ) INFORMATION FOR SEQ ID NO:228:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:228:

UGUGCCUUCU UUUGA                              15

( 2 ) INFORMATION FOR SEQ ID NO:229:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:229:

GUGCCUUCUU UUGAU     15

( 2 ) INFORMATION FOR SEQ ID NO:230:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:230:

GCCUUCUUUU GAUUA     15

( 2 ) INFORMATION FOR SEQ ID NO:231:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:231:

CCUUCUUUUG AUUAU     15

( 2 ) INFORMATION FOR SEQ ID NO:232:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:232:

CUUCUUUUGA UUAUG     15

( 2 ) INFORMATION FOR SEQ ID NO:233:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:233:

UUUUGAUUAU GUUUU     15

( 2 ) INFORMATION FOR SEQ ID NO:234:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:234:

UUUGAUUAUG UUUUU     15

( 2 ) INFORMATION FOR SEQ ID NO:235:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:235:

AUUAUGUUUU UUAAA                                    15

( 2 ) INFORMATION FOR SEQ ID NO:236:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:236:

UUAUGUUUUU UAAAA                                    15

( 2 ) INFORMATION FOR SEQ ID NO:237:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

UAUGUUUUU AAAAU                                      15

( 2 ) INFORMATION FOR SEQ ID NO:238:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:238:

UGUUUUUAA AAUAU                                      15

( 2 ) INFORMATION FOR SEQ ID NO:239:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:239:

GUUUUUAAA AUAUU                                      15

( 2 ) INFORMATION FOR SEQ ID NO:240:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:240:

UUAAAAUAUU AUCUG                                    15

( 2 ) INFORMATION FOR SEQ ID NO:241:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:241:

AAAAUAUUAU CUGAU 15

( 2 ) INFORMATION FOR SEQ ID NO:242:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:242:

AAAUAUUAUC UGAUU 15

( 2 ) INFORMATION FOR SEQ ID NO:243:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:243:

AUAUUAUCUG AUUAA 15

( 2 ) INFORMATION FOR SEQ ID NO:244:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:244:

AUCUGAUUAA GUUGU 15

( 2 ) INFORMATION FOR SEQ ID NO:245:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:245:

UCUGAUUAAG UUGUC 15

( 2 ) INFORMATION FOR SEQ ID NO:246:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:246:

AUUAAGUUGU CUAAA 15

( 2 ) INFORMATION FOR SEQ ID NO:247:

( i ) SEQUENCE CHARACTERISTICS:
    ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO:247:

AAGUUGUCUA AACAA 15

( 2 ) INFORMATION FOR SEQ ID NO:248:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:248:

GUUGUCUAAA CAAUG 15

( 2 ) INFORMATION FOR SEQ ID NO:249:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:249:

UGCUGAUUUG GUGAC 15

( 2 ) INFORMATION FOR SEQ ID NO:250:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:250:

GCUGAUUUGG UGACC 15

( 2 ) INFORMATION FOR SEQ ID NO:251:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:251:

CAACUGUCAC UCAUU 15

( 2 ) INFORMATION FOR SEQ ID NO:252:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:252:

UGUCACUCAU UGCUG 15

( 2 ) INFORMATION FOR SEQ ID NO:253:

( i ) SEQUENCE CHARACTERISTICS:
( A ) LENGTH: 15 base pairs
( B ) TYPE: nucleic acid
( C ) STRANDEDNESS: single ( D ) TOPOLOGY: linear ( x i ) SEQUENCE DESCRIPTION: SEQ ID NO:253:

CACUCAUUGC UGAGG 15

( 2 ) INFORMATION FOR SEQ ID NO:254:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

GAGGCCUCUG CUCCC 15

( 2 ) INFORMATION FOR SEQ ID NO:255:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

CUCUGCUCCC CAGGG 15

( 2 ) INFORMATION FOR SEQ ID NO:256:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

AGGGAGUUGU GUCUG 15

( 2 ) INFORMATION FOR SEQ ID NO:257:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:257:

GUUGUGUCUG UAAUC 15

( 2 ) INFORMATION FOR SEQ ID NO:258:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:258:

UGUCUGUAAU CGGCC 15

( 2 ) INFORMATION FOR SEQ ID NO:259:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:259:

CUGUAAUCGG CCUAC                                                                                         15

( 2 ) INFORMATION FOR SEQ ID NO:260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:260:

UCGGCCUACU AUUCA                                                                                         15

( 2 ) INFORMATION FOR SEQ ID NO:261:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:261:

GCCUACUAUU CAGUG                                                                                         15

( 2 ) INFORMATION FOR SEQ ID NO:262:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

CUACUAUUCA GUGGC                                                                                         15

( 2 ) INFORMATION FOR SEQ ID NO:263:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:263:

UACUAUUCAG UGGCG                                                                                         15

( 2 ) INFORMATION FOR SEQ ID NO:264:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:264:

GAGAAAUAAA GGUUG                                                                                         15

( 2 ) INFORMATION FOR SEQ ID NO:265:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:265:

UAAAGGUUGC UUAGG 15

(2) INFORMATION FOR SEQ ID NO:266:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:266:

GGUUGCUUAG GAAAG 15

(2) INFORMATION FOR SEQ ID NO:267:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:267:

GUUGCUUAGG AAAGA 15

(2) INFORMATION FOR SEQ ID NO:268:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:268:

GGAAGAGCUG AUGAGGCCGA AAGGCCGAAA CCUGCC 36

(2) INFORMATION FOR SEQ ID NO:269:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:269:

AGGAAGACUG AUGAGGCCGA AAGGCCGAAA ACCUGC 36

(2) INFORMATION FOR SEQ ID NO:270:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:270:

AGAGGAACUG AUGAGGCCGA AAGGCCGAAA GAACCU 36

(2) INFORMATION FOR SEQ ID NO:271:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:271:

UGAGAGGCUG AUGAGGCCGA AAGGCCGAAA GAGAAC 36

( 2 ) INFORMATION FOR SEQ ID NO:272:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:272:

GUGAGAGCUG AUGAGGCCGA AAGGCCGAAA AGAGAA     36

( 2 ) INFORMATION FOR SEQ ID NO:273:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:273:

UAUGUGACUG AUGAGGCCGA AAGGCCGAAA GGAAGA     36

( 2 ) INFORMATION FOR SEQ ID NO:274:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

AGUAUGUCUG AUGAGGCCGA AAGGCCGAAA GAGGAA     36

( 2 ) INFORMATION FOR SEQ ID NO:275:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

GGGUCAGCUG AUGAGGCCGA AAGGCCGAAA UGUGAG     36

( 2 ) INFORMATION FOR SEQ ID NO:276:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

GAGGUGCUG AUGAGGCCGA AAGGCCGAAA GCCGUG     36

( 2 ) INFORMATION FOR SEQ ID NO:277:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:277:

GGGGAGACUG AUGAGGCCGA AAGGCCGAAA GGGUGG     36

( 2 ) INFORMATION FOR SEQ ID NO:278:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:278:

CAGGGGACUG AUGAGGCCGA AAGGCCGAAA GAGGGU     36

( 2 ) INFORMATION FOR SEQ ID NO:279:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:279:

UCCAGGGCUG AUGAGGCCGA AAGGCCGAAA GAGAGG     36

( 2 ) INFORMATION FOR SEQ ID NO:280:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:280:

CGUCCCGCUG AUGAGGCCGA AAGGCCGAAA UCAUGC     36

( 2 ) INFORMATION FOR SEQ ID NO:281:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:281:

UCUUGGGCUG AUGAGGCCGA AAGGCCGAAA GCGCCU     36

( 2 ) INFORMATION FOR SEQ ID NO:282:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:282:

CCGCCUGCUG AUGAGGCCGA AAGGCCGAAA GCCCUG     36

( 2 ) INFORMATION FOR SEQ ID NO:283:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:283:

GAGGAACCUG AUGAGGCCGA AAGGCCGAAA GCACCG     36

( 2 ) INFORMATION FOR SEQ ID NO:284:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:284:

GCUGAGGCUG AUGAGGCCGA AAGGCCGAAA CAAGCA 36

(2) INFORMATION FOR SEQ ID NO:285:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:285:

GGCUGAGCUG AUGAGGCCGA AAGGCCGAAA ACAAGC 36

(2) INFORMATION FOR SEQ ID NO:286:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:286:

AGAGGCUCUG AUGAGGCCGA AAGGCCGAAA GGAACA 36

(2) INFORMATION FOR SEQ ID NO:287:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:287:

AGGAGAACUG AUGAGGCCGA AAGGCCGAAA GGCUGA 36

(2) INFORMATION FOR SEQ ID NO:288:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:288:

GAAGGAGCUG AUGAGGCCGA AAGGCCGAAA GAGGCU 36

(2) INFORMATION FOR SEQ ID NO:289:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:289:

GGAAGGACUG AUGAGGCCGA AAGGCCGAAA AGAGGC 36

(2) INFORMATION FOR SEQ ID NO:290:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:290:

CAGGAAGCUG AUGAGGCCGA AAGGCCGAAA GAAGAG    36

(2) INFORMATION FOR SEQ ID NO:291:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:291:

GAUCAGGCUG AUGAGGCCGA AAGGCCGAAA GGAGAA    36

(2) INFORMATION FOR SEQ ID NO:292:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:292:

CGAUCAGCUG AUGAGGCCGA AAGGCCGAAA AGGAGA    36

(2) INFORMATION FOR SEQ ID NO:293:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:293:

CUGCCACCUG AUGAGGCCGA AAGGCCGAAA UCAGGA    36

(2) INFORMATION FOR SEQ ID NO:294:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:294:

GGCAGAACUG AUGAGGCCGA AAGGCCGAAA GCGUGG    36

(2) INFORMATION FOR SEQ ID NO:295:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:295:

CAGGCAGCUG AUGAGGCCGA AAGGCCGAAA GAGCGU    36

(2) INFORMATION FOR SEQ ID NO:296:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO:296:

GCAGGCACUG AUGAGGCCGA AAGGCCGAAA AGAGCG    36

( 2 ) INFORMATION FOR SEQ ID NO:297:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:297:

CACUCCACUG AUGAGGCCGA AAGGCCGAAA GUGCAG    36

( 2 ) INFORMATION FOR SEQ ID NO:298:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:298:

UCACUCCCUG AUGAGGCCGA AAGGCCGAAA AGUGCA    36

( 2 ) INFORMATION FOR SEQ ID NO:299:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:299:

GGGGGCCCUG AUGAGGCCGA AAGGCCGAAA UCACUC    36

( 2 ) INFORMATION FOR SEQ ID NO:300:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:300:

CCUGGGGCUG AUGAGGCCGA AAGGCCGAAA CUCUUC    36

( 2 ) INFORMATION FOR SEQ ID NO:301:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

UUAGAGACUG AUGAGGCCGA AAGGCCGAAA GGUCCC    36

( 2 ) INFORMATION FOR SEQ ID NO:302:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:302:

GAUUAGACUG AUGAGGCCGA AAGGCCGAAA GAGGUC                                      36

( 2 ) INFORMATION FOR SEQ ID NO:303:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

CUGAUUACUG AUGAGGCCGA AAGGCCGAAA GAGAGG                                      36

( 2 ) INFORMATION FOR SEQ ID NO:304:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:304:

GGCUGAUCUG AUGAGGCCGA AAGGCCGAAA GAGAGA                                      36

( 2 ) INFORMATION FOR SEQ ID NO:305:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

GAGGGCUCUG AUGAGGCCGA AAGGCCGAAA UUAGAG                                      36

( 2 ) INFORMATION FOR SEQ ID NO:306:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

UGGGCCACUG AUGAGGCCGA AAGGCCGAAA GGGCUG                                      36

( 2 ) INFORMATION FOR SEQ ID NO:307:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

AGAAGAUCUG AUGAGGCCGA AAGGCCGAAA UCUGAC                                      36

( 2 ) INFORMATION FOR SEQ ID NO:308:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:308:

UCGAGAACUG AUGAGGCCGA AAGGCCGAAA UGAUCU                                      36

( 2 ) INFORMATION FOR SEQ ID NO:309:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:309:

GUUCGAGCUG AUGAGGCCGA AAGGCCGAAA GAUGAU     36

( 2 ) INFORMATION FOR SEQ ID NO:310:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:310:

GGUUCGACUG AUGAGGCCGA AAGGCCGAAA AGAUGA     36

( 2 ) INFORMATION FOR SEQ ID NO:311:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:311:

GGGGUUCCUG AUGAGGCCGA AAGGCCGAAA GAAGAU     36

( 2 ) INFORMATION FOR SEQ ID NO:312:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:312:

CAUGGGCCUG AUGAGGCCGA AAGGCCGAAA CAGGCU     36

( 2 ) INFORMATION FOR SEQ ID NO:313:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:313:

UUGCUACCUG AUGAGGCCGA AAGGCCGAAA CAUGGG     36

( 2 ) INFORMATION FOR SEQ ID NO:314:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:314:

GGUUUGCCUG AUGAGGCCGA AAGGCCGAAA CAACAU     36

( 2 ) INFORMATION FOR SEQ ID NO:315:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:315:

UCAGCUUCUG AUGAGGCCGA AAGGCCGAAA GGGUUU      36

( 2 ) INFORMATION FOR SEQ ID NO:316:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:316:

GCCACUGCUG AUGAGGCCGA AAGGCCGAAA GCUGCC      36

( 2 ) INFORMATION FOR SEQ ID NO:317:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:317:

UGGCCAGCUG AUGAGGCCGA AAGGCCGAAA GGGCAU      36

( 2 ) INFORMATION FOR SEQ ID NO:318:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:318:

AGCUGGUCUG AUGAGGCCGA AAGGCCGAAA UCUCUC      36

( 2 ) INFORMATION FOR SEQ ID NO:319:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:319:

GCCCUCUCUG AUGAGGCCGA AAGGCCGAAA UGGCAC      36

( 2 ) INFORMATION FOR SEQ ID NO:320:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:320:

GAUGAGGCUG AUGAGGCCGA AAGGCCGAAA CAGGCC      36

( 2 ) INFORMATION FOR SEQ ID NO:321:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:321:

AGUAGAUCUG AUGAGGCCGA AAGGCCGAAA GGUACA 36

( 2 ) INFORMATION FOR SEQ ID NO:322:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:322:

GGGAGUACUG AUGAGGCCGA AAGGCCGAAA UGAGGU 36

( 2 ) INFORMATION FOR SEQ ID NO:323:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:323:

CUGGGAGCUG AUGAGGCCGA AAGGCCGAAA GAUGAG 36

( 2 ) INFORMATION FOR SEQ ID NO:324:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:324:

GACCUGGCUG AUGAGGCCGA AAGGCCGAAA GUAGAU 36

( 2 ) INFORMATION FOR SEQ ID NO:325:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:325:

UGAAGAGCUG AUGAGGCCGA AAGGCCGAAA CCUGGG 36

( 2 ) INFORMATION FOR SEQ ID NO:326:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:326:

CCUUGAACUG AUGAGGCCGA AAGGCCGAAA GGACCU 36

( 2 ) INFORMATION FOR SEQ ID NO:327:

( i ) SEQUENCE CHARACTERISTICS:
    ( A ) LENGTH: 36 base pairs (B) TYPE: nucleic acid
            (C) STRANDEDNESS: single
            (D) TOPOLOGY: linear (xi) SEQUENCE DESCRIPTION: SEQ ID NO:327:

GCCCUUGCUG AUGAGGCCGA AAGGCCGAAA GAGGAC    36

(2) INFORMATION FOR SEQ ID NO:328:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:328:

GGCCCUUCUG AUGAGGCCGA AAGGCCGAAA AGAGGA    36

(2) INFORMATION FOR SEQ ID NO:329:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:329:

AUGGGUGCUG AUGAGGCCGA AAGGCCGAAA GGGGCA    36

(2) INFORMATION FOR SEQ ID NO:330:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:330:

GGGUGAGCUG AUGAGGCCGA AAGGCCGAAA GCACAU    36

(2) INFORMATION FOR SEQ ID NO:331:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:331:

UGUGGGUCUG AUGAGGCCGA AAGGCCGAAA GGAGCA    36

(2) INFORMATION FOR SEQ ID NO:332:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:332:

UGCGGCUCUG AUGAGGCCGA AAGGCCGAAA UGGUGU    36

(2) INFORMATION FOR SEQ ID NO:333:

(i) SEQUENCE CHARACTERISTICS:
            (A) LENGTH: 36 base pairs
            (B) TYPE: nucleic acid
            (C) STRANDEDNESS: single (D) TOPOLOGY: linear (x i) SEQUENCE DESCRIPTION: SEQ ID NO:333:

AGACGGCCUG AUGAGGCCGA AAGGCCGAAA UGCGGC  36

(2) INFORMATION FOR SEQ ID NO:334:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:334:

GGUAGGACUG AUGAGGCCGA AAGGCCGAAA CGGCGA  36

(2) INFORMATION FOR SEQ ID NO:335:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:335:

CUGGUAGCUG AUGAGGCCGA AAGGCCGAAA GACGGC  36

(2) INFORMATION FOR SEQ ID NO:336:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:336:

GGUCUGGCUG AUGAGGCCGA AAGGCCGAAA GGAGAC  36

(2) INFORMATION FOR SEQ ID NO:337:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:337:

GGAGGUUCUG AUGAGGCCGA AAGGCCGAAA CCUUGG  36

(2) INFORMATION FOR SEQ ID NO:338:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:338:

CAGAGAGCUG AUGAGGCCGA AAGGCCGAAA GGUUGA  36

(2) INFORMATION FOR SEQ ID NO:339:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:339:

UGGCAGACUG AUGAGGCCGA AAGGCCGAAA GGAGGU     36

( 2 ) INFORMATION FOR SEQ ID NO:340:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

GAUGGCACUG AUGAGGCCGA AAGGCCGAAA GAGGAG     36

( 2 ) INFORMATION FOR SEQ ID NO:341:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:341:

GGCUCUUCUG AUGAGGCCGA AAGGCCGAAA UGGCAG     36

( 2 ) INFORMATION FOR SEQ ID NO:342:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:342:

GGGCUCACUG AUGAGGCCGA AAGGCCGAAA CCAGGG     36

( 2 ) INFORMATION FOR SEQ ID NO:343:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:343:

CCAGAUACUG AUGAGGCCGA AAGGCCGAAA UGGGCU     36

( 2 ) INFORMATION FOR SEQ ID NO:344:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:344:

UCCCAGACUG AUGAGGCCGA AAGGCCGAAA GAUGGG     36

( 2 ) INFORMATION FOR SEQ ID NO:345:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:345:

```
CCUCCCACUG  AUGAGGCCGA  AAGGCCGAAA  UAGAUG                              36
```

( 2 ) INFORMATION FOR SEQ ID NO:346:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:346:

```
GCUGGAACUG  AUGAGGCCGA  AAGGCCGAAA  CCCCUC                              36
```

( 2 ) INFORMATION FOR SEQ ID NO:347:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:347:

```
CAGCUGGCUG  AUGAGGCCGA  AAGGCCGAAA  GACCCC                              36
```

( 2 ) INFORMATION FOR SEQ ID NO:348:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:348:

```
CCAGCUGCUG  AUGAGGCCGA  AAGGCCGAAA  AGACCC                              36
```

( 2 ) INFORMATION FOR SEQ ID NO:349:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:349:

```
CAGCGCUCUG  AUGAGGCCGA  AAGGCCGAAA  GUCGGU                              36
```

( 2 ) INFORMATION FOR SEQ ID NO:350:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:350:

```
GCCGAUUCUG  AUGAGGCCGA  AAGGCCGAAA  UCUCAG                              36
```

( 2 ) INFORMATION FOR SEQ ID NO:351:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:351:

```
UCGGGCCCUG  AUGAGGCCGA  AAGGCCGAAA  UUGAUC                              36
```

( 2 ) INFORMATION FOR SEQ ID NO:352:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:352:

GUCGAGACUG AUGAGGCCGA AAGGCCGAAA GUCGGG    36

( 2 ) INFORMATION FOR SEQ ID NO:353:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:353:

AAGUCGACUG AUGAGGCCGA AAGGCCGAAA UAGUCG    36

( 2 ) INFORMATION FOR SEQ ID NO:354:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:354:

CAAAGUCCUG AUGAGGCCGA AAGGCCGAAA GAUAGU    36

( 2 ) INFORMATION FOR SEQ ID NO:355:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:355:

CUCGGCACUG AUGAGGCCGA AAGGCCGAAA GUCGAG    36

( 2 ) INFORMATION FOR SEQ ID NO:356:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:356:

ACUCGGCCUG AUGAGGCCGA AAGGCCGAAA AGUCGA    36

( 2 ) INFORMATION FOR SEQ ID NO:357:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:357:

CUGCCCACUG AUGAGGCCGA AAGGCCGAAA CUCGGC    36

( 2 ) INFORMATION FOR SEQ ID NO:358:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:358:

CAAAGUACUG AUGAGGCCGA AAGGCCGAAA CCUGCC    36

( 2 ) INFORMATION FOR SEQ ID NO:359:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:359:

CCCAAAGCUG AUGAGGCCGA AAGGCCGAAA GACCUG    36

( 2 ) INFORMATION FOR SEQ ID NO:360:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:360:

GAUCCCACUG AUGAGGCCGA AAGGCCGAAA GUAGAC    36

( 2 ) INFORMATION FOR SEQ ID NO:361:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:361:

UGAUCCCUG AUGAGGCCGA AAGGCCGAAA AGUAGA    36

( 2 ) INFORMATION FOR SEQ ID NO:362:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:362:

GGGCAAUCUG AUGAGGCCGA AAGGCCGAAA UCCCAA    36

( 2 ) INFORMATION FOR SEQ ID NO:363:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:363:

ACAGGGCCUG AUGAGGCCGA AAGGCCGAAA UGAUCC    36

( 2 ) INFORMATION FOR SEQ ID NO:364:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:364:

AAGGUUGCUG AUGAGGCCGA AAGGCCGAAA UGUUCG    36

(2) INFORMATION FOR SEQ ID NO:365:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:365:

GUUUGGGCUG AUGAGGCCGA AAGGCCGAAA GGUUGG    36

(2) INFORMATION FOR SEQ ID NO:366:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:366:

CGUUUGGCUG AUGAGGCCGA AAGGCCGAAA AGGUUG    36

(2) INFORMATION FOR SEQ ID NO:367:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:367:

GGCAGGGCUG AUGAGGCCGA AAGGCCGAAA GGCGUU    36

(2) INFORMATION FOR SEQ ID NO:368:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:368:

AUAAAGGCUG AUGAGGCCGA AAGGCCGAAA UUGGGG    36

(2) INFORMATION FOR SEQ ID NO:369:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:369:

GGUAAUACUG AUGAGGCCGA AAGGCCGAAA GGGAUU    36

(2) INFORMATION FOR SEQ ID NO:370:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:370:

GGGUAAUCUG AUGAGGCCGA AAGGCCGAAA AGGGAU 36

( 2 ) INFORMATION FOR SEQ ID NO:371:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:371:

GGGGUAACUG AUGAGGCCGA AAGGCCGAAA AAGGGA 36

( 2 ) INFORMATION FOR SEQ ID NO:372:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:372:

AGGGGGUCUG AUGAGGCCGA AAGGCCGAAA UAAAGG 36

( 2 ) INFORMATION FOR SEQ ID NO:373:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:373:

GAGGGGGCUG AUGAGGCCGA AAGGCCGAAA AUAAAG 36

( 2 ) INFORMATION FOR SEQ ID NO:374:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:374:

UCUGAAGCUG AUGAGGCCGA AAGGCCGAAA GGGGGU 36

( 2 ) INFORMATION FOR SEQ ID NO:375:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:375:

GUGUCUGCUG AUGAGGCCGA AAGGCCGAAA GGAGGG 36

( 2 ) INFORMATION FOR SEQ ID NO:376:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:376:

GGUGUCUCUG AUGAGGCCGA AAGGCCGAAA AGGAGG  36

( 2 ) INFORMATION FOR SEQ ID NO:377:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:377:

AGAGGUUCUG AUGAGGCCGA AAGGCCGAAA GGGUGU  36

( 2 ) INFORMATION FOR SEQ ID NO:378:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:378:

GCCAGAACUG AUGAGGCCGA AAGGCCGAAA GGUUGA  36

( 2 ) INFORMATION FOR SEQ ID NO:379:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:379:

GAGCCAGCUG AUGAGGCCGA AAGGCCGAAA GAGGUU  36

( 2 ) INFORMATION FOR SEQ ID NO:380:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:380:

UGAGCCACUG AUGAGGCCGA AAGGCCGAAA AGAGGU  36

( 2 ) INFORMATION FOR SEQ ID NO:381:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:381:

UCUUUUUCUG AUGAGGCCGA AAGGCCGAAA GCCAGA  36

( 2 ) INFORMATION FOR SEQ ID NO:382:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:382:

AGCCCCCUG AUGAGGCCGA AAGGCCGAAA UUCUCU 36

( 2 ) INFORMATION FOR SEQ ID NO:383:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:383:

CGACCCUCUG AUGAGGCCGA AAGGCCGAAA GCCCCC 36

( 2 ) INFORMATION FOR SEQ ID NO:384:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:384:

CCGACCCCUG AUGAGGCCGA AAGGCCGAAA AGCCCC 36

( 2 ) INFORMATION FOR SEQ ID NO:385:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:385:

GGGUUCCCUG AUGAGGCCGA AAGGCCGAAA CCCUAA 36

( 2 ) INFORMATION FOR SEQ ID NO:386:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:386:

AAGUUCUCUG AUGAGGCCGA AAGGCCGAAA GCUUGG 36

( 2 ) INFORMATION FOR SEQ ID NO:387:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:387:

AAAGUUCCUG AUGAGGCCGA AAGGCCGAAA AGCUUG 36

( 2 ) INFORMATION FOR SEQ ID NO:388:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:388:

UUGCUUACUG AUGAGGCCGA AAGGCCGAAA GUUCUA 36

( 2 ) INFORMATION FOR SEQ ID NO:389:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

GUUGCUUCUG AUGAGGCCGA AAGGCCGAAA AGUUCU    36

( 2 ) INFORMATION FOR SEQ ID NO:390:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:390:

UGUUGCUCUG AUGAGGCCGA AAGGCCGAAA AAGUUC    36

( 2 ) INFORMATION FOR SEQ ID NO:391:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

GGUUUCGCUG AUGAGGCCGA AAGGCCGAAA GUGGUG    36

( 2 ) INFORMATION FOR SEQ ID NO:392:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

AGGUUUCCUG AUGAGGCCGA AAGGCCGAAA AGUGGU    36

( 2 ) INFORMATION FOR SEQ ID NO:393:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

AUUCCUGCUG AUGAGGCCGA AAGGCCGAAA UCCCAG    36

( 2 ) INFORMATION FOR SEQ ID NO:394:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

CAUUCCUCUG AUGAGGCCGA AAGGCCGAAA AUCCCA    36

( 2 ) INFORMATION FOR SEQ ID NO:395:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

GAAUUCUCUG AUGAGGCCGA AAGGCCGAAA GUGGUU                      36

( 2 ) INFORMATION FOR SEQ ID NO:396:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:396:

CAGUUUGCUG AUGAGGCCGA AAGGCCGAAA UUCUUA                      36

( 2 ) INFORMATION FOR SEQ ID NO:397:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:397:

CCAGUUUCUG AUGAGGCCGA AAGGCCGAAA AUUCUU                      36

( 2 ) INFORMATION FOR SEQ ID NO:398:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:398:

AGUUCUGCUG AUGAGGCCGA AAGGCCGAAA GGCCCC                      36

( 2 ) INFORMATION FOR SEQ ID NO:399:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:399:

CCCCAGUCUG AUGAGGCCGA AAGGCCGAAA GUUCUG                      36

( 2 ) INFORMATION FOR SEQ ID NO:400:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:400:

AAAGCUGCUG AUGAGGCCGA AAGGCCGAAA GGCCCC                      36

( 2 ) INFORMATION FOR SEQ ID NO:401:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:401:

GGGAUCACUG AUGAGGCCGA AAGGCCGAAA GCUGUA      36

( 2 ) INFORMATION FOR SEQ ID NO:402:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:402:

AGGGAUCCUG AUGAGGCCGA AAGGCCGAAA AGCUGU      36

( 2 ) INFORMATION FOR SEQ ID NO:403:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:403:

UGUCAGGCUG AUGAGGCCGA AAGGCCGAAA UCAAAG      36

( 2 ) INFORMATION FOR SEQ ID NO:404:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:404:

GAUUCCACUG AUGAGGCCGA AAGGCCGAAA UGUCAG      36

( 2 ) INFORMATION FOR SEQ ID NO:405:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

GUCUCCACUG AUGAGGCCGA AAGGCCGAAA UUCCAG      36

( 2 ) INFORMATION FOR SEQ ID NO:406:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

AGAACCACUG AUGAGGCCGA AAGGCCGAAA GGCUCC      36

( 2 ) INFORMATION FOR SEQ ID NO:407:

( i ) SEQUENCE CHARACTERISTICS:
        ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO:407:

CAGAACCCUG AUGAGGCCGA AAGGCCGAAA AGGCUC 36

( 2 ) INFORMATION FOR SEQ ID NO:408:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:408:

UGGCCAGCUG AUGAGGCCGA AAGGCCGAAA CCAAAG 36

( 2 ) INFORMATION FOR SEQ ID NO:409:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:409:

CUGGCCACUG AUGAGGCCGA AAGGCCGAAA ACCAAA 36

( 2 ) INFORMATION FOR SEQ ID NO:410:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:410:

UCUUCUCCUG AUGAGGCCGA AAGGCCGAAA GUCCUG 36

( 2 ) INFORMATION FOR SEQ ID NO:411:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:411:

UCUAGGUCUG AUGAGGCCGA AAGGCCGAAA GGUCUU 36

( 2 ) INFORMATION FOR SEQ ID NO:412:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:412:

CAAUUCCUG AUGAGGCCGA AAGGCCGAAA GGUGAG 36

( 2 ) INFORMATION FOR SEQ ID NO:413:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (xi) SEQUENCE DESCRIPTION: SEQ ID NO:413:

UUGUGUCCUG AUGAGGCCGA AAGGCCGAAA UUUCUA 36

(2) INFORMATION FOR SEQ ID NO:414:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:414:

AAGGCCUCUG AUGAGGCCGA AAGGCCGAAA GGUCCA 36

(2) INFORMATION FOR SEQ ID NO:415:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:415:

GAAGGCCCUG AUGAGGCCGA AAGGCCGAAA AGGUCC 36

(2) INFORMATION FOR SEQ ID NO:416:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:416:

AGAGAGGCUG AUGAGGCCGA AAGGCCGAAA GGCCUA 36

(2) INFORMATION FOR SEQ ID NO:417:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:417:

GAGAGAGCUG AUGAGGCCGA AAGGCCGAAA AGGCCU 36

(2) INFORMATION FOR SEQ ID NO:418:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:418:

CUGGAGACUG AUGAGGCCGA AAGGCCGAAA GGAAGG 36

(2) INFORMATION FOR SEQ ID NO:419:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:419:

AUCUGGACUG AUGAGGCCGA AAGGCCGAAA GAGGAA                                36

(2) INFORMATION FOR SEQ ID NO:420:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:420:

ACAUCUGCUG AUGAGGCCGA AAGGCCGAAA GAGAGG                                36

(2) INFORMATION FOR SEQ ID NO:421:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:421:

GUCUGGACUG AUGAGGCCGA AAGGCCGAAA CAUCUG                                36

(2) INFORMATION FOR SEQ ID NO:422:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:422:

AGUCUGGCUG AUGAGGCCGA AAGGCCGAAA ACAUCU                                36

(2) INFORMATION FOR SEQ ID NO:423:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:423:

AAGUCUGCUG AUGAGGCCGA AAGGCCGAAA AACAUC                                36

(2) INFORMATION FOR SEQ ID NO:424:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:424:

CUCAAGGCUG AUGAGGCCGA AAGGCCGAAA GUCUGG                                36

(2) INFORMATION FOR SEQ ID NO:425:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:425:

```
UCUCAAGCUG  AUGAGGCCGA  AAGGCCGAAA  AGUCUG                                     36
```

( 2 ) INFORMATION FOR SEQ ID NO:426:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:426:

```
GUGUCUCCUG  AUGAGGCCGA  AAGGCCGAAA  GGAAGU                                     36
```

( 2 ) INFORMATION FOR SEQ ID NO:427:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:427:

```
CCAUGGGCUG  AUGAGGCCGA  AAGGCCGAAA  GGGCUG                                     36
```

( 2 ) INFORMATION FOR SEQ ID NO:428:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:428:

```
AUAGAGGCUG  AUGAGGCCGA  AAGGCCGAAA  GCUGGC                                     36
```

( 2 ) INFORMATION FOR SEQ ID NO:429:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:429:

```
AUAAAUACUG  AUGAGGCCGA  AAGGCCGAAA  GGGAGC                                     36
```

( 2 ) INFORMATION FOR SEQ ID NO:430:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:430:

```
ACAUAAACUG  AUGAGGCCGA  AAGGCCGAAA  GAGGGA                                     36
```

( 2 ) INFORMATION FOR SEQ ID NO:431:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:431:

```
AAACAUACUG  AUGAGGCCGA  AAGGCCGAAA  UAGAGG                                     36
```

( 2 ) INFORMATION FOR SEQ ID NO:432:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:432:

CAAACAUCUG AUGAGGCCGA AAGGCCGAAA AUAGAG       36

( 2 ) INFORMATION FOR SEQ ID NO:433:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:433:

GCAAACACUG AUGAGGCCGA AAGGCCGAAA AAUAGA       36

( 2 ) INFORMATION FOR SEQ ID NO:434:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

AAGUGCACUG AUGAGGCCGA AAGGCCGAAA CAUAAA       36

( 2 ) INFORMATION FOR SEQ ID NO:435:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:435:

CAAGUGCCUG AUGAGGCCGA AAGGCCGAAA ACAUAA       36

( 2 ) INFORMATION FOR SEQ ID NO:436:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:436:

UAAUCACCUG AUGAGGCCGA AAGGCCGAAA GUGCAA       36

( 2 ) INFORMATION FOR SEQ ID NO:437:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:437:

AAUAAAUCUG AUGAGGCCGA AAGGCCGAAA UCACAA       36

( 2 ) INFORMATION FOR SEQ ID NO:438:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:438:

UAAUAAACUG AUGAGGCCGA AAGGCCGAAA AUCACA                36

( 2 ) INFORMATION FOR SEQ ID NO:439:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:439:

AAUAAUACUG AUGAGGCCGA AAGGCCGAAA UAAUCA                36

( 2 ) INFORMATION FOR SEQ ID NO:440:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:440:

AAAUAAUCUG AUGAGGCCGA AAGGCCGAAA AUAAUC                36

( 2 ) INFORMATION FOR SEQ ID NO:441:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:441:

UAAAUAACUG AUGAGGCCGA AAGGCCGAAA AAUAAU                36

( 2 ) INFORMATION FOR SEQ ID NO:442:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:442:

AAUAAAUCUG AUGAGGCCGA AAGGCCGAAA UAAAUA                36

( 2 ) INFORMATION FOR SEQ ID NO:443:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:443:

AAAUAAACUG AUGAGGCCGA AAGGCCGAAA AUAAAU                36

( 2 ) INFORMATION FOR SEQ ID NO:444:

( i ) SEQUENCE CHARACTERISTICS:

( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:444:

AUAAAUACUG AUGAGGCCGA AAGGCCGAAA UAAUAA                                          36

( 2 ) INFORMATION FOR SEQ ID NO:445:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:445:

AAUAAAUCUG AUGAGGCCGA AAGGCCGAAA AUAAUA                                          36

( 2 ) INFORMATION FOR SEQ ID NO:446:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:446:

UAAUAAACUG AUGAGGCCGA AAGGCCGAAA AAUAAU                                          36

( 2 ) INFORMATION FOR SEQ ID NO:447:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:447:

AAUAAUACUG AUGAGGCCGA AAGGCCGAAA UAAAUA                                          36

( 2 ) INFORMATION FOR SEQ ID NO:448:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:448:

AAAUAAUCUG AUGAGGCCGA AAGGCCGAAA AUAAAU                                          36

( 2 ) INFORMATION FOR SEQ ID NO:449:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( x i ) SEQUENCE DESCRIPTION: SEQ ID NO:449:

UAAAUAACUG AUGAGGCCGA AAGGCCGAAA AAUAAA                                          36

( 2 ) INFORMATION FOR SEQ ID NO:450:

( i ) SEQUENCE CHARACTERISTICS:
               ( A ) LENGTH: 36 base pairs
               ( B ) TYPE: nucleic acid ( C ) STRANDEDNESS: single
        ( D ) TOPOLOGY: linear ( x i ) SEQUENCE DESCRIPTION: SEQ ID NO:450:

AAUAAAUCUG AUGAGGCCGA AAGGCCGAAA UAAAUA 36

( 2 ) INFORMATION FOR SEQ ID NO:451:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:451:

AAAUAAACUG AUGAGGCCGA AAGGCCGAAA AUAAAU 36

( 2 ) INFORMATION FOR SEQ ID NO:452:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

AUAAAUACUG AUGAGGCCGA AAGGCCGAAA UAAUAA 36

( 2 ) INFORMATION FOR SEQ ID NO:453:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

AAUAAAUCUG AUGAGGCCGA AAGGCCGAAA AUAAUA 36

( 2 ) INFORMATION FOR SEQ ID NO:454:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:454:

AAAUAAACUG AUGAGGCCGA AAGGCCGAAA AAUAAU 36

( 2 ) INFORMATION FOR SEQ ID NO:455:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:455:

GUAAAUACUG AUGAGGCCGA AAGGCCGAAA UAAAUA 36

( 2 ) INFORMATION FOR SEQ ID NO:456:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:456:

UGUAAAUCUG AUGAGGCCGA AAGGCCGAAA AUAAAU 36

( 2 ) INFORMATION FOR SEQ ID NO:457:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:457:

CUGUAAACUG AUGAGGCCGA AAGGCCGAAA AAUAAA 36

( 2 ) INFORMATION FOR SEQ ID NO:458:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:458:

AUCUGUACUG AUGAGGCCGA AAGGCCGAAA UAAAUA 36

( 2 ) INFORMATION FOR SEQ ID NO:459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:459:

CAUCUGUCUG AUGAGGCCGA AAGGCCGAAA AUAAAU 36

( 2 ) INFORMATION FOR SEQ ID NO:460:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:460:

UCAUCUGCUG AUGAGGCCGA AAGGCCGAAA AAUAAA 36

( 2 ) INFORMATION FOR SEQ ID NO:461:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:461:

AAAUAAACUG AUGAGGCCGA AAGGCCGAAA CAUUCA 36

( 2 ) INFORMATION FOR SEQ ID NO:462:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:462:

CCAAAUACUG AUGAGGCCGA AAGGCCGAAA UACAUU 36

( 2 ) INFORMATION FOR SEQ ID NO:463:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:463:

CCCAAAUCUG AUGAGGCCGA AAGGCCGAAA AUACAU 36

( 2 ) INFORMATION FOR SEQ ID NO:464:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:464:

UCCCAAACUG AUGAGGCCGA AAGGCCGAAA AAUACA 36

( 2 ) INFORMATION FOR SEQ ID NO:465:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:465:

UCUCCCACUG AUGAGGCCGA AAGGCCGAAA UAAAUA 36

( 2 ) INFORMATION FOR SEQ ID NO:466:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:466:

GUCUCCCCUG AUGAGGCCGA AAGGCCGAAA AUAAAU 36

( 2 ) INFORMATION FOR SEQ ID NO:467:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:467:

CCCAGGACUG AUGAGGCCGA AAGGCCGAAA CCCCGG 36

( 2 ) INFORMATION FOR SEQ ID NO:468:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:468:

CCCCCAGCUG AUGAGGCCGA AAGGCCGAAA UACCCC 36

( 2 ) INFORMATION FOR SEQ ID NO:469:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:469:

CAGCUCCCUG AUGAGGCCGA AAGGCCGAAA CAUUGG        36

( 2 ) INFORMATION FOR SEQ ID NO:470:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:470:

CUGAGCCCUG AUGAGGCCGA AAGGCCGAAA GGCAGC        36

( 2 ) INFORMATION FOR SEQ ID NO:471:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:471:

CAUGUCUCUG AUGAGGCCGA AAGGCCGAAA GCCAAG        36

( 2 ) INFORMATION FOR SEQ ID NO:472:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:472:

CACGGAACUG AUGAGGCCGA AAGGCCGAAA CAUGUC        36

( 2 ) INFORMATION FOR SEQ ID NO:473:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:473:

UCACGGACUG AUGAGGCCGA AAGGCCGAAA ACAUGU        36

( 2 ) INFORMATION FOR SEQ ID NO:474:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

UUCACGGCUG AUGAGGCCGA AAGGCCGAAA AACAUG        36

( 2 ) INFORMATION FOR SEQ ID NO:475:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

UUUCACGCUG AUGAGGCCGA AAGGCCGAAA AAACAU      36

( 2 ) INFORMATION FOR SEQ ID NO:476:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:476:

AACAGCCCUG AUGAGGCCGA AAGGCCGAAA UUGUUC      36

( 2 ) INFORMATION FOR SEQ ID NO:477:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:477:

ACAUGGGCUG AUGAGGCCGA AAGGCCGAAA CAGCCU      36

( 2 ) INFORMATION FOR SEQ ID NO:478:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:478:

UACAUGGCUG AUGAGGCCGA AAGGCCGAAA ACAGCC      36

( 2 ) INFORMATION FOR SEQ ID NO:479:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:479:

AGGGGGCCUG AUGAGGCCGA AAGGCCGAAA CAUGGG      36

( 2 ) INFORMATION FOR SEQ ID NO:480:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:480:

AGGCACACUG AUGAGGCCGA AAGGCCGAAA GGCCAG      36

( 2 ) INFORMATION FOR SEQ ID NO:481:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:481:

UCAAAAGCUG AUGAGGCCGA AAGGCCGAAA GGCACA 36

( 2 ) INFORMATION FOR SEQ ID NO:482:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:482:

AUCAAAACUG AUGAGGCCGA AAGGCCGAAA AGGCAC 36

( 2 ) INFORMATION FOR SEQ ID NO:483:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:483:

UAAUCAACUG AUGAGGCCGA AAGGCCGAAA GAAGGC 36

( 2 ) INFORMATION FOR SEQ ID NO:484:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:484:

AUAAUCACUG AUGAGGCCGA AAGGCCGAAA AGAAGG 36

( 2 ) INFORMATION FOR SEQ ID NO:485:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:485:

CAUAAUCCUG AUGAGGCCGA AAGGCCGAAA AAGAAG 36

( 2 ) INFORMATION FOR SEQ ID NO:486:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:486:

AAAACAUCUG AUGAGGCCGA AAGGCCGAAA UCAAAA 36

( 2 ) INFORMATION FOR SEQ ID NO:487:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:487:

AAAAACACUG AUGAGGCCGA AAGGCCGAAA AUCAAA 36

(2) INFORMATION FOR SEQ ID NO:488:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:488:

UUUAAAACUG AUGAGGCCGA AAGGCCGAAA CAUAAU 36

(2) INFORMATION FOR SEQ ID NO:489:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:489:

UUUUAAACUG AUGAGGCCGA AAGGCCGAAA ACAUAA 36

(2) INFORMATION FOR SEQ ID NO:490:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:490:

AUUUUAACUG AUGAGGCCGA AAGGCCGAAA AACAUA 36

(2) INFORMATION FOR SEQ ID NO:491:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:491:

UAUUUUACUG AUGAGGCCGA AAGGCCGAAA AAACAU 36

(2) INFORMATION FOR SEQ ID NO:492:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:492:

AUAUUUUCUG AUGAGGCCGA AAGGCCGAAA AAAACA 36

(2) INFORMATION FOR SEQ ID NO:493:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:493:

AAUAUUUCUG AUGAGGCCGA AAGGCCGAAA AAAAAC    36

( 2 ) INFORMATION FOR SEQ ID NO:494:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:494:

CAGAUAACUG AUGAGGCCGA AAGGCCGAAA UUUUAA    36

( 2 ) INFORMATION FOR SEQ ID NO:495:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:495:

AUCAGAUCUG AUGAGGCCGA AAGGCCGAAA UAUUUU    36

( 2 ) INFORMATION FOR SEQ ID NO:496:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:496:

AAUCAGACUG AUGAGGCCGA AAGGCCGAAA AUAUUU    36

( 2 ) INFORMATION FOR SEQ ID NO:497:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:497:

UUAAUCACUG AUGAGGCCGA AAGGCCGAAA UAAUAU    36

( 2 ) INFORMATION FOR SEQ ID NO:498:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:498:

ACAACUUCUG AUGAGGCCGA AAGGCCGAAA UCAGAU    36

( 2 ) INFORMATION FOR SEQ ID NO:499:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:499:

GACAACUCUG AUGAGGCCGA AAGGCCGAAA AUCAGA　　　　　　　　　　　　36

( 2 ) INFORMATION FOR SEQ ID NO:500:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:500:

UUUAGACCUG AUGAGGCCGA AAGGCCGAAA CUUAAU　　　　　　　　　　　　36

( 2 ) INFORMATION FOR SEQ ID NO:501:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:501:

UUGUUUACUG AUGAGGCCGA AAGGCCGAAA CAACUU　　　　　　　　　　　　36

( 2 ) INFORMATION FOR SEQ ID NO:502:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:502:

CAUUGUUCUG AUGAGGCCGA AAGGCCGAAA GACAAC　　　　　　　　　　　　36

( 2 ) INFORMATION FOR SEQ ID NO:503:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:503:

GUCACCACUG AUGAGGCCGA AAGGCCGAAA UCAGCA　　　　　　　　　　　　36

( 2 ) INFORMATION FOR SEQ ID NO:504:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:504:

GGUCACCCUG AUGAGGCCGA AAGGCCGAAA AUCAGC　　　　　　　　　　　　36

( 2 ) INFORMATION FOR SEQ ID NO:505:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:505:

AAUGAGUCUG AUGAGGCCGA AAGGCCGAAA CAGUUG 36

(2) INFORMATION FOR SEQ ID NO:506:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:506:

CAGCAAUCUG AUGAGGCCGA AAGGCCGAAA GUGACA 36

(2) INFORMATION FOR SEQ ID NO:507:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:507:

CCUCAGCCUG AUGAGGCCGA AAGGCCGAAA UGAGUG 36

(2) INFORMATION FOR SEQ ID NO:508:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:508:

GGGAGCACUG AUGAGGCCGA AAGGCCGAAA GGCCUC 36

(2) INFORMATION FOR SEQ ID NO:509:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:509:

CCCUGGGCUG AUGAGGCCGA AAGGCCGAAA GCAGAG 36

(2) INFORMATION FOR SEQ ID NO:510:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:510:

CAGACACCUG AUGAGGCCGA AAGGCCGAAA CUCCCU 36

(2) INFORMATION FOR SEQ ID NO:511:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:511:

GAUUACACUG AUGAGGCCGA AAGGCCGAAA CACAAC 36

(2) INFORMATION FOR SEQ ID NO:512:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:512:

GGCCGAUCUG AUGAGGCCGA AAGGCCGAAA CAGACA 36

(2) INFORMATION FOR SEQ ID NO:513:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:513:

GUAGGCCUG AUGAGGCCGA AAGGCCGAAA UUACAG 36

(2) INFORMATION FOR SEQ ID NO:514:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:514:

UGAAUAGCUG AUGAGGCCGA AAGGCCGAAA GGCCGA 36

(2) INFORMATION FOR SEQ ID NO:515:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:515:

CACUGAACUG AUGAGGCCGA AAGGCCGAAA GUAGGC 36

(2) INFORMATION FOR SEQ ID NO:516:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:516:

GCCACUGCUG AUGAGGCCGA AAGGCCGAAA UAGUAG 36

(2) INFORMATION FOR SEQ ID NO:517:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:517:

CGCCACUCUG AUGAGGCCGA AAGGCCGAAA AUAGUA 36

(2) INFORMATION FOR SEQ ID NO:518:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:518:

CAACCUUCUG AUGAGGCCGA AAGGCCGAAA UUUCUC 36

( 2 ) INFORMATION FOR SEQ ID NO:519:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:519:

CCUAAGCCUG AUGAGGCCGA AAGGCCGAAA CCUUUA 36

( 2 ) INFORMATION FOR SEQ ID NO:520:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:520:

CUUUCCUCUG AUGAGGCCGA AAGGCCGAAA GCAACC 36

( 2 ) INFORMATION FOR SEQ ID NO:521:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:521:

UCUUUCCCUG AUGAGGCCGA AAGGCCGAAA AGCAAC 36

( 2 ) INFORMATION FOR SEQ ID NO:522:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:522:

UGGAAAUAGC UCCCA 15

( 2 ) INFORMATION FOR SEQ ID NO:523:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:523:

GGCAGGUUCU GUCCC 15

( 2 ) INFORMATION FOR SEQ ID NO:524:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:524:

GGCAGGUUCU GUCCC 15

(2) INFORMATION FOR SEQ ID NO:525:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:525:

GCAGGUUCUG UCCCU 15

(2) INFORMATION FOR SEQ ID NO:526:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:526:

GCAGGUUCUG UCCCU 15

(2) INFORMATION FOR SEQ ID NO:527:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:527:

GUUCUGUCCC UUUCA 15

(2) INFORMATION FOR SEQ ID NO:528:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:528:

UGUCCCUUUC ACUCA 15

(2) INFORMATION FOR SEQ ID NO:529:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:529:

GUCCCUUUCA CUCAC 15

(2) INFORMATION FOR SEQ ID NO:530:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:530:

GUCCCUUUCA CUCAC 15

( 2 ) INFORMATION FOR SEQ ID NO:531:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:531:

UCCCUUUCAC UCACU 15

( 2 ) INFORMATION FOR SEQ ID NO:532:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:532:

UUUCACUCAC UGGCC 15

( 2 ) INFORMATION FOR SEQ ID NO:533:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:533:

GCCACAUCUC CCUCC 15

( 2 ) INFORMATION FOR SEQ ID NO:534:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:534:

CACAUCUCCC UCCAG 15

( 2 ) INFORMATION FOR SEQ ID NO:535:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:535:

GCAUGAUCCG CGACG 15

( 2 ) INFORMATION FOR SEQ ID NO:536:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:536:

AGGCACUCCC CCAAA 15

( 2 ) INFORMATION FOR SEQ ID NO:537:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:537:

GGGGCUUCCA GAACU 15

( 2 ) INFORMATION FOR SEQ ID NO:538:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:538:

GGGGCUUCCA GAACU 15

( 2 ) INFORMATION FOR SEQ ID NO:539:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:539:

CAGAACUCCA GGCGG 15

( 2 ) INFORMATION FOR SEQ ID NO:540:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:540:

CAGAACUCCA GGCGG 15

( 2 ) INFORMATION FOR SEQ ID NO:541:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:541:

GGUGCCUAUG UCUCA 15

( 2 ) INFORMATION FOR SEQ ID NO:542:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:542:

```
GGUGCCUAUG UCUCA                                                                              15
```

( 2 ) INFORMATION FOR SEQ ID NO:543:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:543:

```
UCAGCCUCUU CUCAU                                                                              15
```

( 2 ) INFORMATION FOR SEQ ID NO:544:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:544:

```
UCAGCCUCUU CUCAU                                                                              15
```

( 2 ) INFORMATION FOR SEQ ID NO:545:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:545:

```
AGCCUCUUCU CAUUC                                                                              15
```

( 2 ) INFORMATION FOR SEQ ID NO:546:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:546:

```
AGCCUCUUCU CAUUC                                                                              15
```

( 2 ) INFORMATION FOR SEQ ID NO:547:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:547:

```
GCCUCUUCUC AUUCC                                                                              15
```

( 2 ) INFORMATION FOR SEQ ID NO:548:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:548:

```
GCCUCUUCUC AUUCC                                                                              15
```

( 2 ) INFORMATION FOR SEQ ID NO:549:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:549:

CUCUUCUCAU UCCUG 15

( 2 ) INFORMATION FOR SEQ ID NO:550:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:550:

UUCUCAUUCC UGCUU 15

( 2 ) INFORMATION FOR SEQ ID NO:551:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:551:

UCUCAUUCCU GCUUG 15

( 2 ) INFORMATION FOR SEQ ID NO:552:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:552:

UCCUGCUUGU GGCAG 15

( 2 ) INFORMATION FOR SEQ ID NO:553:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:553:

CCACGCUCUU CUGUC 15

( 2 ) INFORMATION FOR SEQ ID NO:554:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:554:

ACGCUCUUCU GUCUA 15

( 2 ) INFORMATION FOR SEQ ID NO:555:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:555:

CGCUCUUCUG UCUAC     15

( 2 ) INFORMATION FOR SEQ ID NO:556:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:556:

CUUCUGUCUA CUGAA     15

( 2 ) INFORMATION FOR SEQ ID NO:557:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:557:

UCUGUCUACU GAACU     15

( 2 ) INFORMATION FOR SEQ ID NO:558:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:558:

CUGAACUUCG GGGUG     15

( 2 ) INFORMATION FOR SEQ ID NO:559:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:559:

UGAACUUCGG GGUGA     15

( 2 ) INFORMATION FOR SEQ ID NO:560:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:560:

UGAACUUCGG GGUGA     15

( 2 ) INFORMATION FOR SEQ ID NO:561:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:561:

GGGUGAUCGG UCCCC                                                                 15

( 2 ) INFORMATION FOR SEQ ID NO:562:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:562:

GGGUGAUCGG UCCCC                                                                 15

( 2 ) INFORMATION FOR SEQ ID NO:563:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:563:

GAGAAGUUCC CAAAU                                                                 15

( 2 ) INFORMATION FOR SEQ ID NO:564:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:564:

CCUCCCUCUC AUCAG                                                                 15

( 2 ) INFORMATION FOR SEQ ID NO:565:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:565:

UCCCUCUCAU CAGUU                                                                 15

( 2 ) INFORMATION FOR SEQ ID NO:566:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:566:

UCCCUCUCAU CAGUU                                                                 15

( 2 ) INFORMATION FOR SEQ ID NO:567:

( i ) SEQUENCE CHARACTERISTICS:
      ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:567:

CUCUCAUCAG UUCUA 15

(2) INFORMATION FOR SEQ ID NO:568:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:568:

CAGUUCUAUG GCCCA 15

(2) INFORMATION FOR SEQ ID NO:569:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:569:

AGACCCUCAC ACUCA 15

(2) INFORMATION FOR SEQ ID NO:570:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:570:

UCACACUCAG AUCAU 15

(2) INFORMATION FOR SEQ ID NO:571:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:571:

CUCAGAUCAU CUUCU 15

(2) INFORMATION FOR SEQ ID NO:572:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:572:

AGAUCAUCUU CUCAA 15

(2) INFORMATION FOR SEQ ID NO:573:

(i) SEQUENCE CHARACTERISTICS:
(A) LENGTH: 15 base pairs
(B) TYPE: nucleic acid
(C) STRANDEDNESS: single -continued ( D ) TOPOLOGY: linear ( x i ) SEQUENCE DESCRIPTION: SEQ ID NO:573:

AUCAUCUUCU CAAAA                                                                15

( 2 ) INFORMATION FOR SEQ ID NO:574:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:574:

AUCAUCUUCU CAAAA                                                                15

( 2 ) INFORMATION FOR SEQ ID NO:575:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:575:

UCAUCUUCUC AAAAU                                                                15

( 2 ) INFORMATION FOR SEQ ID NO:576:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:576:

AUCUUCUCAA AAUUC                                                                15

( 2 ) INFORMATION FOR SEQ ID NO:577:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:577:

AUCUUCUCAA AAUUC                                                                15

( 2 ) INFORMATION FOR SEQ ID NO:578:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:578:

AUCUUCUCAA AAUUC                                                                15

( 2 ) INFORMATION FOR SEQ ID NO:579:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear (x i) SEQUENCE DESCRIPTION: SEQ ID NO:579:

AGCCUGUAGC CCACG 15

(2) INFORMATION FOR SEQ ID NO:580:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:580:

ACGUCGUAGC AAACC 15

(2) INFORMATION FOR SEQ ID NO:581:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:581:

ACGCCCUCCU GGCCA 15

(2) INFORMATION FOR SEQ ID NO:582:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:582:

GGGUUGUACC UUGUC 15

(2) INFORMATION FOR SEQ ID NO:583:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:583:

GGGUUGUACC UUGUC 15

(2) INFORMATION FOR SEQ ID NO:584:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:584:

UGUACCUUGU CUACU 15

(2) INFORMATION FOR SEQ ID NO:585:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:585:

ACCUUGUCUA CUCCC 15

(2) INFORMATION FOR SEQ ID NO:586:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:586:

CUUGUCUACU CCCAG 15

(2) INFORMATION FOR SEQ ID NO:587:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:587:

GUCUACUCCC AGGUU 15

(2) INFORMATION FOR SEQ ID NO:588:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:588:

GUCUACUCCC AGGUU 15

(2) INFORMATION FOR SEQ ID NO:589:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:589:

GUCUACUCCC AGGUU 15

(2) INFORMATION FOR SEQ ID NO:590:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:590:

CCCAGGUUCU CUUCA 15

(2) INFORMATION FOR SEQ ID NO:591:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:591:

CCAGGUUCUC UUCAA 15

( 2 ) INFORMATION FOR SEQ ID NO:592:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:592:

CCAGGUUCUC UUCAA                 15

( 2 ) INFORMATION FOR SEQ ID NO:593:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:593:

AGGUUCUCUU CAAGG                 15

( 2 ) INFORMATION FOR SEQ ID NO:594:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:594:

AGGUUCUCUU CAAGG                 15

( 2 ) INFORMATION FOR SEQ ID NO:595:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:595:

GUUCUCUUCA AGGGA                 15

( 2 ) INFORMATION FOR SEQ ID NO:596:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:596:

UUCUCUUCAA GGGAC                 15

( 2 ) INFORMATION FOR SEQ ID NO:597:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:597:

CCCGACUACG UGCUC                 15

( 2 ) INFORMATION FOR SEQ ID NO:598:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:598:

ACGUGCUCCU CACCC　　　　　　　　　　　　　　　　　　　　　　　15

( 2 ) INFORMATION FOR SEQ ID NO:599:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:599:

ACGUGCUCCU CACCC　　　　　　　　　　　　　　　　　　　　　　　15

( 2 ) INFORMATION FOR SEQ ID NO:600:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:600:

UGCUCCUCAC CCACA　　　　　　　　　　　　　　　　　　　　　　　15

( 2 ) INFORMATION FOR SEQ ID NO:601:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:601:

ACACCGUCAG CCGAU　　　　　　　　　　　　　　　　　　　　　　　15

( 2 ) INFORMATION FOR SEQ ID NO:602:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:602:

ACACCGUCAG CCGAU　　　　　　　　　　　　　　　　　　　　　　　15

( 2 ) INFORMATION FOR SEQ ID NO:603:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:603:

AGCCGAUUUG CUAUC　　　　　　　　　　　　　　　　　　　　　　　15

( 2 ) INFORMATION FOR SEQ ID NO:604:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:604:

AUUUGCUAUC UCAUA 15

(2) INFORMATION FOR SEQ ID NO:605:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:605:

UUGCUAUCUC AUACC 15

(2) INFORMATION FOR SEQ ID NO:606:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:606:

GCUAUCUCAU ACCAG 15

(2) INFORMATION FOR SEQ ID NO:607:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:607:

AGAAAGUCAA CCUCC 15

(2) INFORMATION FOR SEQ ID NO:608:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:608:

UCAACCUCCU CUCUG 15

(2) INFORMATION FOR SEQ ID NO:609:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:609:

UCAACCUCCU CUCUG 15

(2) INFORMATION FOR SEQ ID NO:610:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:610:

ACCUCCUCUC UGCCG 15

( 2 ) INFORMATION FOR SEQ ID NO:611:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:611:

CUCCUCUCUG CCGUC 15

( 2 ) INFORMATION FOR SEQ ID NO:612:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:612:

CUGCCGUCAA GAGCC 15

( 2 ) INFORMATION FOR SEQ ID NO:613:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:613:

CUGCCGUCAA GAGCC 15

( 2 ) INFORMATION FOR SEQ ID NO:614:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:614:

CUGCCGUCAA GAGCC 15

( 2 ) INFORMATION FOR SEQ ID NO:615:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:615:

CCCUGGUAUG AGCCC 15

( 2 ) INFORMATION FOR SEQ ID NO:616:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:616:

CCCUGGUAUG AGCCC                                                                15

( 2 ) INFORMATION FOR SEQ ID NO:617:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:617:

AGCCCAUAUA CCUGG                                                                15

( 2 ) INFORMATION FOR SEQ ID NO:618:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:618:

CCCAUAUACC UGGGA                                                                15

( 2 ) INFORMATION FOR SEQ ID NO:619:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:619:

GAGGAGUCUU CCAGC                                                                15

( 2 ) INFORMATION FOR SEQ ID NO:620:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:620:

GAGGAGUCUU CCAGC                                                                15

( 2 ) INFORMATION FOR SEQ ID NO:621:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:621:

GGAGUCUUCC AGCUG                                                                15

( 2 ) INFORMATION FOR SEQ ID NO:622:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:622:

GAGUCUUCCA GCUGG    15

( 2 ) INFORMATION FOR SEQ ID NO:623:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:623:

ACCAACUCAG CGCUG    15

( 2 ) INFORMATION FOR SEQ ID NO:624:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:624:

CUGAGGUCAA UCUGC    15

( 2 ) INFORMATION FOR SEQ ID NO:625:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:625:

GGUCAAUCUG CCCAA    15

( 2 ) INFORMATION FOR SEQ ID NO:626:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:626:

CCCAAGUACU UAGAC    15

( 2 ) INFORMATION FOR SEQ ID NO:627:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:627:

AGUACUUAGA CUUUG    15

( 2 ) INFORMATION FOR SEQ ID NO:628:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:628:

UUAGACUUUG CGGAG    15

( 2 ) INFORMATION FOR SEQ ID NO:629:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:629:

UAGACUUUGC GGAGU 15

( 2 ) INFORMATION FOR SEQ ID NO:630:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:630:

GCGGAGUCCG GGCAG 15

( 2 ) INFORMATION FOR SEQ ID NO:631:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:631:

GGCAGGUCUA CUUUG 15

( 2 ) INFORMATION FOR SEQ ID NO:632:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:632:

CAGGUCUACU UUGGA 15

( 2 ) INFORMATION FOR SEQ ID NO:633:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:633:

CAGGUCUACU UUGGA 15

( 2 ) INFORMATION FOR SEQ ID NO:634:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:634:

CAGGUCUACU UUGGA 15

( 2 ) INFORMATION FOR SEQ ID NO:635:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:635:

GUCUACUUUG GAGUC                                      15

( 2 ) INFORMATION FOR SEQ ID NO:636:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:636:

UCUACUUUGG AGUCA                                      15

( 2 ) INFORMATION FOR SEQ ID NO:637:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:637:

UUGGAGUCAU UGCUC                                      15

( 2 ) INFORMATION FOR SEQ ID NO:638:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:638:

GAGUCAUUGC UCUGU                                      15

( 2 ) INFORMATION FOR SEQ ID NO:639:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:639:

AUCCAUUCUC UACCC                                      15

( 2 ) INFORMATION FOR SEQ ID NO:640:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:640:

AUUCUCUACC CAGCC                                      15

( 2 ) INFORMATION FOR SEQ ID NO:641:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:641:

CCCCACUCUG ACCCC 15

( 2 ) INFORMATION FOR SEQ ID NO:642:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:642:

CCCCACUCUG ACCCC 15

( 2 ) INFORMATION FOR SEQ ID NO:643:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:643:

CCCCACUCUG ACCCC 15

( 2 ) INFORMATION FOR SEQ ID NO:644:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:644:

GACCCCUUUA CUCUG 15

( 2 ) INFORMATION FOR SEQ ID NO:645:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:645:

ACCCCUUUAC UCUGA 15

( 2 ) INFORMATION FOR SEQ ID NO:646:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:646:

CUUUACUCUG ACCCC 15

( 2 ) INFORMATION FOR SEQ ID NO:647:

( i ) SEQUENCE CHARACTERISTICS:
    ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO:647:

GACCCCUUUA UUGUC                                                                                     15

(2) INFORMATION FOR SEQ ID NO:648:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:648:

GACCCCUUUA UUGUC                                                                                     15

(2) INFORMATION FOR SEQ ID NO:649:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:649:

CCUUUAUUGU CUACU                                                                                     15

(2) INFORMATION FOR SEQ ID NO:650:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:650:

GUCUACUCCU CAGAG                                                                                     15

(2) INFORMATION FOR SEQ ID NO:651:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:651:

UACUCCUCAG AGCCC                                                                                     15

(2) INFORMATION FOR SEQ ID NO:652:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:652:

UCUAACUUAG AAAGG                                                                                     15

(2) INFORMATION FOR SEQ ID NO:653:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO:653:

UCUAACUUAG AAAGG    15

(2) INFORMATION FOR SEQ ID NO:654:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:654:

CUAACUUAGA AAGGG    15

(2) INFORMATION FOR SEQ ID NO:655:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:655:

AGGGGAUUAU GGCUC    15

(2) INFORMATION FOR SEQ ID NO:656:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:656:

AGGGGAUUAU GGCUC    15

(2) INFORMATION FOR SEQ ID NO:657:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:657:

GGGGAUUAUG GCUCA    15

(2) INFORMATION FOR SEQ ID NO:658:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:658:

UCAGAGUCCA ACUCU    15

(2) INFORMATION FOR SEQ ID NO:659:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:659:

CUGUGCUCAG AGCUU                                                                                        15

(2) INFORMATION FOR SEQ ID NO:660:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:660:

CAGAGCUUUC AACAA                                                                                        15

(2) INFORMATION FOR SEQ ID NO:661:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:661:

AGAGCUUUCA ACAAC                                                                                        15

(2) INFORMATION FOR SEQ ID NO:662:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:662:

GAGCUUUCAA CAACU                                                                                        15

(2) INFORMATION FOR SEQ ID NO:663:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:663:

UGGGCCUCUC AUGCA                                                                                        15

(2) INFORMATION FOR SEQ ID NO:664:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:664:

AAGGACUCAA AUGGG                                                                                        15

(2) INFORMATION FOR SEQ ID NO:665:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:665:

AUGGGCUUUC CGAAU                                                                15

( 2 ) INFORMATION FOR SEQ ID NO:666:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:666:

UGGGCUUUCC GAAUU                                                                15

( 2 ) INFORMATION FOR SEQ ID NO:667:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:667:

GGGCUUUCCG AAUUC                                                                15

( 2 ) INFORMATION FOR SEQ ID NO:668:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:668:

CCGAAUUCAC UGGAG                                                                15

( 2 ) INFORMATION FOR SEQ ID NO:669:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:669:

CGAAUGUCCA UUCCU                                                                15

( 2 ) INFORMATION FOR SEQ ID NO:670:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:670:

GAGUGGUCAG GUUGC                                                                15

( 2 ) INFORMATION FOR SEQ ID NO:671:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:671:

UCUGUCUCAG AAUGA                                                                15

( 2 ) INFORMATION FOR SEQ ID NO:672:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:672:

AAGAUCUCAG GCCUU  15

( 2 ) INFORMATION FOR SEQ ID NO:673:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:673:

CAGGCCUUCC UACCU  15

( 2 ) INFORMATION FOR SEQ ID NO:674:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:674:

AGGCCUUCCU ACCUU  15

( 2 ) INFORMATION FOR SEQ ID NO:675:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:675:

CCUUCCUACC UUCAG  15

( 2 ) INFORMATION FOR SEQ ID NO:676:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:676:

CCUACCUUCA GACCU  15

( 2 ) INFORMATION FOR SEQ ID NO:677:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:677:

CCUACCUUCA GACCU  15

( 2 ) INFORMATION FOR SEQ ID NO:678:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:678:

CCUACCUUCA GACCU  15

( 2 ) INFORMATION FOR SEQ ID NO:679:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:679:

CCUACCUUCA GACCU  15

( 2 ) INFORMATION FOR SEQ ID NO:680:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:680:

CUACCUUCAG ACCUU  15

( 2 ) INFORMATION FOR SEQ ID NO:681:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:681:

CUACCUUCAG ACCUU  15

( 2 ) INFORMATION FOR SEQ ID NO:682:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:682:

CAGACCUUUC CAGAC  15

( 2 ) INFORMATION FOR SEQ ID NO:683:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:683:

CAGACCUUUC CAGAC  15

( 2 ) INFORMATION FOR SEQ ID NO:684:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:684:

AGACCUUUCC AGACU 15

(2) INFORMATION FOR SEQ ID NO:685:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:685:

AGACCUUUCC AGACU 15

(2) INFORMATION FOR SEQ ID NO:686:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:686:

GACCUUUCCA GACUC 15

(2) INFORMATION FOR SEQ ID NO:687:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:687:

GACUCUUCCC UGAGG 15

(2) INFORMATION FOR SEQ ID NO:688:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:688:

CAGCCUUCCU CACAG 15

(2) INFORMATION FOR SEQ ID NO:689:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:689:

CCCCCUCUA UUUAU 15

(2) INFORMATION FOR SEQ ID NO:690:

(i) SEQUENCE CHARACTERISTICS:
(A) LENGTH: 15 base pairs
(B) TYPE: nucleic acid (C) STRANDEDNESS: single
(D) TOPOLOGY: linear (x i) SEQUENCE DESCRIPTION: SEQ ID NO:690:

CCCCCCUCUA UUUAU 15

(2) INFORMATION FOR SEQ ID NO:691:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:691:

CCCCUCUAUU UAUAU 15

(2) INFORMATION FOR SEQ ID NO:692:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:692:

CCUCUAUUUA UAUUU 15

(2) INFORMATION FOR SEQ ID NO:693:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:693:

CCUCUAUUUA UAUUU 15

(2) INFORMATION FOR SEQ ID NO:694:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:694:

CUCUAUUUAU AUUUG 15

(2) INFORMATION FOR SEQ ID NO:695:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:695:

UCUAUUUAUA UUUGC 15

(2) INFORMATION FOR SEQ ID NO:696:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:696:

UUUAUAUUUG CACUU 15

( 2 ) INFORMATION FOR SEQ ID NO:697:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:697:

UUUAUAUUUG CACUU 15

( 2 ) INFORMATION FOR SEQ ID NO:698:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:698:

UUAUAUUUGC ACUUA 15

( 2 ) INFORMATION FOR SEQ ID NO:699:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:699:

UUGCACUUAU UAUUU 15

( 2 ) INFORMATION FOR SEQ ID NO:700:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:700:

CACUUAUUAU UUAUU 15

( 2 ) INFORMATION FOR SEQ ID NO:701:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:701:

ACUUAUUAUU UAUUA 15

( 2 ) INFORMATION FOR SEQ ID NO:702:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:702:

UUAUUAUUUA UUAUU                                                                                        15

( 2 ) INFORMATION FOR SEQ ID NO:703:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:703:

UAUUAUUUAU UAUUU                                                                                         15

( 2 ) INFORMATION FOR SEQ ID NO:704:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:704:

UAUUAUUUAU UAUUU                                                                                         15

( 2 ) INFORMATION FOR SEQ ID NO:705:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:705:

AUUAUUUAUU AUUUA                                                                                         15

( 2 ) INFORMATION FOR SEQ ID NO:706:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:706:

UAUUUAUUAU UUAUU                                                                                         15

( 2 ) INFORMATION FOR SEQ ID NO:707:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:707:

UAUUUAUUAU UUAUU                                                                                         15

( 2 ) INFORMATION FOR SEQ ID NO:708:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:708:

UAUUUAUUAU UUAUU                                                                                         15

( 2 ) INFORMATION FOR SEQ ID NO:709:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:709:

AUUUAUUAUU UAUUU  15

( 2 ) INFORMATION FOR SEQ ID NO:710:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:710:

AUUUAUUAUU UAUUU  15

( 2 ) INFORMATION FOR SEQ ID NO:711:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:711:

AUUUAUUAUU UAUUU  15

( 2 ) INFORMATION FOR SEQ ID NO:712:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:712:

UUAUUAUUUA UUUAU  15

( 2 ) INFORMATION FOR SEQ ID NO:713:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:713:

UUAUUAUUUA UUUAU  15

( 2 ) INFORMATION FOR SEQ ID NO:714:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:714:

UUAUUAUUUA UUUAU  15

( 2 ) INFORMATION FOR SEQ ID NO:715:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:715:

UAUUAUUUAU UUAUU 15

( 2 ) INFORMATION FOR SEQ ID NO:716:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:716:

UAUUAUUUAU UUAUU 15

( 2 ) INFORMATION FOR SEQ ID NO:717:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:717:

AUUAUUUAUU UAUUA 15

( 2 ) INFORMATION FOR SEQ ID NO:718:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:718:

UAUUUAUUUA UUAUU 15

( 2 ) INFORMATION FOR SEQ ID NO:719:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:719:

AUUUAUUUAU UAUUU 15

( 2 ) INFORMATION FOR SEQ ID NO:720:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:720:

UUUAUUUAUU AUUUA 15

( 2 ) INFORMATION FOR SEQ ID NO:721:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:721:

AUUAUUUAUU UAUUU 15

( 2 ) INFORMATION FOR SEQ ID NO:722:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:722:

UAUUUAUUUA UUUGC 15

( 2 ) INFORMATION FOR SEQ ID NO:723:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:723:

AUUUAUUUAU UUGCU 15

( 2 ) INFORMATION FOR SEQ ID NO:724:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:724:

UUUAUUUAUU UGCUU 15

( 2 ) INFORMATION FOR SEQ ID NO:725:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:725:

UAUUUAUUUG CUUAU 15

( 2 ) INFORMATION FOR SEQ ID NO:726:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:726:

AUUUAUUUGC UUAUG 15

( 2 ) INFORMATION FOR SEQ ID NO:727:

( i ) SEQUENCE CHARACTERISTICS:
        ( A ) LENGTH: 15 base pairs ( B ) TYPE: nucleic acid
            ( C ) STRANDEDNESS: single
            ( D ) TOPOLOGY: linear ( x i ) SEQUENCE DESCRIPTION: SEQ ID NO:727:

AUUUGCUUAU GAAUG                                                                                             15

( 2 ) INFORMATION FOR SEQ ID NO:728:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:728:

UUUGCUUAUG AAUGU                                                                                             15

( 2 ) INFORMATION FOR SEQ ID NO:729:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:729:

UGAAUGUAUU UAUUU                                                                                             15

( 2 ) INFORMATION FOR SEQ ID NO:730:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:730:

AAUGUAUUUA UUUGG                                                                                             15

( 2 ) INFORMATION FOR SEQ ID NO:731:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:731:

AUGUAUUUAU UUGGA                                                                                             15

( 2 ) INFORMATION FOR SEQ ID NO:732:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:732:

UGUAUUUAUU UGGAA                                                                                             15

( 2 ) INFORMATION FOR SEQ ID NO:733:

( i ) SEQUENCE CHARACTERISTICS:
            ( A ) LENGTH: 15 base pairs
            ( B ) TYPE: nucleic acid
            ( C ) STRANDEDNESS: single ( D ) TOPOLOGY: linear ( x i ) SEQUENCE DESCRIPTION: SEQ ID NO:733:

UAUUUAUUUG GAAGG          15

( 2 ) INFORMATION FOR SEQ ID NO:734:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:734:

UAUUUAUUUG GAAGG          15

( 2 ) INFORMATION FOR SEQ ID NO:735:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:735:

AUUUAUUUGG AAGGC          15

( 2 ) INFORMATION FOR SEQ ID NO:736:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:736:

GGGGUGUCCU GGAGG          15

( 2 ) INFORMATION FOR SEQ ID NO:737:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:737:

GCUGUCUUCA GACAG          15

( 2 ) INFORMATION FOR SEQ ID NO:738:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:738:

GCUGUCUUCA GACAG          15

( 2 ) INFORMATION FOR SEQ ID NO:739:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (x i) SEQUENCE DESCRIPTION: SEQ ID NO:739:

GACAUGUUUU CUGUG 15

(2) INFORMATION FOR SEQ ID NO:740:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:740:

ACAUGUUUUC UGUGA 15

(2) INFORMATION FOR SEQ ID NO:741:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:741:

CAUGUUUUCU GUGAA 15

(2) INFORMATION FOR SEQ ID NO:742:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:742:

AUGUUUCUG UGAAA 15

(2) INFORMATION FOR SEQ ID NO:743:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:743:

AUGUUUCUG UGAAA 15

(2) INFORMATION FOR SEQ ID NO:744:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:744:

GAGCUGUCCC CACCU 15

(2) INFORMATION FOR SEQ ID NO:745:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:745:

CUGGCCUCUC UACCU 15

(2) INFORMATION FOR SEQ ID NO:746:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:746:

GGCCUCUCUA CCUUG 15

(2) INFORMATION FOR SEQ ID NO:747:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:747:

ACCUUGUUGC CUCCU 15

(2) INFORMATION FOR SEQ ID NO:748:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:748:

GCCUCCUCUU UUGCU 15

(2) INFORMATION FOR SEQ ID NO:749:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:749:

CUCCUCUUUU GCUUA 15

(2) INFORMATION FOR SEQ ID NO:750:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:750:

UCCUCUUUUG CUUAU 15

(2) INFORMATION FOR SEQ ID NO:751:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:751:

CCUCUUUUGC UUAUG 15

( 2 ) INFORMATION FOR SEQ ID NO:752:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:752:

UUUUGCUUAU GUUUA 15

( 2 ) INFORMATION FOR SEQ ID NO:753:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:753:

UUUGCUUAUG UUUAA 15

( 2 ) INFORMATION FOR SEQ ID NO:754:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:754:

UUUGCUUAUG UUUAA 15

( 2 ) INFORMATION FOR SEQ ID NO:755:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:755:

UUAUGUUUAA AACAA 15

( 2 ) INFORMATION FOR SEQ ID NO:756:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:756:

AAAUAUUUAU CUAAC 15

( 2 ) INFORMATION FOR SEQ ID NO:757:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:757:

ACCCAAUUGU CUUAA 15

( 2 ) INFORMATION FOR SEQ ID NO:758:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:758:

CAAUUGUCUU AAUAA 15

( 2 ) INFORMATION FOR SEQ ID NO:759:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:759:

AUUGUCUUAA UAACG 15

( 2 ) INFORMATION FOR SEQ ID NO:760:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:760:

CGCUGAUUUG GUGAC 15

( 2 ) INFORMATION FOR SEQ ID NO:761:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:761:

CGCUGAUUUG GUGAC 15

( 2 ) INFORMATION FOR SEQ ID NO:762:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:762:

GCUGAUUUGG UGACC 15

( 2 ) INFORMATION FOR SEQ ID NO:763:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:763:

GCUGAUUUGG UGACC 15

( 2 ) INFORMATION FOR SEQ ID NO:764:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:764:

UGAACCUCUG CUCCC 15

( 2 ) INFORMATION FOR SEQ ID NO:765:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:765:

UGAACCUCUG CUCCC 15

( 2 ) INFORMATION FOR SEQ ID NO:766:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:766:

CUCUGCUCCC CACGG 15

( 2 ) INFORMATION FOR SEQ ID NO:767:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:767:

UGACUGUAAU UGCCC 15

( 2 ) INFORMATION FOR SEQ ID NO:768:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:768:

CUGUAAUUGC CCUAC 15

( 2 ) INFORMATION FOR SEQ ID NO:769:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:769:

GAGAAAUAAA GAUCG 15

( 2 ) INFORMATION FOR SEQ ID NO:770:

( i ) SEQUENCE CHARACTERISTICS:
        ( A ) LENGTH: 15 base pairs
        ( B ) TYPE: nucleic acid ( C ) STRANDEDNESS: single
( D ) TOPOLOGY: linear ( x i ) SEQUENCE DESCRIPTION: SEQ ID NO:770:

UAAAGAUCGC UUAAA   15

( 2 ) INFORMATION FOR SEQ ID NO:771:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:771:

UUAAAAUAAA AAACC   15

( 2 ) INFORMATION FOR SEQ ID NO:772:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:772:

AGGGACUAGC CAGGA   15

( 2 ) INFORMATION FOR SEQ ID NO:773:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:773:

UCCUGGCCUG AUGAGGCCGA AAGGCCGAAA GUCCCU   36

( 2 ) INFORMATION FOR SEQ ID NO:774:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:774:

UGGGAGCCUG AUGAGGCCGA AAGGCCGAAA UUUCCA   36

( 2 ) INFORMATION FOR SEQ ID NO:775:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:775:

GGGACAGCUG AUGAGGCCGA AAGGCCGAAA CCUGCC   36

( 2 ) INFORMATION FOR SEQ ID NO:776:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:776:

GGGACAGCUG AUGAGGCCGA AAGGCCGAAA CCUGCC 36

( 2 ) INFORMATION FOR SEQ ID NO:777:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:777:

AGGGACACUG AUGAGGCCGA AAGGCCGAAA ACCUGC 36

( 2 ) INFORMATION FOR SEQ ID NO:778:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:778:

AGGGACACUG AUGAGGCCGA AAGGCCGAAA ACCUGC 36

( 2 ) INFORMATION FOR SEQ ID NO:779:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:779:

UGAAAGGCUG AUGAGGCCGA AAGGCCGAAA CAGAAC 36

( 2 ) INFORMATION FOR SEQ ID NO:780:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:780:

UGAGUGACUG AUGAGGCCGA AAGGCCGAAA GGGACA 36

( 2 ) INFORMATION FOR SEQ ID NO:781:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:781:

GUGAGUGCUG AUGAGGCCGA AAGGCCGAAA AGGGAC 36

( 2 ) INFORMATION FOR SEQ ID NO:782:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:782:

GUGAGUGCUG AUGAGGCCGA AAGGCCGAAA AGGGAC 36

( 2 ) INFORMATION FOR SEQ ID NO:783:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:783:

AGUGAGUCUG AUGAGGCCGA AAGGCCGAAA AAGGGA 36

( 2 ) INFORMATION FOR SEQ ID NO:784:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:784:

GGCCAGUCUG AUGAGGCCGA AAGGCCGAAA GUGAAA 36

( 2 ) INFORMATION FOR SEQ ID NO:785:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:785:

GGAGGGACUG AUGAGGCCGA AAGGCCGAAA UGUGGC 36

( 2 ) INFORMATION FOR SEQ ID NO:786:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:786:

CUGGAGGCUG AUGAGGCCGA AAGGCCGAAA GAUGUG 36

( 2 ) INFORMATION FOR SEQ ID NO:787:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:787:

CGUCGCGCUG AUGAGGCCGA AAGGCCGAAA UCAUGC 36

( 2 ) INFORMATION FOR SEQ ID NO:788:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:788:

UUUGGGGCUG AUGAGGCCGA AAGGCCGAAA GUGCCU 36

( 2 ) INFORMATION FOR SEQ ID NO:789:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:789:

AGUUCUGCUG AUGAGGCCGA AAGGCCGAAA AGCCCC    36

( 2 ) INFORMATION FOR SEQ ID NO:790:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:790:

AGUUCUGCUG AUGAGGCCGA AAGGCCGAAA AGCCCC    36

( 2 ) INFORMATION FOR SEQ ID NO:791:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:791:

CCGCCUGCUG AUGAGGCCGA AAGGCCGAAA GUUCUG    36

( 2 ) INFORMATION FOR SEQ ID NO:792:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:792:

CCGCCUGCUG AUGAGGCCGA AAGGCCGAAA GUUCUG    36

( 2 ) INFORMATION FOR SEQ ID NO:793:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:793:

UGAGACACUG AUGAGGCCGA AAGGCCGAAA GGCACC    36

( 2 ) INFORMATION FOR SEQ ID NO:794:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:794:

UGAGACACUG AUGAGGCCGA AAGGCCGAAA GGCACC    36

( 2 ) INFORMATION FOR SEQ ID NO:795:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:795:

AUGAGAACUG AUGAGGCCGA AAGGCCGAAA GGCUGA      36

( 2 ) INFORMATION FOR SEQ ID NO:796:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:796:

AUGAGAACUG AUGAGGCCGA AAGGCCGAAA GGCUGA      36

( 2 ) INFORMATION FOR SEQ ID NO:797:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:797:

GAAUGAGCUG AUGAGGCCGA AAGGCCGAAA GAGGCU      36

( 2 ) INFORMATION FOR SEQ ID NO:798:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:798:

GAAUGAGCUG AUGAGGCCGA AAGGCCGAAA GAGGCU      36

( 2 ) INFORMATION FOR SEQ ID NO:799:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:799:

GGAAUGACUG AUGAGGCCGA AAGGCCGAAA AGAGGC      36

( 2 ) INFORMATION FOR SEQ ID NO:800:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:800:

GGAAUGACUG AUGAGGCCGA AAGGCCGAAA AGAGGC      36

( 2 ) INFORMATION FOR SEQ ID NO:801:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:801:

CAGGAAUCUG AUGAGGCCGA AAGGCCGAAA GAAGAG 36

( 2 ) INFORMATION FOR SEQ ID NO:802:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:802:

AAGCAGGCUG AUGAGGCCGA AAGGCCGAAA UGAGAA 36

( 2 ) INFORMATION FOR SEQ ID NO:803:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:803:

CAAGCAGCUG AUGAGGCCGA AAGGCCGAAA AUGAGA 36

( 2 ) INFORMATION FOR SEQ ID NO:804:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:804:

CUGCCACCUG AUGAGGCCGA AAGGCCGAAA GCAGGA 36

( 2 ) INFORMATION FOR SEQ ID NO:805:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:805:

GACAGAACUG AUGAGGCCGA AAGGCCGAAA GCGUGG 36

( 2 ) INFORMATION FOR SEQ ID NO:806:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:806:

UAGACAGCUG AUGAGGCCGA AAGGCCGAAA GAGCGU 36

( 2 ) INFORMATION FOR SEQ ID NO:807:

( i ) SEQUENCE CHARACTERISTICS:
   ( A ) LENGTH: 36 base pairs (B) TYPE: nucleic acid
                (C) STRANDEDNESS: single
                (D) TOPOLOGY: linear (xi) SEQUENCE DESCRIPTION: SEQ ID NO:807:

GUAGACACUG AUGAGGCCGA AAGGCCGAAA AGAGCG 36

(2) INFORMATION FOR SEQ ID NO:808:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:808:

UUCAGUACUG AUGAGGCCGA AAGGCCGAAA CAGAAG 36

(2) INFORMATION FOR SEQ ID NO:809:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:809:

AGUUCAGCUG AUGAGGCCGA AAGGCCGAAA GACAGA 36

(2) INFORMATION FOR SEQ ID NO:810:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:810:

CACCCCGCUG AUGAGGCCGA AAGGCCGAAA GUUCAG 36

(2) INFORMATION FOR SEQ ID NO:811:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:811:

UCACCCCUG AUGAGGCCGA AAGGCCGAAA AGUUCA 36

(2) INFORMATION FOR SEQ ID NO:812:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:812:

UCACCCCUG AUGAGGCCGA AAGGCCGAAA AGUUCA 36

(2) INFORMATION FOR SEQ ID NO:813:

(i) SEQUENCE CHARACTERISTICS:
                (A) LENGTH: 36 base pairs
                (B) TYPE: nucleic acid
                (C) STRANDEDNESS: single (D) TOPOLOGY: linear (xi) SEQUENCE DESCRIPTION: SEQ ID NO:813:

GGGGACCCUG AUGAGGCCGA AAGGCCGAAA UCACCC 36

(2) INFORMATION FOR SEQ ID NO:814:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:814:

GGGGACCCUG AUGAGGCCGA AAGGCCGAAA UCACCC 36

(2) INFORMATION FOR SEQ ID NO:815:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:815:

AUUUGGGCUG AUGAGGCCGA AAGGCCGAAA CUUCUC 36

(2) INFORMATION FOR SEQ ID NO:816:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:816:

CUGAUGACUG AUGAGGCCGA AAGGCCGAAA GGGAGG 36

(2) INFORMATION FOR SEQ ID NO:817:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:817:

AACUGAUCUG AUGAGGCCGA AAGGCCGAAA GAGGGA 36

(2) INFORMATION FOR SEQ ID NO:818:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:818:

AACUGAUCUG AUGAGGCCGA AAGGCCGAAA GAGGGA 36

(2) INFORMATION FOR SEQ ID NO:819:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:819:

UAGAACUCUG AUGAGGCCGA AAGGCCGAAA UGAGAG 36

( 2 ) INFORMATION FOR SEQ ID NO:820:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:820:

UGGGCCACUG AUGAGGCCGA AAGGCCGAAA GAACUG 36

( 2 ) INFORMATION FOR SEQ ID NO:821:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:821:

UGAGUGUCUG AUGAGGCCGA AAGGCCGAAA GGGUCU 36

( 2 ) INFORMATION FOR SEQ ID NO:822:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:822:

AUGAUCUCUG AUGAGGCCGA AAGGCCGAAA GUGUGA 36

( 2 ) INFORMATION FOR SEQ ID NO:823:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:823:

AGAAGAUCUG AUGAGGCCGA AAGGCCGAAA UCUGAG 36

( 2 ) INFORMATION FOR SEQ ID NO:824:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:824:

UUGAGAACUG AUGAGGCCGA AAGGCCGAAA UGAUCU 36

( 2 ) INFORMATION FOR SEQ ID NO:825:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:825:

UUUUGAGCUG AUGAGGCCGA AAGGCCGAAA GAUGAU 36

( 2 ) INFORMATION FOR SEQ ID NO:826:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:826:

UUUUGAGCUG AUGAGGCCGA AAGGCCGAAA GAUGAU 36

( 2 ) INFORMATION FOR SEQ ID NO:827:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:827:

AUUUUGACUG AUGAGGCCGA AAGGCCGAAA AGAUGA 36

( 2 ) INFORMATION FOR SEQ ID NO:828:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:828:

GAAUUUUCUG AUGAGGCCGA AAGGCCGAAA GAAGAU 36

( 2 ) INFORMATION FOR SEQ ID NO:829:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:829:

GAAUUUUCUG AUGAGGCCGA AAGGCCGAAA GAAGAU 36

( 2 ) INFORMATION FOR SEQ ID NO:830:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:830:

GAAUUUUCUG AUGAGGCCGA AAGGCCGAAA GAAGAU 36

( 2 ) INFORMATION FOR SEQ ID NO:831:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:831:

CGUGGGCCUG AUGAGGCCGA AAGGCCGAAA CAGGCU 36

( 2 ) INFORMATION FOR SEQ ID NO:832:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:832:

GGUUUGCCUG AUGAGGCCGA AAGGCCGAAA CGACGU    36

( 2 ) INFORMATION FOR SEQ ID NO:833:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:833:

UGGCCAGCUG AUGAGGCCGA AAGGCCGAAA GGGCGU    36

( 2 ) INFORMATION FOR SEQ ID NO:834:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:834:

GACAAGGCUG AUGAGGCCGA AAGGCCGAAA CAACCC    36

( 2 ) INFORMATION FOR SEQ ID NO:835:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:835:

GACAAGGCUG AUGAGGCCGA AAGGCCGAAA CAACCC    36

( 2 ) INFORMATION FOR SEQ ID NO:836:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:836:

AGUAGACCUG AUGAGGCCGA AAGGCCGAAA GGUACA    36

( 2 ) INFORMATION FOR SEQ ID NO:837:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:837:

GGGAGUACUG AUGAGGCCGA AAGGCCGAAA CAAGGU    36

( 2 ) INFORMATION FOR SEQ ID NO:838:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:838:

CUGGGAGCUG AUGAGGCCGA AAGGCCGAAA GACAAG 36

( 2 ) INFORMATION FOR SEQ ID NO:839:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:839:

AACCUGGCUG AUGAGGCCGA AAGGCCGAAA GUAGAC 36

( 2 ) INFORMATION FOR SEQ ID NO:840:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:840:

AACCUGGCUG AUGAGGCCGA AAGGCCGAAA GUAGAC 36

( 2 ) INFORMATION FOR SEQ ID NO:841:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:841:

AACCUGGCUG AUGAGGCCGA AAGGCCGAAA GUAGAC 36

( 2 ) INFORMATION FOR SEQ ID NO:842:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:842:

UGAAGAGCUG AUGAGGCCGA AAGGCCGAAA CCUGGG 36

( 2 ) INFORMATION FOR SEQ ID NO:843:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:843:

UUGAAGACUG AUGAGGCCGA AAGGCCGAAA ACCUGG 36

( 2 ) INFORMATION FOR SEQ ID NO:844:

( i ) SEQUENCE CHARACTERISTICS:

(A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:844:

UUGAAGACUG AUGAGGCCGA AAGGCCGAAA ACCUGG        36

(2) INFORMATION FOR SEQ ID NO:845:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:845:

CCUUGAACUG AUGAGGCCGA AAGGCCGAAA GAACCU        36

(2) INFORMATION FOR SEQ ID NO:846:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:846:

CCUUGAACUG AUGAGGCCGA AAGGCCGAAA GAACCU        36

(2) INFORMATION FOR SEQ ID NO:847:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:847:

UCCCUUGCUG AUGAGGCCGA AAGGCCGAAA GAGAAC        36

(2) INFORMATION FOR SEQ ID NO:848:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:848:

GUCCCUUCUG AUGAGGCCGA AAGGCCGAAA AGAGAA        36

(2) INFORMATION FOR SEQ ID NO:849:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:849:

GAGCACGCUG AUGAGGCCGA AAGGCCGAAA GUCGGG        36

(2) INFORMATION FOR SEQ ID NO:850:

(i) SEQUENCE CHARACTERISTICS:
                (A) LENGTH: 36 base pairs
                (B) TYPE: nucleic acid (C) STRANDEDNESS: single
        (D) TOPOLOGY: linear (x i) SEQUENCE DESCRIPTION: SEQ ID NO:850:

GGGUGAGCUG AUGAGGCCGA AAGGCCGAAA GCACGU 36

(2) INFORMATION FOR SEQ ID NO:851:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:851:

GGGUGAGCUG AUGAGGCCGA AAGGCCGAAA GCACGU 36

(2) INFORMATION FOR SEQ ID NO:852:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:852:

UGUGGGUCUG AUGAGGCCGA AAGGCCGAAA GGAGCA 36

(2) INFORMATION FOR SEQ ID NO:853:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:853:

AUCGGCUCUG AUGAGGCCGA AAGGCCGAAA CGGUGU 36

(2) INFORMATION FOR SEQ ID NO:854:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:854:

AUCGGCUCUG AUGAGGCCGA AAGGCCGAAA CGGUGU 36

(2) INFORMATION FOR SEQ ID NO:855:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:855:

GAUAGCACUG AUGAGGCCGA AAGGCCGAAA UCGGCU 36

(2) INFORMATION FOR SEQ ID NO:856:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:856:

UAUGAGACUG AUGAGGCCGA AAGGCCGAAA GCAAAU 36

( 2 ) INFORMATION FOR SEQ ID NO:857:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:857:

GGUAUGACUG AUGAGGCCGA AAGGCCGAAA UAGCAA 36

( 2 ) INFORMATION FOR SEQ ID NO:858:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:858:

CUGGUAUCUG AUGAGGCCGA AAGGCCGAAA GAUAGC 36

( 2 ) INFORMATION FOR SEQ ID NO:859:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:859:

GGAGGUUCUG AUGAGGCCGA AAGGCCGAAA CUUUCU 36

( 2 ) INFORMATION FOR SEQ ID NO:860:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:860:

CAGAGAGCUG AUGAGGCCGA AAGGCCGAAA GGUUGA 36

( 2 ) INFORMATION FOR SEQ ID NO:861:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:861:

CAGAGAGCUG AUGAGGCCGA AAGGCCGAAA GGUUGA 36

( 2 ) INFORMATION FOR SEQ ID NO:862:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:862:

CGGCAGACUG AUGAGGCCGA AAGGCCGAAA GGAGGU 36

( 2 ) INFORMATION FOR SEQ ID NO:863:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:863:

GACGGCACUG AUGAGGCCGA AAGGCCGAAA GAGGAG 36

( 2 ) INFORMATION FOR SEQ ID NO:864:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:864:

GGCUCUUCUG AUGAGGCCGA AAGGCCGAAA CGGCAG 36

( 2 ) INFORMATION FOR SEQ ID NO:865:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:865:

GGCUCUUCUG AUGAGGCCGA AAGGCCGAAA CGGCAG 36

( 2 ) INFORMATION FOR SEQ ID NO:866:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:866:

GGCUCUUCUG AUGAGGCCGA AAGGCCGAAA CGGCAG 36

( 2 ) INFORMATION FOR SEQ ID NO:867:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:867:

GGGCUCACUG AUGAGGCCGA AAGGCCGAAA CCAGGG 36

( 2 ) INFORMATION FOR SEQ ID NO:868:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:868:

GGGCUCACUG AUGAGGCCGA AAGGCCGAAA CCAGGG 36

( 2 ) INFORMATION FOR SEQ ID NO:869:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:869:

CCAGGUACUG AUGAGGCCGA AAGGCCGAAA UGGGCU    36

( 2 ) INFORMATION FOR SEQ ID NO:870:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:870:

UCCCAGGCUG AUGAGGCCGA AAGGCCGAAA UAUGGG    36

( 2 ) INFORMATION FOR SEQ ID NO:871:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:871:

GCUGGAACUG AUGAGGCCGA AAGGCCGAAA CUCCUC    36

( 2 ) INFORMATION FOR SEQ ID NO:872:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:872:

GCUGGAACUG AUGAGGCCGA AAGGCCGAAA CUCCUC    36

( 2 ) INFORMATION FOR SEQ ID NO:873:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:873:

CAGCUGGCUG AUGAGGCCGA AAGGCCGAAA GACUCC    36

( 2 ) INFORMATION FOR SEQ ID NO:874:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:874:

CCAGCUGCUG AUGAGGCCGA AAGGCCGAAA AGACUC    36

(2) INFORMATION FOR SEQ ID NO:875:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:875:

CAGCGCUCUG AUGAGGCCGA AAGGCCGAAA GUUGGU    36

(2) INFORMATION FOR SEQ ID NO:876:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:876:

GCAGAUUCUG AUGAGGCCGA AAGGCCGAAA CCUCAG    36

(2) INFORMATION FOR SEQ ID NO:877:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:877:

UUGGGCACUG AUGAGGCCGA AAGGCCGAAA UUGACC    36

(2) INFORMATION FOR SEQ ID NO:878:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:878:

GUCUAAGCUG AUGAGGCCGA AAGGCCGAAA CUUGGG    36

(2) INFORMATION FOR SEQ ID NO:879:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:879:

CAAAGUCCUG AUGAGGCCGA AAGGCCGAAA AGUACU    36

(2) INFORMATION FOR SEQ ID NO:880:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:880:

CUCCGCACUG AUGAGGCCGA AAGGCCGAAA GUCUAA    36

(2) INFORMATION FOR SEQ ID NO:881:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:881:

ACUCCGCUG AUGAGGCCGA AAGGCCGAAA AGUCUA　　　　　　　　　　36

( 2 ) INFORMATION FOR SEQ ID NO:882:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:882:

CUGCCCGCUG AUGAGGCCGA AAGGCCGAAA CUCCGC　　　　　　　　　　36

( 2 ) INFORMATION FOR SEQ ID NO:883:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:883:

CAAAGUACUG AUGAGGCCGA AAGGCCGAAA CCUGCC　　　　　　　　　　36

( 2 ) INFORMATION FOR SEQ ID NO:884:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:884:

UCCAAAGCUG AUGAGGCCGA AAGGCCGAAA GACCUG　　　　　　　　　　36

( 2 ) INFORMATION FOR SEQ ID NO:885:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:885:

UCCAAAGCUG AUGAGGCCGA AAGGCCGAAA GACCUG　　　　　　　　　　36

( 2 ) INFORMATION FOR SEQ ID NO:886:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:886:

UCCAAAGCUG AUGAGGCCGA AAGGCCGAAA GACCUG　　　　　　　　　　36

( 2 ) INFORMATION FOR SEQ ID NO:887:

( i ) SEQUENCE CHARACTERISTICS:
　　　　( A ) LENGTH: 36 base pairs (B) TYPE: nucleic acid
        (C) STRANDEDNESS: single
        (D) TOPOLOGY: linear (xi) SEQUENCE DESCRIPTION: SEQ ID NO:887:

GACUCCACUG AUGAGGCCGA AAGGCCGAAA GUAGAC 36

(2) INFORMATION FOR SEQ ID NO:888:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:888:

UGACUCCCUG AUGAGGCCGA AAGGCCGAAA AGUAGA 36

(2) INFORMATION FOR SEQ ID NO:889:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:889:

GAGCAAUCUG AUGAGGCCGA AAGGCCGAAA CUCCAA 36

(2) INFORMATION FOR SEQ ID NO:890:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:890:

ACAGAGCCUG AUGAGGCCGA AAGGCCGAAA UGACUC 36

(2) INFORMATION FOR SEQ ID NO:891:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:891:

GGGUAGACUG AUGAGGCCGA AAGGCCGAAA AUGGAU 36

(2) INFORMATION FOR SEQ ID NO:892:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:892:

GGCUGGGCUG AUGAGGCCGA AAGGCCGAAA GAGAAU 36

(2) INFORMATION FOR SEQ ID NO:893:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO:893:

GGGGUCACUG AUGAGGCCGA AAGGCCGAAA GUGGGG                             36

(2) INFORMATION FOR SEQ ID NO:894:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:894:

GGGGUCACUG AUGAGGCCGA AAGGCCGAAA GUGGGG                             36

(2) INFORMATION FOR SEQ ID NO:895:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:895:

GGGGUCACUG AUGAGGCCGA AAGGCCGAAA GUGGGG                             36

(2) INFORMATION FOR SEQ ID NO:896:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:896:

CAGAGUACUG AUGAGGCCGA AAGGCCGAAA GGGGUC                             36

(2) INFORMATION FOR SEQ ID NO:897:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:897:

UCAGAGUCUG AUGAGGCCGA AAGGCCGAAA AGGGGU                             36

(2) INFORMATION FOR SEQ ID NO:898:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:898:

GGGGUCACUG AUGAGGCCGA AAGGCCGAAA GUAAAG                             36

(2) INFORMATION FOR SEQ ID NO:899:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (x i) SEQUENCE DESCRIPTION: SEQ ID NO:899:

GACAAUACUG AUGAGGCCGA AAGGCCGAAA GGGGUC 36

(2) INFORMATION FOR SEQ ID NO:900:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:900:

GACAAUACUG AUGAGGCCGA AAGGCCGAAA GGGGUC 36

(2) INFORMATION FOR SEQ ID NO:901:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:901:

AGUAGACCUG AUGAGGCCGA AAGGCCGAAA UAAAGG 36

(2) INFORMATION FOR SEQ ID NO:902:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:902:

CUCUGAGCUG AUGAGGCCGA AAGGCCGAAA GUAGAC 36

(2) INFORMATION FOR SEQ ID NO:903:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:903:

GGGCUCUCUG AUGAGGCCGA AAGGCCGAAA GGAGUA 36

(2) INFORMATION FOR SEQ ID NO:904:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:904:

CCUUUCUCUG AUGAGGCCGA AAGGCCGAAA GUUAGA 36

(2) INFORMATION FOR SEQ ID NO:905:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:905:

CCUUUCUCUG AUGAGGCCGA AAGGCCGAAA GUUAGA    36

( 2 ) INFORMATION FOR SEQ ID NO:906:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:906:

CCCUUUCCUG AUGAGGCCGA AAGGCCGAAA AGUUAG    36

( 2 ) INFORMATION FOR SEQ ID NO:907:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:907:

GAGCCAUCUG AUGAGGCCGA AAGGCCGAAA UCCCCU    36

( 2 ) INFORMATION FOR SEQ ID NO:908:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:908:

GAGCCAUCUG AUGAGGCCGA AAGGCCGAAA UCCCCU    36

( 2 ) INFORMATION FOR SEQ ID NO:909:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:909:

UGAGCCACUG AUGAGGCCGA AAGGCCGAAA AUCCC    36

( 2 ) INFORMATION FOR SEQ ID NO:910:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:910:

AGAGUUGCUG AUGAGGCCGA AAGGCCGAAA CUCUGA    36

( 2 ) INFORMATION FOR SEQ ID NO:911:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:911:

AAGCUCUCUG AUGAGGCCGA AAGGCCGAAA GCACAG    36

( 2 ) INFORMATION FOR SEQ ID NO:912:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:912:

UUGUUGACUG AUGAGGCCGA AAGGCCGAAA GCUCUG    36

( 2 ) INFORMATION FOR SEQ ID NO:913:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:913:

GUUGUUGCUG AUGAGGCCGA AAGGCCGAAA AGCUCU    36

( 2 ) INFORMATION FOR SEQ ID NO:914:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:914:

AGUUGUUCUG AUGAGGCCGA AAGGCCGAAA AAGCUC    36

( 2 ) INFORMATION FOR SEQ ID NO:915:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:915:

UGCAUGACUG AUGAGGCCGA AAGGCCGAAA GGCCCA    36

( 2 ) INFORMATION FOR SEQ ID NO:916:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:916:

CCCAUUUCUG AUGAGGCCGA AAGGCCGAAA GUCCUU    36

( 2 ) INFORMATION FOR SEQ ID NO:917:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:917:

AUUCGGACUG AUGAGGCCGA AAGGCCGAAA GCCCAU    36

( 2 ) INFORMATION FOR SEQ ID NO:918:

(i) SEQUENCE CHARACTERISTICS:
   (A) LENGTH: 36 base pairs
   (B) TYPE: nucleic acid
   (C) STRANDEDNESS: single
   (D) TOPOLOGY: linear (xi) SEQUENCE DESCRIPTION: SEQ ID NO:918:

AAUUCGGCUG AUGAGGCCGA AAGGCCGAAA AGCCCA     36

(2) INFORMATION FOR SEQ ID NO:919:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:919:

GAAUUCGCUG AUGAGGCCGA AAGGCCGAAA AAGCCC     36

(2) INFORMATION FOR SEQ ID NO:920:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:920:

CUCCAGUCUG AUGAGGCCGA AAGGCCGAAA AUUCGG     36

(2) INFORMATION FOR SEQ ID NO:921:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:921:

AGGAAUGCUG AUGAGGCCGA AAGGCCGAAA CAUUCG     36

(2) INFORMATION FOR SEQ ID NO:922:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:922:

GCAACCUCUG AUGAGGCCGA AAGGCCGAAA CCACUC     36

(2) INFORMATION FOR SEQ ID NO:923:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:923:

UCAUUCUCUG AUGAGGCCGA AAGGCCGAAA GACAGA     36

(2) INFORMATION FOR SEQ ID NO:924:

(i) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:924:

AAGGCCUCUG AUGAGGCCGA AAGGCCGAAA GAUCUU 36

(2) INFORMATION FOR SEQ ID NO:925:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:925:

AGGUAGGCUG AUGAGGCCGA AAGGCCGAAA GGCCUG 36

(2) INFORMATION FOR SEQ ID NO:926:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:926:

AAGGUAGCUG AUGAGGCCGA AAGGCCGAAA AGGCCU 36

(2) INFORMATION FOR SEQ ID NO:927:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:927:

CUGAAGGCUG AUGAGGCCGA AAGGCCGAAA GGAAGG 36

(2) INFORMATION FOR SEQ ID NO:928:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:928:

AGGUCUGCUG AUGAGGCCGA AAGGCCGAAA GGUAGG 36

(2) INFORMATION FOR SEQ ID NO:929:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:929:

AGGUCUGCUG AUGAGGCCGA AAGGCCGAAA GGUAGG 36

(2) INFORMATION FOR SEQ ID NO:930:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:930:

AGGUCUGCUG AUGAGGCCGA AAGGCCGAAA GGUAGG  36

(2) INFORMATION FOR SEQ ID NO:931:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (xi) SEQUENCE DESCRIPTION: SEQ ID NO:931:

AGGUCUGCUG AUGAGGCCGA AAGGCCGAAA GGUAGG  36

(2) INFORMATION FOR SEQ ID NO:932:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (xi) SEQUENCE DESCRIPTION: SEQ ID NO:932:

AAGGUCUCUG AUGAGGCCGA AAGGCCGAAA AGGUAG  36

(2) INFORMATION FOR SEQ ID NO:933:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (xi) SEQUENCE DESCRIPTION: SEQ ID NO:933:

AAGGUCUCUG AUGAGGCCGA AAGGCCGAAA AGGUAG  36

(2) INFORMATION FOR SEQ ID NO:934:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (xi) SEQUENCE DESCRIPTION: SEQ ID NO:934:

GUCUGGACUG AUGAGGCCGA AAGGCCGAAA GGUCUG  36

(2) INFORMATION FOR SEQ ID NO:935:

(i) SEQUENCE CHARACTERISTICS:
 (A) LENGTH: 36 base pairs
 (B) TYPE: nucleic acid
 (C) STRANDEDNESS: single
 (D) TOPOLOGY: linear (xi) SEQUENCE DESCRIPTION: SEQ ID NO:935:

GUCUGGACUG AUGAGGCCGA AAGGCCGAAA GGUCUG  36

(2) INFORMATION FOR SEQ ID NO:936:

(i) SEQUENCE CHARACTERISTICS:
 (A) LENGTH: 36 base pairs
 (B) TYPE: nucleic acid
 (C) STRANDEDNESS: single
 (D) TOPOLOGY: linear ( x i ) SEQUENCE DESCRIPTION: SEQ ID NO:936:

AGUCUGGCUG AUGAGGCCGA AAGGCCGAAA AGGUCU 36

( 2 ) INFORMATION FOR SEQ ID NO:937:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:937:

AGUCUGGCUG AUGAGGCCGA AAGGCCGAAA AGGUCU 36

( 2 ) INFORMATION FOR SEQ ID NO:938:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:938:

GAGUCUGCUG AUGAGGCCGA AAGGCCGAAA AAGGUC 36

( 2 ) INFORMATION FOR SEQ ID NO:939:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:939:

CCUCAGGCUG AUGAGGCCGA AAGGCCGAAA AGAGUC 36

( 2 ) INFORMATION FOR SEQ ID NO:940:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:940:

CUGUGAGCUG AUGAGGCCGA AAGGCCGAAA AGGCUG 36

( 2 ) INFORMATION FOR SEQ ID NO:941:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:941:

AUAAAUACUG AUGAGGCCGA AAGGCCGAAA GGGGGG 36

( 2 ) INFORMATION FOR SEQ ID NO:942:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:942:

AUAAAUACUG AUGAGGCCGA AAGGCCGAAA GGGGGG 36

( 2 ) INFORMATION FOR SEQ ID NO:943:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:943:

AUAUAAACUG AUGAGGCCGA AAGGCCGAAA GAGGGG 36

( 2 ) INFORMATION FOR SEQ ID NO:944:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:944:

AAAUAUACUG AUGAGGCCGA AAGGCCGAAA UAGAGG 36

( 2 ) INFORMATION FOR SEQ ID NO:945:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:945:

AAAUAUACUG AUGAGGCCGA AAGGCCGAAA UAGAGG 36

( 2 ) INFORMATION FOR SEQ ID NO:946:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:946:

CAAAUAUCUG AUGAGGCCGA AAGGCCGAAA AUAGAG 36

( 2 ) INFORMATION FOR SEQ ID NO:947:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:947:

GCAAAUACUG AUGAGGCCGA AAGGCCGAAA AAUAGA 36

( 2 ) INFORMATION FOR SEQ ID NO:948:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:948:

AAGUGCACUG AUGAGGCCGA AAGGCCGAAA UAUAAA 36

( 2 ) INFORMATION FOR SEQ ID NO:949:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:949:

AAGUGCACUG AUGAGGCCGA AAGGCCGAAA UAUAAA    36

( 2 ) INFORMATION FOR SEQ ID NO:950:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:950:

UAAGUGCCUG AUGAGGCCGA AAGGCCGAAA AUAUAA    36

( 2 ) INFORMATION FOR SEQ ID NO:951:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:951:

AAAUAAUCUG AUGAGGCCGA AAGGCCGAAA GUGCAA    36

( 2 ) INFORMATION FOR SEQ ID NO:952:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:952:

AAUAAAUCUG AUGAGGCCGA AAGGCCGAAA UAAGUG    36

( 2 ) INFORMATION FOR SEQ ID NO:953:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:953:

UAAUAAACUG AUGAGGCCGA AAGGCCGAAA AUAAGU    36

( 2 ) INFORMATION FOR SEQ ID NO:954:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:954:

AAUAAUACUG AUGAGGCCGA AAGGCCGAAA UAAUAA    36

( 2 ) INFORMATION FOR SEQ ID NO:955:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:955:

AAAUAAUCUG AUGAGGCCGA AAGGCCGAAA AUAAUA      36

( 2 ) INFORMATION FOR SEQ ID NO:956:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:956:

AAAUAAUCUG AUGAGGCCGA AAGGCCGAAA AUAAUA      36

( 2 ) INFORMATION FOR SEQ ID NO:957:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:957:

UAAAUAACUG AUGAGGCCGA AAGGCCGAAA AAUAAU      36

( 2 ) INFORMATION FOR SEQ ID NO:958:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:958:

AAUAAAUCUG AUGAGGCCGA AAGGCCGAAA UAAAUA      36

( 2 ) INFORMATION FOR SEQ ID NO:959:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:959:

AAUAAAUCUG AUGAGGCCGA AAGGCCGAAA UAAAUA      36

( 2 ) INFORMATION FOR SEQ ID NO:960:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:960:

AAUAAAUCUG AUGAGGCCGA AAGGCCGAAA UAAAUA      36

( 2 ) INFORMATION FOR SEQ ID NO:961:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:961:

AAAUAAACUG AUGAGGCCGA AAGGCCGAAA AUAAAU      36

( 2 ) INFORMATION FOR SEQ ID NO:962:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:962:

AAAUAAACUG AUGAGGCCGA AAGGCCGAAA AUAAAU      36

( 2 ) INFORMATION FOR SEQ ID NO:963:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:963:

AAAUAAACUG AUGAGGCCGA AAGGCCGAAA AUAAAU      36

( 2 ) INFORMATION FOR SEQ ID NO:964:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:964:

AUAAAUACUG AUGAGGCCGA AAGGCCGAAA UAAUAA      36

( 2 ) INFORMATION FOR SEQ ID NO:965:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:965:

AUAAAUACUG AUGAGGCCGA AAGGCCGAAA UAAUAA      36

( 2 ) INFORMATION FOR SEQ ID NO:966:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:966:

AUAAAUACUG AUGAGGCCGA AAGGCCGAAA UAAUAA      36

( 2 ) INFORMATION FOR SEQ ID NO:967:

( i ) SEQUENCE CHARACTERISTICS:
    ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:967:

AAUAAAUCUG AUGAGGCCGA AAGGCCGAAA AUAAUA 36

( 2 ) INFORMATION FOR SEQ ID NO:968:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:968:

AAUAAAUCUG AUGAGGCCGA AAGGCCGAAA AUAAUA 36

( 2 ) INFORMATION FOR SEQ ID NO:969:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:969:

UAAUAAACUG AUGAGGCCGA AAGGCCGAAA AAUAAU 36

( 2 ) INFORMATION FOR SEQ ID NO:970:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:970:

AAUAAUACUG AUGAGGCCGA AAGGCCGAAA UAAAUA 36

( 2 ) INFORMATION FOR SEQ ID NO:971:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:971:

AAAUAAUCUG AUGAGGCCGA AAGGCCGAAA AUAAAU 36

( 2 ) INFORMATION FOR SEQ ID NO:972:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:972:

UAAAUAACUG AUGAGGCCGA AAGGCCGAAA AAUAAA 36

( 2 ) INFORMATION FOR SEQ ID NO:973:

( i ) SEQUENCE CHARACTERISTICS:
( A ) LENGTH: 36 base pairs
( B ) TYPE: nucleic acid
( C ) STRANDEDNESS: single (D) TOPOLOGY: linear (x i) SEQUENCE DESCRIPTION: SEQ ID NO:973:

AAAUAAACUG AUGAGGCCGA AAGGCCGAAA AAUAAU 36

(2) INFORMATION FOR SEQ ID NO:974:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:974:

GCAAAUACUG AUGAGGCCGA AAGGCCGAAA UAAAUA 36

(2) INFORMATION FOR SEQ ID NO:975:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:975:

AGCAAAUCUG AUGAGGCCGA AAGGCCGAAA AUAAAU 36

(2) INFORMATION FOR SEQ ID NO:976:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:976:

AAGCAAACUG AUGAGGCCGA AAGGCCGAAA AAUAAA 36

(2) INFORMATION FOR SEQ ID NO:977:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:977:

AUAAGCACUG AUGAGGCCGA AAGGCCGAAA UAAAUA 36

(2) INFORMATION FOR SEQ ID NO:978:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:978:

CAUAAGCCUG AUGAGGCCGA AAGGCCGAAA AUAAAU 36

(2) INFORMATION FOR SEQ ID NO:979:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:979:

CAUUCAUCUG AUGAGGCCGA AAGGCCGAAA GCAAAU 36

( 2 ) INFORMATION FOR SEQ ID NO:980:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:980:

ACAUUCACUG AUGAGGCCGA AAGGCCGAAA AGCAAA 36

( 2 ) INFORMATION FOR SEQ ID NO:981:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:981:

AAAUAAACUG AUGAGGCCGA AAGGCCGAAA CAUUCA 36

( 2 ) INFORMATION FOR SEQ ID NO:982:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:982:

CCAAAUACUG AUGAGGCCGA AAGGCCGAAA UACAUU 36

( 2 ) INFORMATION FOR SEQ ID NO:983:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:983:

UCCAAAUCUG AUGAGGCCGA AAGGCCGAAA AUACAU 36

( 2 ) INFORMATION FOR SEQ ID NO:984:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:984:

UUCCAAACUG AUGAGGCCGA AAGGCCGAAA AAUACA 36

( 2 ) INFORMATION FOR SEQ ID NO:985:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:985:

CCUUCCACUG AUGAGGCCGA AAGGCCGAAA UAAAUA 36

( 2 ) INFORMATION FOR SEQ ID NO:986:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:986:

CCUUCCACUG AUGAGGCCGA AAGGCCGAAA UAAAUA 36

( 2 ) INFORMATION FOR SEQ ID NO:987:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:987:

GCCUUCCCUG AUGAGGCCGA AAGGCCGAAA AUAAAU 36

( 2 ) INFORMATION FOR SEQ ID NO:988:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:988:

CCUCCAGCUG AUGAGGCCGA AAGGCCGAAA CACCCC 36

( 2 ) INFORMATION FOR SEQ ID NO:989:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:989:

CUGUCUGCUG AUGAGGCCGA AAGGCCGAAA GACAGC 36

( 2 ) INFORMATION FOR SEQ ID NO:990:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:990:

CUGUCUGCUG AUGAGGCCGA AAGGCCGAAA GACAGC 36

( 2 ) INFORMATION FOR SEQ ID NO:991:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:991:

CACAGAACUG AUGAGGCCGA AAGGCCGAAA CAUGUC 36

( 2 ) INFORMATION FOR SEQ ID NO:992:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:992:

UCACAGACUG AUGAGGCCGA AAGGCCGAAA ACAUGU      36

( 2 ) INFORMATION FOR SEQ ID NO:993:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:993:

UUCACAGCUG AUGAGGCCGA AAGGCCGAAA AACAUG      36

( 2 ) INFORMATION FOR SEQ ID NO:994:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:994:

UUUCACACUG AUGAGGCCGA AAGGCCGAAA AAACAU      36

( 2 ) INFORMATION FOR SEQ ID NO:995:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:995:

UUUCACACUG AUGAGGCCGA AAGGCCGAAA AAACAU      36

( 2 ) INFORMATION FOR SEQ ID NO:996:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:996:

AGGUGGGCUG AUGAGGCCGA AAGGCCGAAA CAGCUC      36

( 2 ) INFORMATION FOR SEQ ID NO:997:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:997:

AGGUAGACUG AUGAGGCCGA AAGGCCGAAA GGCCAG      36

( 2 ) INFORMATION FOR SEQ ID NO:998:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:998:

CAAGGUACUG AUGAGGCCGA AAGGCCGAAA GAGGCC 36

( 2 ) INFORMATION FOR SEQ ID NO:999:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:999:

AACAAGGCUG AUGAGGCCGA AAGGCCGAAA GAGAGG 36

( 2 ) INFORMATION FOR SEQ ID NO:1000:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1000:

AGGAGGCCUG AUGAGGCCGA AAGGCCGAAA CAAGGU 36

( 2 ) INFORMATION FOR SEQ ID NO:1001:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1001:

AGCAAAACUG AUGAGGCCGA AAGGCCGAAA GGAGGC 36

( 2 ) INFORMATION FOR SEQ ID NO:1002:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1002:

UAAGCAACUG AUGAGGCCGA AAGGCCGAAA GAGGAG 36

( 2 ) INFORMATION FOR SEQ ID NO:1003:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1003:

AUAAGCACUG AUGAGGCCGA AAGGCCGAAA AGAGGA 36

( 2 ) INFORMATION FOR SEQ ID NO:1004:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1004:

CAUAAGCCUG AUGAGGCCGA AAGGCCGAAA AAGAGG 36

( 2 ) INFORMATION FOR SEQ ID NO:1005:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1005:

UAAACAUCUG AUGAGGCCGA AAGGCCGAAA GCAAAA 36

( 2 ) INFORMATION FOR SEQ ID NO:1006:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1006:

UUAAACACUG AUGAGGCCGA AAGGCCGAAA AGCAAA 36

( 2 ) INFORMATION FOR SEQ ID NO:1007:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1007:

UUAAACACUG AUGAGGCCGA AAGGCCGAAA AGCAAA 36

( 2 ) INFORMATION FOR SEQ ID NO:1008:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1008:

UUGUUUUCUG AUGAGGCCGA AAGGCCGAAA ACAUAA 36

( 2 ) INFORMATION FOR SEQ ID NO:1009:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1009:

GUUAGAUCUG AUGAGGCCGA AAGGCCGAAA AUAUUU 36

( 2 ) INFORMATION FOR SEQ ID NO:1010:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO:1010:

UUAAGACCUG AUGAGGCCGA AAGGCCGAAA UUGGGU 36

( 2 ) INFORMATION FOR SEQ ID NO:1011:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1011:

UUAUUAACUG AUGAGGCCGA AAGGCCGAAA CAAUUG 36

( 2 ) INFORMATION FOR SEQ ID NO:1012:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1012:

CGUUAUUCUG AUGAGGCCGA AAGGCCGAAA GACAAU 36

( 2 ) INFORMATION FOR SEQ ID NO:1013:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1013:

GUCACCACUG AUGAGGCCGA AAGGCCGAAA UCAGCG 36

( 2 ) INFORMATION FOR SEQ ID NO:1014:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1014:

GUCACCACUG AUGAGGCCGA AAGGCCGAAA UCAGCG 36

( 2 ) INFORMATION FOR SEQ ID NO:1015:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1015:

GGUCACCCUG AUGAGGCCGA AAGGCCGAAA AUCAGC 36

( 2 ) INFORMATION FOR SEQ ID NO:1016:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1016:

GGUCACCCUG AUGAGGCCGA AAGGCCGAAA AUCAGC  36

( 2 ) INFORMATION FOR SEQ ID NO:1017:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1017:

GGGAGCACUG AUGAGGCCGA AAGGCCGAAA GGUUCA  36

( 2 ) INFORMATION FOR SEQ ID NO:1018:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1018:

GGGAGCACUG AUGAGGCCGA AAGGCCGAAA GGUUCA  36

( 2 ) INFORMATION FOR SEQ ID NO:1019:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1019:

CCGUGGGCUG AUGAGGCCGA AAGGCCGAAA GCAGAG  36

( 2 ) INFORMATION FOR SEQ ID NO:1020:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1020:

GGGCAAUCUG AUGAGGCCGA AAGGCCGAAA CAGUCA  36

( 2 ) INFORMATION FOR SEQ ID NO:1021:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1021:

GUAGGGCCUG AUGAGGCCGA AAGGCCGAAA UUACAG  36

( 2 ) INFORMATION FOR SEQ ID NO:1022:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1022:

CGAUCUUCUG AUGAGGCCGA AAGGCCGAAA UUUCUC 36

( 2 ) INFORMATION FOR SEQ ID NO:1023:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1023:

UUUAAGCCUG AUGAGGCCGA AAGGCCGAAA UCUUUA 36

( 2 ) INFORMATION FOR SEQ ID NO:1024:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1024:

GGUUUUUCUG AUGAGGCCGA AAGGCCGAAA UUUUAA 36

( 2 ) INFORMATION FOR SEQ ID NO:1025:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1025:

AGCCGUGGAG AAGUAUGUAC CAGAGAAACA CACGUUGUGG UACAUUACCU GGUA 54

( 2 ) INFORMATION FOR SEQ ID NO:1026:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1026:

GAGGUGGAG AAGUGGGUAC CAGAGAAACA CACGUUGUGG UACAUUACCU GGUA 54

( 2 ) INFORMATION FOR SEQ ID NO:1027:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1027:

GGAGAAGAAG AAGAGGAAAC CAGAGAAACA CACGUUGUGG UACAUUACCU GGUA 54

( 2 ) INFORMATION FOR SEQ ID NO:1028:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1028:

CUGCCACGAG AAGGAAGGAC CAGAGAAACA CACGUUGUGG UACAUUACCU GGUA 54

( 2 ) INFORMATION FOR SEQ ID NO:1029:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1029:

GUGCAGCAAG AAGAAGAGAC CAGAGAAACA CACGUUGUGG UACAUUACCU GGUA  54

( 2 ) INFORMATION FOR SEQ ID NO:1030:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1030:

CAAAGUGCAG AAGGCAGAAC CAGAGAAACA CACGUUGUGG UACAUUACCU GGUA  54

( 2 ) INFORMATION FOR SEQ ID NO:1031:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1031:

CCUCUGGGAG AAGAUCACAC CAGAGAAACA CACGUUGUGG UACAUUACCU GGUA  54

( 2 ) INFORMATION FOR SEQ ID NO:1032:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1032:

GGCCAGAGAG AAGAUUAGAC CAGAGAAACA CACGUUGUGG UACAUUACCU GGUA  54

( 2 ) INFORMATION FOR SEQ ID NO:1033:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1033:

AGAAGAUGAG AAGACUGCAC CAGAGAAACA CACGUUGUGG UACAUUACCU GGUA  54

( 2 ) INFORMATION FOR SEQ ID NO:1034:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1034:

GCCACUGGAG AAGCCCUAC CAGAGAAACA CACGUUGUGG UACAUUACCU GGUA  54

( 2 ) INFORMATION FOR SEQ ID NO:1035:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1035:

AUUGGCCCAG AAGUUCAGAC CAGAGAAACA CACGUUGUGG UACAUUACCU GGUA    54

( 2 ) INFORMATION FOR SEQ ID NO:1036:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1036:

GCACCACCAG AAGGUUAUAC CAGAGAAACA CACGUUGUGG UACAUUACCU GGUA    54

( 2 ) INFORMATION FOR SEQ ID NO:1037:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1037:

GGUGGAGGAG AAGCCUUGAC CAGAGAAACA CACGUUGUGG UACAUUACCU GGUA    54

( 2 ) INFORMATION FOR SEQ ID NO:1038:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1038:

GGCGAUGCAG AAGAUGGUAC CAGAGAAACA CACGUUGUGG UACAUUACCU GGUA    54

( 2 ) INFORMATION FOR SEQ ID NO:1039:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1039:

UGGUAGGAAG AAGCGAUGAC CAGAGAAACA CACGUUGUGG UACAUUACCU GGUA    54

( 2 ) INFORMATION FOR SEQ ID NO:1040:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1040:

UGACCUUGAG AAGGUAGGAC CAGAGAAACA CACGUUGUGG UACAUUACCU GGUA    54

( 2 ) INFORMATION FOR SEQ ID NO:1041:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1041:

CCUUCUCCAG AAGGAAGAAC CAGAGAAACA CACGUUGUGG UACAUUACCU GGUA    54

( 2 ) INFORMATION FOR SEQ ID NO:1042:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1042:

AGCGCUGAAG AAGUCACCAC CAGAGAAACA CACGUUGUGG UACAUUACCU GGUA    54

( 2 ) INFORMATION FOR SEQ ID NO:1043:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1043:

GAUAGUCGAG AAGAUUGAAC CAGAGAAACA CACGUUGUGG UACAUUACCU GGUA    54

( 2 ) INFORMATION FOR SEQ ID NO:1044:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1044:

UCGAGAUAAG AAGGCCGAAC CAGAGAAACA CACGUUGUGG UACAUUACCU GGUA    54

( 2 ) INFORMATION FOR SEQ ID NO:1045:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1045:

GGGAUUGGAG AAGGGGAGAC CAGAGAAACA CACGUUGUGG UACAUUACCU GGUA    54

( 2 ) INFORMATION FOR SEQ ID NO:1046:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1046:

GGGAUCAAAG AAGUAGGCAC CAGAGAAACA CACGUUGUGG UACAUUACCU GGUA    54

( 2 ) INFORMATION FOR SEQ ID NO:1047:

( i ) SEQUENCE CHARACTERISTICS:
    ( A ) LENGTH: 54 base pairs ( B ) TYPE: nucleic acid
                ( C ) STRANDEDNESS: single
                ( D ) TOPOLOGY: linear ( x i ) SEQUENCE DESCRIPTION: SEQ ID NO:1047:

CUGGAAACAG AAGGAGAGAC CAGAGAAACA CACGUUGUGG UACAUUACCU GGUA     54

( 2 ) INFORMATION FOR SEQ ID NO:1048:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1048:

UCAAGGAAAG AAGGAAACAC CAGAGAAACA CACGUUGUGG UACAUUACCU GGUA     54

( 2 ) INFORMATION FOR SEQ ID NO:1049:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1049:

AUGGGGAGAG AAGGGCUCAC CAGAGAAACA CACGUUGUGG UACAUUACCU GGUA     54

( 2 ) INFORMATION FOR SEQ ID NO:1050:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1050:

AUAGAGGGAG AAGGCUCCAC CAGAGAAACA CACGUUGUGG UACAUUACCU GGUA     54

( 2 ) INFORMATION FOR SEQ ID NO:1051:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1051:

AUACAUUCAG AAGUAAAUAC CAGAGAAACA CACGUUGUGG UACAUUACCU GGUA     54

( 2 ) INFORMATION FOR SEQ ID NO:1052:

( i ) SEQUENCE CHARACTERISTICS:
                ( A ) LENGTH: 54 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1052:

UGAGCCAAAG AAGCUCCUAC CAGAGAAACA CACGUUGUGG UACAUUACCU GGUA     54

( 2 ) INFORMATION FOR SEQ ID NO:1053:

( i ) SEQUENCE CHARACTERISTICS:
                ( A ) LENGTH: 54 base pairs
                ( B ) TYPE: nucleic acid
                ( C ) STRANDEDNESS: single (D) TOPOLOGY: linear (x i) SEQUENCE DESCRIPTION: SEQ ID NO:1053:

UACAUGGGAG AAGCCUAUAC CAGAGAAACA CACGUUGUGG UACAUUACCU GGUA 54

(2) INFORMATION FOR SEQ ID NO:1054:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:1054:

ACAACUUAAG AAGAUAAUAC CAGAGAAACA CACGUUGUGG UACAUUACCU GGUA 54

(2) INFORMATION FOR SEQ ID NO:1055:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:1055:

GUCACCAAAG AAGCAUUGAC CAGAGAAACA CACGUUGUGG UACAUUACCU GGUA 54

(2) INFORMATION FOR SEQ ID NO:1056:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:1056:

CCCUGGGGAG AAGAGGCCAC CAGAGAAACA CACGUUGUGG UACAUUACCU GGUA 54

(2) INFORMATION FOR SEQ ID NO:1057:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (x i) SEQUENCE DESCRIPTION: SEQ ID NO:1057:

GAAUAGUAAG AAGAUUACAC CAGAGAAACA CACGUUGUGG UACAUUACCU GGUA 54

(2) INFORMATION FOR SEQ ID NO:1058:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1058:

ACAUACUGAC CCACGGCU 18

(2) INFORMATION FOR SEQ ID NO:1059:

(i) SEQUENCE CHARACTERISTICS:
        (A) LENGTH: 18 base pairs
        (B) TYPE: nucleic acid
        (C) STRANDEDNESS: single
        (D) TOPOLOGY: linear ( x i ) SEQUENCE DESCRIPTION: SEQ ID NO:1059:

ACCCACGGCU CCACCCUC 18

( 2 ) INFORMATION FOR SEQ ID NO:1060:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1060:

UUCCUCAGCC UCUUCUCC 18

( 2 ) INFORMATION FOR SEQ ID NO:1061:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1061:

CCUUCCUGAU CGUGGCAG 18

( 2 ) INFORMATION FOR SEQ ID NO:1062:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1062:

CUCUUCUGCC UGCUGCAC 18

( 2 ) INFORMATION FOR SEQ ID NO:1063:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1063:

UCUGCCUGCU GCACUUUG 18

( 2 ) INFORMATION FOR SEQ ID NO:1064:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1064:

GUGAUCGGCC CCCAGAGG 18

( 2 ) INFORMATION FOR SEQ ID NO:1065:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1065:

CUAAUCAGCC CUCUGGCC 18

( 2 ) INFORMATION FOR SEQ ID NO:1066:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1066:

GCAGUCAGAU CAUCUUCU 18

( 2 ) INFORMATION FOR SEQ ID NO:1067:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1067:

AGGGGCAGCU CCAGUGGC 18

( 2 ) INFORMATION FOR SEQ ID NO:1068:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1068:

CUGAACCGCC GGGCCAAU 18

( 2 ) INFORMATION FOR SEQ ID NO:1069:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1069:

AUAACCAGCU GGUGGUGC 18

( 2 ) INFORMATION FOR SEQ ID NO:1070:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1070:

CAAGGCUGCC CCUCCACC 18

( 2 ) INFORMATION FOR SEQ ID NO:1071:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1071:

ACCAUCAGCC GCAUCGCC 18

( 2 ) INFORMATION FOR SEQ ID NO:1072:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1072:

CAUCGCCGUC UCCUACCA 18

( 2 ) INFORMATION FOR SEQ ID NO:1073:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1073:

CCUACCAGAC CAAGGUCA 18

( 2 ) INFORMATION FOR SEQ ID NO:1074:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1074:

UCUUCCAGCU GGAGAAGG 18

( 2 ) INFORMATION FOR SEQ ID NO:1075:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1075:

GGUGACCGAC UCAGCGCU 18

( 2 ) INFORMATION FOR SEQ ID NO:1076:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1076:

UCAAUCGGCC CGACUAUC 18

( 2 ) INFORMATION FOR SEQ ID NO:1077:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1077:

UCGGCCCGAC UAUCUCGA 18

( 2 ) INFORMATION FOR SEQ ID NO:1078:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1078:

CUCCCCUGCC CCAAUCCC 18

( 2 ) INFORMATION FOR SEQ ID NO:1079:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1079:

GCCUACAGCU UUGAUCCC 18

( 2 ) INFORMATION FOR SEQ ID NO:1080:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1080:

CUCUCCAGAU GUUUCCAG 18

( 2 ) INFORMATION FOR SEQ ID NO:1081:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1081:

GUUUCCAGAC UUCCUUGA 18

( 2 ) INFORMATION FOR SEQ ID NO:1082:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1082:

GAGCCCAGCC CUCCCCAU 18

( 2 ) INFORMATION FOR SEQ ID NO:1083:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1083:

GGAGCCAGCU CCCUCUAU 18

( 2 ) INFORMATION FOR SEQ ID NO:1084:

( i ) SEQUENCE CHARACTERISTICS:

(A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1084:

AUUUACAGAU GAAUGUAU                                                                                             18

(2) INFORMATION FOR SEQ ID NO:1085:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1085:

AGGAGCUGCC UUGGCUCA                                                                                             18

(2) INFORMATION FOR SEQ ID NO:1086:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1086:

AUAGGCUGUU CCCAUGUA                                                                                             18

(2) INFORMATION FOR SEQ ID NO:1087:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1087:

AUUAUCUGAU UAAGUUGU                                                                                             18

(2) INFORMATION FOR SEQ ID NO:1088:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1088:

CAAUGCUGAU UUGGUGAC                                                                                             18

(2) INFORMATION FOR SEQ ID NO:1089:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:1089:

GGCCUCUGCU CCCCAGGG                                                                                             18

(2) INFORMATION FOR SEQ ID NO:1090:

(i) SEQUENCE CHARACTERISTICS:
                (A) LENGTH: 18 base pairs
                (B) TYPE: nucleic acid (  C  ) STRANDEDNESS: single
    (  D  ) TOPOLOGY: linear (  x i  ) SEQUENCE DESCRIPTION: SEQ ID NO:1090:

GUAAUCGGCC UACUAUUC                18

( 2 ) INFORMATION FOR SEQ ID NO:1091:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO:1091:

GUGAAAGGAG AAGAACCUAC CAGAGAAACA CACGUUGUGG UACAUUACCU GGUA        54

( 2 ) INFORMATION FOR SEQ ID NO:1092:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO:1092:

UGAGAAGAAG AAGAGACAAC CAGAGAAACA CACGUUGUGG UACAUUACCU GGUA        54

( 2 ) INFORMATION FOR SEQ ID NO:1093:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO:1093:

CUGCCACAAG AAGGAAUGAC CAGAGAAACA CACGUUGUGG UACAUUACCU GGUA        54

( 2 ) INFORMATION FOR SEQ ID NO:1094:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO:1094:

GUUCAGUAAG AAGAAGAGAC CAGAGAAACA CACGUUGUGG UACAUUACCU GGUA        54

( 2 ) INFORMATION FOR SEQ ID NO:1095:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO:1095:

CCUUUGGGAG AAGAUCACAC CAGAGAAACA CACGUUGUGG UACAUUACCU GGUA        54

( 2 ) INFORMATION FOR SEQ ID NO:1096:

(  i  ) SEQUENCE CHARACTERISTICS:
        (  A  ) LENGTH: 54 base pairs
        (  B  ) TYPE: nucleic acid
        (  C  ) STRANDEDNESS: single
        (  D  ) TOPOLOGY: linear ( x i ) SEQUENCE DESCRIPTION: SEQ ID NO:1096:

GGCCAUAGAG AAGAUGAGAC CAGAGAAACA CACGUUGUGG UACAUUACCU GGUA        54

( 2 ) INFORMATION FOR SEQ ID NO:1097:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1097:

GUGUGAGGAG AAGGGCCAAC CAGAGAAACA CACGUUGUGG UACAUUACCU GGUA        54

( 2 ) INFORMATION FOR SEQ ID NO:1098:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1098:

AGAAGAUGAG AAGAGUGUAC CAGAGAAACA CACGUUGUGG UACAUUACCU GGUA        54

( 2 ) INFORMATION FOR SEQ ID NO:1099:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1099:

GCCACUCCAG AAGCUCCUAC CAGAGAAACA CACGUUGUGG UACAUUACCU GGUA        54

( 2 ) INFORMATION FOR SEQ ID NO:1100:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1100:

AACCCAUCAG AAGGCACCAC CAGAGAAACA CACGUUGUGG UACAUUACCU GGUA        54

( 2 ) INFORMATION FOR SEQ ID NO:1101:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1101:

UACAACCCAG AAGCUGGCAC CAGAGAAACA CACGUUGUGG UACAUUACCU GGUA        54

( 2 ) INFORMATION FOR SEQ ID NO:1102:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1102:

```
GUAGUCGGAG  AAGCCUUGAC  CAGAGAAACA  CACGUUGUGG  UACAUUACCU  GGUA                    54
```

( 2 ) INFORMATION FOR SEQ ID NO:1103:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

```
AGCACGUAAG  AAGGGCAGAC  CAGAGAAACA  CACGUUGUGG  UACAUUACCU  GGUA                    54
```

( 2 ) INFORMATION FOR SEQ ID NO:1104:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1104:

```
AGCAAAUCAG  AAGACGGUAC  CAGAGAAACA  CACGUUGUGG  UACAUUACCU  GGUA                    54
```

( 2 ) INFORMATION FOR SEQ ID NO:1105:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

```
GAUAGCAAAG  AAGCUGACAC  CAGAGAAACA  CACGUUGUGG  UACAUUACCU  GGUA                    54
```

( 2 ) INFORMATION FOR SEQ ID NO:1106:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1106:

```
CUCUUGACAG  AAGAGAGGAC  CAGAGAAACA  CACGUUGUGG  UACAUUACCU  GGUA                    54
```

( 2 ) INFORMATION FOR SEQ ID NO:1107:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1107:

```
GUCCUUGGAG  AAGGGGCUAC  CAGAGAAACA  CACGUUGUGG  UACAUUACCU  GGUA                    54
```

( 2 ) INFORMATION FOR SEQ ID NO:1108:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1108:

```
CCUUCUCCAG  AAGGAAGAAC  CAGAGAAACA  CACGUUGUGG  UACAUUACCU  GGUA                    54
```

( 2 ) INFORMATION FOR SEQ ID NO:1109:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1109:

AGUACUUGAG AAGAUUGAAC CAGAGAAACA CACGUUGUGG UACAUUACCU GGUA  54

( 2 ) INFORMATION FOR SEQ ID NO:1110:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1110:

AGAGUGGGAG AAGGGUAGAC CAGAGAAACA CACGUUGUGG UACAUUACCU GGUA  54

( 2 ) INFORMATION FOR SEQ ID NO:1111:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1111:

GUAAGGGAG AAGAGUGGAC CAGAGAAACA CACGUUGUGG UACAUUACCU GGUA  54

( 2 ) INFORMATION FOR SEQ ID NO:1112:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1112:

AUAAGGGAG AAGAGUAAAC CAGAGAAACA CACGUUGUGG UACAUUACCU GGUA  54

( 2 ) INFORMATION FOR SEQ ID NO:1113:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1113:

AGGACACAAG AAGGGGCAC CAGAGAAACA CACGUUGUGG UACAUUACCU GGUA  54

( 2 ) INFORMATION FOR SEQ ID NO:1114:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1114:

CAUUCUGAAG AAGAGGCAAC CAGAGAAACA CACGUUGUGG UACAUUACCU GGUA  54

( 2 ) INFORMATION FOR SEQ ID NO:1115:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1115:

CUGGAAAGAG AAGAAGGUAC CAGAGAAACA CACGUUGUGG UACAUUACCU GGUA    54

( 2 ) INFORMATION FOR SEQ ID NO:1116:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1116:

AGGGAAGAAG AAGGAAAGAC CAGAGAAACA CACGUUGUGG UACAUUACCU GGUA    54

( 2 ) INFORMATION FOR SEQ ID NO:1117:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1117:

GUGAGGAAAG AAGUGCAUAC CAGAGAAACA CACGUUGUGG UACAUUACCU GGUA    54

( 2 ) INFORMATION FOR SEQ ID NO:1118:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1118:

UAGAGGGGAG AAGGCUCUAC CAGAGAAACA CACGUUGUGG UACAUUACCU GGUA    54

( 2 ) INFORMATION FOR SEQ ID NO:1119:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1119:

UGUCUGAAAG AAGCUUCCAC CAGAGAAACA CACGUUGUGG UACAUUACCU GGUA    54

( 2 ) INFORMATION FOR SEQ ID NO:1120:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1120:

CAGGUGGGAG AAGCUCAGAC CAGAGAAACA CACGUUGUGG UACAUUACCU GGUA    54

( 2 ) INFORMATION FOR SEQ ID NO:1121:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1121:

GUCACCAAAG AAGCGUUAAC CAGAGAAACA CACGUUGUGG UACAUUACCU GGUA    54

( 2 ) INFORMATION FOR SEQ ID NO:1122:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1122:

GAUGUAGCAG AAGCCUGGAC CAGAGAAACA CACGUUGUGG UACAUUACCU GGUA    54

( 2 ) INFORMATION FOR SEQ ID NO:1123:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1123:

CCGUGGGAG AAGAGGUUAC CAGAGAAACA CACGUUGUGG UACAUUACCU GGUA    54

( 2 ) INFORMATION FOR SEQ ID NO:1124:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1124:

AGGUUCUGUC CCUUUCAC    18

( 2 ) INFORMATION FOR SEQ ID NO:1125:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1125:

UGUCUCAGCC UCUUCUCA    18

( 2 ) INFORMATION FOR SEQ ID NO:1126:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1126:

CAUUCCUGCU UGUGGCAG    18

( 2 ) INFORMATION FOR SEQ ID NO:1127:

( i ) SEQUENCE CHARACTERISTICS:
    ( A ) LENGTH: 18 base pairs (B) TYPE: nucleic acid
(C) STRANDEDNESS: single
(D) TOPOLOGY: linear (xi) SEQUENCE DESCRIPTION: SEQ ID NO:1127:

CUCUUCUGUC UACUGAAC 18

(2) INFORMATION FOR SEQ ID NO:1128:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1128:

GUGAUCGGUC CCCAAAGG 18

(2) INFORMATION FOR SEQ ID NO:1129:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1129:

CUCAUCAGUU CUAUGGCC 18

(2) INFORMATION FOR SEQ ID NO:1130:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1130:

UGGCCCAGAC CCUCACAC 18

(2) INFORMATION FOR SEQ ID NO:1131:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1131:

ACACUCAGAU CAUCUUCU 18

(2) INFORMATION FOR SEQ ID NO:1132:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1132:

AGGAGCAGCU GGAGUGGC 18

(2) INFORMATION FOR SEQ ID NO:1133:

(i) SEQUENCE CHARACTERISTICS:
(A) LENGTH: 18 base pairs
(B) TYPE: nucleic acid
(C) STRANDEDNESS: single ( D ) TOPOLOGY: linear ( x i ) SEQUENCE DESCRIPTION: SEQ ID NO:1133:

GGUGCCAGCC GAUGGGUU                                                                                 18

( 2 ) INFORMATION FOR SEQ ID NO:1134:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1134:

GCCAGCCGAU GGGUUGUA                                                                                 18

( 2 ) INFORMATION FOR SEQ ID NO:1135:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1135:

CAAGGCUGCC CCGACUAC                                                                                 18

( 2 ) INFORMATION FOR SEQ ID NO:1136:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1136:

CUGCCCCGAC UACGUGCU                                                                                 18

( 2 ) INFORMATION FOR SEQ ID NO:1137:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1137:

ACCGUCAGCC GAUUUGCU                                                                                 18

( 2 ) INFORMATION FOR SEQ ID NO:1138:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1138:

GUCAGCCGAU UUGCUAUC                                                                                 18

( 2 ) INFORMATION FOR SEQ ID NO:1139:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear (x i) SEQUENCE DESCRIPTION: SEQ ID NO:1139:

CCUCUCUGCC GUCAAGAG 18

(2) INFORMATION FOR SEQ ID NO:1140:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1140:

AGCCCCUGCC CCAAGGAC 18

(2) INFORMATION FOR SEQ ID NO:1141:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1141:

UCUUCCAGCU GGAGAAGG 18

(2) INFORMATION FOR SEQ ID NO:1142:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1142:

UCAAUCUGCC CAAGUACU 18

(2) INFORMATION FOR SEQ ID NO:1143:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1143:

CUACCCAGCC CCCACUCU 18

(2) INFORMATION FOR SEQ ID NO:1144:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1144:

CCACUCUGAC CCCUUUAC 18

(2) INFORMATION FOR SEQ ID NO:1145:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:1145:

UUACUCUGAC CCCUUUAU                                                                                          18

( 2 ) INFORMATION FOR SEQ ID NO:1146:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1146:

GCCCCCAGUC UGUGUCCU                                                                                          18

( 2 ) INFORMATION FOR SEQ ID NO:1147:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1147:

UGCCUCUGUC UCAGAAUG                                                                                          18

( 2 ) INFORMATION FOR SEQ ID NO:1148:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1148:

ACCUUCAGAC CUUUCCAG                                                                                          18

( 2 ) INFORMATION FOR SEQ ID NO:1149:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1149:

CUUUCCAGAC UCUUCCCU                                                                                          18

( 2 ) INFORMATION FOR SEQ ID NO:1150:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1150:

AUGCACAGCC UUCCUCAC                                                                                          18

( 2 ) INFORMATION FOR SEQ ID NO:1151:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1151:

AGAGCCAGCC CCCCUCUA                                                                                          18

( 2 ) INFORMATION FOR SEQ ID NO:1152:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1152:

GGAAGCUGUC UUCAGACA					18

( 2 ) INFORMATION FOR SEQ ID NO:1153:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1153:

CUGAGCUGUC CCCACCUG					18

( 2 ) INFORMATION FOR SEQ ID NO:1154:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1154:

UAACGCUGAU UUGGUGAC					18

( 2 ) INFORMATION FOR SEQ ID NO:1155:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1155:

CCAGGCUGUC GCUACAUC					18

( 2 ) INFORMATION FOR SEQ ID NO:1156:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1156:

AACCUCUGCU CCCCACGG					18

( 2 ) INFORMATION FOR SEQ ID NO:1157:

( i ) SEQUENCE CHARACTERISTICS:
　　　　( A ) LENGTH: 12 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1157:

GGCCGAAAGG CC						12

We claim: 1. An enzymatic RNA molecule which cleaves TNF-α mRNA wherein said enzymatic RNA molecule comprises sequences complementary to any of sequences defined as Seq ID Nos. 15–267, 522–772, 1058–1090, or 1124–1156.

2. An enzymatic RNA molecule which cleaves TNF-α mRNA the binding arms of which contain sequences complementary to the sequences defined as Seq. ID Nos. 15–267 or 522–772, wherein said enzymatic RNA molecule is in a hammerhead motif.

3. An enzymatic RNA molecule which cleaves TNF-α mRNA, the binding arms of which contain sequences complementary to the sequences defined as Seq. ID Nos. 1058–1090 or 1124–1156, wherein said enzymatic RNA molecule is in a hairpin motif.

4. The enzymatic RNA molecule of claim 2 or 3, wherein said ribozyme comprises between 12 and 100 bases complementary to said mRNA.

5. The enzymatic RNA molecule of claim 4, wherein said ribozyme comprises between 14 and 24 bases complementary to said mRNA.

6. The enzymatic RNA molecule of claim 2, wherein said enzymatic RNA molecule comprises any sequence selected from the group consisting of Sequence ID Nos. 268–521, and 773–1024.

7. A mammalian cell in vitro including an enzymatic RNA molecule of claims 2 or 3.

8. The cell of claim 7, wherein said cell is a human cell.

9. An expression vector including nucleic acid encoding an enzymatic RNA molecule or multiple enzymatic molecules of claims 1, 2, or 3 in a manner which allows expression of that enzymatic RNA molecule(s) within a mammalian cell in vitro.

10. A mammalian cell including an expression vector of claim 9.

11. The cell of claim 10, wherein said cell is a human cell.

12. The enzymatic RNA molecule of claim 1, wherein said enzymatic RNA molecule comprises at least one sugar modification.

13. The enzymatic RNA molecule of claim 3, wherein said enzymatic RNA molecule comprises any sequence selected from the group consisting of Sequence ID Nos. 1025–1057, and 1091–1123.

* * * * *